United States Patent
Huang et al.

(10) Patent No.: US 7,785,807 B2
(45) Date of Patent: Aug. 31, 2010

(54) VOLTAGE-GATED, PH-SENSITIVE ANION CHANNEL AND ITS NOVEL SPLICE VARIANT INVOLVED IN TASTE SENSATION

(75) Inventors: Liquan Huang, Havertown, PA (US); Jie Cao, Upper Darby, PA (US); Hong Wang, Havertown, PA (US); Joseph G Brand, Wayne, PA (US)

(73) Assignee: Monell Chemical Senses Center, Philadelphia, PA (US)

( * ) Notice: Subject to any disclaimer, the term of this patent is extended or adjusted under 35 U.S.C. 154(b) by 47 days.

(21) Appl. No.: 11/721,597

(22) PCT Filed: Dec. 13, 2005

(86) PCT No.: PCT/US2005/045542

§ 371 (c)(1),
(2), (4) Date: May 6, 2008

(87) PCT Pub. No.: WO2006/066064

PCT Pub. Date: Jun. 22, 2006

(65) Prior Publication Data

US 2008/0307536 A1    Dec. 11, 2008

Related U.S. Application Data

(60) Provisional application No. 60/635,675, filed on Dec. 13, 2004.

(51) Int. Cl.
C07K 14/705  (2006.01)
C12N 15/12  (2006.01)
G01N 33/566  (2006.01)

(52) U.S. Cl. .............. 435/7.21; 435/7.2; 435/69.1; 435/252.3; 435/320.1; 530/351; 536/23.5

(58) Field of Classification Search .................. None
See application file for complete search history.

(56) References Cited

U.S. PATENT DOCUMENTS 7,250,262 B2 * 7/2007 Carroll et al. ................ 435/7.1
2004/0265837 A1  12/2004 Jentsch .......................... 435/6

FOREIGN PATENT DOCUMENTS

WO  91/09955 A1  7/1991
WO  92/20808 A1  11/1992
WO  94/12650 A2  6/1994

OTHER PUBLICATIONS

Sakurai, N. et al., "Effects of acids on neural activity elicited by other taste stimuli in the rat chorda tympani," *Brain Res.*, 2000, 859(2), 369-372.
Hoon, M. A. et al., "Putative Mammalian Taste Receptors: A Class of Taste-Specific Gpcrs With Distinct Topographic Selectivity," *Cell*, 1999, 96(4), 541-551.
Buck, L. & Axel, R., "A Novel Multigene Family May Encode Odorant Receptors: A Molecular Basis for Odor Recognition," *Cell*, 1991, 65, 175-187.
Palmer, S. et al., "A contravention of Ohno's law in mice," *Nat. Genet.*, 1995, 10(4), 472-476.
Rugarli, E. I. et al., "Different chromosomal localization of the Clcn4 gene in *Mus spretus* and C57BL/6J mice," *Nat. Genet.*, 1995, 4, 466-471.
Dutzler et al., "X-ray structure of a ClC chloride channel at 3.0 A reveals the molecular basis of anion selectivity," *Nature*, 2002, 415, 287-294.
Estevez and Jentsch, "CLC choloride channels: correlating structure with function," *Curr. Opin. Struct. Biol.*, 2002, 12, 531-539.
Ruiz, C. et al., "Tissue culture of rat taste buds," *Experimental Cell Biology of Taste and Olfaction, Current Techniques and Protocols* (eds. Spielman, A.I, and Brand, J.G.), 79-84 (CRC Press, Boca Raton, Florida, 1995).
Brady, G. et al., "Construction of cDNA libraries from single cells," *Methods Enzymol.*, 1993, 225, 611-623.
Dulac, C. et al., "A novel family of genes encoding putative pheromone receptors in mammals," *Cell*, 1995, 83, 195-206.
Huang, L. et al., "Gγ13 colocalizes with gustducin in taste receptor cells and mediates IP3 responses to bitter denatonium," *Nature Neurosci.*, 1999, 1055-1062.
Perez, C. A. et al., "A transient receptor potential channel expressed in taste receptor cells," *Nature Neurosci.*, 2002, 5, 1169-1176.
Schaeren-Wiemers, N. et al., "A single protocol to detect transcripts of various types and expression levels in neural tissue and cultured cells: in situ hybridization using digoxigenin-labeled cRNA probes," *Histochemistry*, 1993, 100, 431-440.
Mohammad-Panah, R. et al., "The Chloride Channel ClC-4 Contributes to Endosomal Acidification and Trafficking," *J. Biol. Chem.*, 2003, 278(31)), 29267-29277.

* cited by examiner

*Primary Examiner*—John D Ulm
(74) *Attorney, Agent, or Firm*—Woodcock Washburn LLP

(57) ABSTRACT

The invention provides a novel splice-variant of the ClC-4 protein, termed ClC-4A. ClC-4A is expressed in taste bud cells and is involved in sour taste perception. The invention provides ClC-4A polynucleotides and ClC-4A polypeptides, vectors, host cells and ClC-4A specific antibodies as well as designing high potency taste stimuli, determining taste preferences in animals, developing breed-specific foods, and modifying the taste of foods and medications.

16 Claims, 17 Drawing Sheets

```
  1 ATAGAGCCAT GATGAGAGTG AGGCATATGA GTTCTCAGTG GGAACTCCTC
 51 CAAATGGATT ACAAGAGAAA TAGTAAATTG ATTCTAAATC TGTTCCATTC
101 TCTTCCCTGT AGGATATAAA ATGTCCAGTT TTAACGCCTA AGCATGGACT
151 TTCAAACTAG CAATCACAGC GCGGGACAGA GTCACATTTT ATACAGCCAA
201 TTGAAGCACT GGGTCTCTTT GTGTTTGAAC TTAATGGCAA TTTTATTCTT
251 TAAATTCTGC ACATCTGTCT TTTCTTCAGG AAGGAATTAG TGTTTCAGGC
301 CCATCGCATG ATCTGTGTAA GATTTGTGTC ACTTGCCATT TCACTTCATC
351 TTTGCCCCTC ACTTTTCACT GAGTCATCCT CCTCCTTTTC AGTCTTACTG
401 TCATTGGGTA TCGTTGAATC ACGTATGTGC ACTTGACTGT ATGTAATAGA
451 TCCTGACAGT GCACCTAAGA AACCTGGGAC ATGGCCAGTC CAGGACTGTC
501 TCTACACTAT TGCCAGGGTT CCAAAATCTT CTGGTTTTCA TTTTCCCTCT
551 TCTTATTCTC TGTCCTCTGG CTTACTGCCT CATAGTTGTA AAATTGTTGC
601 CCAGATGCCA GGTGCGATGT CTACTTTCTG TGAGGGAAGG AGGGGGAGAG
651 GCGAGTACGA AGATGAATGT GTATATCTTT CCCAGAGATG CGCAGCATAC
701 AACCATTGGC TGGAAATCTG TTATATGCCC CATTCGCCTA GATGTCTGTA
751 AATACAGGAA GGAAAATTGT TTTAGCTATA CATTATAACA CATTACTTTC
801 TGGATGGAAT TTCGATTCTG TGGATAGGGA AGTGGGATTG GTATCTGTCA
851 TATTAAATTC CAACATCATG TCCCTGCCAT TGTTTTTTTT TTTTTTTTT
901 TTTTTT     906
```

B

>gi|11641404|ref|NM_001830.2| Homo sapiens chloride channel 4 (CLCN4), mRNA
        Length = 4562

Score =  137 bits (69), Expect = 4e-29
 Identities = 183/219 (83%), Gaps = 4/219 (1%)
 Strand = Plus / Plus

```
Query: 19   tgaggcatatgagttctcagtggggaactcctccaaatggattacaagagaaatagtaaat 78
            ||||||||||| ||| ||||| |||| ||||||||||||||||| |||||||||| ||||
Sbjct: 3678 tgaggcatatgcgttgtcagttggaatccctccaaatggattgcaagagaaatactaaat 3737

Query: 79   tgattctaaatctgttccattctcttccctgtaggatataaaatgtccagttttaacgcc 138
            ||||||||||||||||||||||  ||| |||||||||||  |||  ||||||||  || |
Sbjct: 3738 tgattctaaatctgttccattatcttctctgtaggatgcaaaacatccagttgtaatgta 3797

Query: 139  taagcatggactttcaaactagcaatcacagc---gcgggacagagtcacatttttataca 195
            |||||||| | |||| |||||||||||||||   | |||||| | | |||||| ||||||
Sbjct: 3798 taagcatgcac-ttcatactagcaatcacagcacaggaggacagcattaaatttatata 3856

Query: 196  gccaattgaagcactgggtctctttgtgtttgaacttaa 234
            |||||||  ||||||||| || ||||| ||||||||||
Sbjct: 3857 gccaatttgggcactgggcatctttgtatttgaacttaa 3895
```

Fig. 3A

```
ClC-4    CTGAAGAGAGGAGGATGATCTAGGACGCTGTCCGGGTGGACGGCCACGCCGCAAGACGCG  60
ClC-4a   CTGAAGAGAGGAGGATGATCTAGGACGCTGTCCGGGTGGACGGCCACGCCGCAAGACGCG  60
         ************************************************************

ClC-4    GCCCTGCAGGAGTGACTAGCACGGTCAGGGCGGGAGCCACGAGCGCCTCTGGGAACCTCA  120
ClC-4a   GCCCTGCA----------------------------------------------------  68
         ********

ClC-4    TGGACTTCCTCGAGGAGCCCTTCCCTGACGTGGGGACCTACGAGGACTTCCACACCATAG  180
ClC-4a   ------------------------------------------------------------

ClC-4    ACTGGCTGAGGGAAAAGTCCCGGGATACCGACAGACATAGGAAGATCACCAGCAAAAGTA  240
ClC-4a   ---------------------------------------GATCACCAGCAAAAGTA  85
                                                 ****************

ClC-4    AGGAGTCTATTTGGGAGTTCATCAAGAGCCTGCTGGACGCGTGGTCGGGATGGGTGGTGA  300
ClC-4a   AGGAGTCTATTTGGGAGTTCATCAAGAGCCTGCTGGACGCGTGGTCGGGATGGGTGGTGA  145
         ************************************************************

ClC-4    TGCTACTCATTGGGCTGCTGGCAGGTACCTTGGCTGGAGTCATCGATCTCGCTGTGGATT  360
ClC-4a   TGCTACTCATTGGGCTGCTGGCAGGTACCTTGGCTGGAGTCATCGATCTCGCTGTGGATT  205
         ************************************************************

ClC-4    GGATGACGGACCTCAAGGAGGGGGTCTGTCTGTCCGCATTCTGGTACAGCCATGAACAGT  420
ClC-4a   GGATGACGGACCTCAAGGAGGGGGTCTGTCTGTCCGCATTCTGGTACAGCCATGAACAGT  265
         ************************************************************

ClC-4    GCTGTTGGACCTCCAACGAGACCACTTTTGAGGACAGGGACAAGTGTCCCCTGTGGCAGA  480
ClC-4a   GCTGTTGGACCTCCAACGAGACCACTTTTGAGGACAGGGACAAGTGTCCCCTGTGGCAGA  325
         ************************************************************

ClC-4    AGTGGTCAGAGCTTCTTCTGAGCCAGTCAGAGGGCGCCAGCGCTTACATTCTGAATTACT  540
ClC-4a   AGTGGTCAGAGCTTCTTCTGAGCCAGTCAGAGGGCGCCAGCGCTTACATTCTGAATTACT  385
         ************************************************************

ClC-4    TAATGTACATTCTATGGGCGTTGCTGTTTGCATTTCTGGCTGTCTCCCTGGTACGTGTGT  600
ClC-4a   TAATGTACATTCTATGGGCGTTGCTGTTTGCATTTCTGGCTGTCTCCCTGGTACGTGTGT  445
         ************************************************************

ClC-4    TCGCACCGTATGCCTGTGGCTCTGGCATACCCGAGATAAAGACTATTTTGAGTGGCTTTA  660
ClC-4a   TCGCACCGTATGCCTGTGGCTCTGGCATACCCGAGATAAAGACTATTTTGAGTGGCTTTA  505
         ************************************************************

ClC-4    TCATCAGGGGATACTTGGGGAAATGGACTCTTCTAATCAAGACTGTCACCCTCGTGCTCG  720
ClC-4a   TCATCAGGGGATACTTGGGGAAATGGACTCTTCTAATCAAGACTGTCACCCTCGTGCTCG  565
         ************************************************************

ClC-4    TCGTATCCTCTGGCCTGAGCCTTGGCAAAGAGGGCCCACTGGTGCATGTGGCATGTTGCT  780
ClC-4a   TCGTATCCTCTGGCCTGAGCCTTGGCAAAGAGGGCCCACTGGTGCATGTGGCATGTTGCT  625
         ************************************************************

ClC-4    GTGGCAACTTCTTCAGCAGCCTTTTCTCCAAGTATAGCAAGAATGAAGGCAAGAGGCGTG  840
ClC-4a   GTGGCAACTTCTTCAGCAGCCTTTTCTCCAAGTATAGCAAGAATGAAGGCAAGAGGCGTG  685
         ************************************************************

ClC-4    AGGTGCTTTCAGCTGCAGCTGCTGCTGGTGTCTCTGTGGCCTTTGGTGCTCCGATAGGAG  900
ClC-4a   AGGTGCTTTCAGCTGCAGCTGCTGCTGGTGTCTCTGTGGCCTTTGGTGCTCCGATAGGAG  745
         ************************************************************

ClC-4    GTGTGCTCTTCAGTCTAGAGGAGGTCAGTTACTACTTTCCCTTGAAAACCTTGTGGAGGT  960
ClC-4a   GTGTGCTCTTCAGTCTAGAGGAGGTCAGTTACTACTTTCCCTTGAAAACCTTGTGGAGGT  805
         ************************************************************

ClC-4    CATTCTTTGCAGCCCTGGTGGCTGCCTTCACACTGCGCTCCATCAACCCCTTTGGAAATA  1020
ClC-4a   CATTCTTTGCAGCCCTGGTGGCTGCCTTCACACTGCGCTCCATCAACCCCTTTGGAAATA  865
         ************************************************************
```

Fig. 3B

```
ClC-4     GCCGCCTGGTTCTCTTTTATGTGGAGTATCATACACCCTGGTACATGGCTGAACTCTTCC 1080
ClC-4a    GCCGCCTGGTTCTCTTTTATGTGGAGTATCATACACCCTGGTACATGGCTGAACTCTTCC 925
          ************************************************************

ClC-4     CTTTCATCCTGCTTGGAGTCTTTGGGGGTTTATGGGGAACCCTCTTCACACGCTGCAACA 1140
ClC-4a    CTTTCATCCTGCTTGGAGTCTTTGGGGGTTTATGGGGAACCCTCTTCACACGCTGCAACA 985
          ************************************************************

ClC-4     TTGCTTGGTGCAGGAGGCGTAAGACCACCAGGCTGGGCAGGTACCCAGTGTTGGAGGTTA 1200
ClC-4a    TTGCTTGGTGCAGGAGGCGTAAGACCACCAGGCTGGGCAGGTACCCAGTGTTGGAGGTTA 1045
          ************************************************************

ClC-4     TTGCGGTGACAGCCGTCACCGCCATCGTGGCCTACCCCAATCCCTACACTCGCCAGAGCA 1260
ClC-4a    TTGCGGTGACAGCCGTCACCGCCATCGTGGCCTACCCCAATCCCTACACTCGCCAGAGCA 1105
          ************************************************************

ClC-4     CCAGTGAGCTCATCTCTGAGCTCTTCAACGATTGTGGGGCTCTCGAGTCTTCTCAGCTCT 1320
ClC-4a    CCAGTGAGCTCATCTCTGAGCTCTTCAACGATTGTGGGGCTCTCGAGTCTTCTCAGCTCT 1165
          ************************************************************

ClC-4     GTGACTACATCAACGACCCCAACATGACTCGGCCTGTGGATGACATTCCGGACCGGCCGG 1380
ClC-4a    GTGACTACATCAACGACCCCAACATGACTCGGCCTGTGGATGACATTCCGGACCGGCCGG 1225
          ************************************************************

ClC-4     CTGGGGTTGGAGTTTACACAGCCATGTGGCAGCTGGCCTTGGCACTGATCTTCAAAATAG 1440
ClC-4a    CTGGGGTTGGAGTTTACACAGCCATGTGGCAGCTGGCCTTGGCACTGATCTTCAAAATAG 1285
          ************************************************************

ClC-4     TCATTACTATATTTACCTTTGGCATGAAGATTCCCTCAGGTCTCTTCATCCCCAGTATGG 1500
ClC-4a    TCATTACTATATTTACCTTTGGCATGAAGATTCCCTCAGGTCTCTTCATCCCCAGTATGG 1345
          ************************************************************

ClC-4     CTGTCGGAGCCATGGCAGGCCGGATGGTGGGAATCGGTGTGGAGCAGCTGGCCTACCATC 1560
ClC-4a    CTGTCGGAGCCATGGCAGGCCGGATGGTGGGAATCGGTGTGGAGCAGCTGGCCTACCATC 1405
          ************************************************************

ClC-4     ACCATGACTGGATCATCTTCAGGAACTGGTGCAGGCCTGGAGCGGACTGTGTCACACCAG 1620
ClC-4a    ACCATGACTGGATCATCTTCAGGAACTGGTGCAGGCCTGGAGCGGACTGTGTCACACCAG 1465
          ************************************************************

ClC-4     GGCTTTATGCGATGGTGGGAGCTGCAGCCTGTCTAGGTGGGGTGACTAGGATGACAGTGT 1680
ClC-4a    GGCTTTATGCGATGGTGGGAGCTGCAGCCTGTCTAGGTGGGGTGACTAGGATGACAGTGT 1525
          ************************************************************

ClC-4     CTCTAGTGGTCATTATGTTTGAACTGACTGGAGGTCTGGAGTATATTGTACCCCTGATGG 1740
ClC-4a    CTCTAGTGGTCATTATGTTTGAACTGACTGGAGGTCTGGAGTATATTGTACCCCTGATGG 1585
          ************************************************************

ClC-4     CAGCTGCTGTCACCAGCAAGTGGGTGGCTGATGCCTTTGGGAAAGAAGGGATTTATGAAG 1800
ClC-4a    CAGCTGCTGTCACCAGCAAGTGGGTGGCTGATGCCTTTGGGAAAGAAGGGATTTATGAAG 1645
          ************************************************************

ClC-4     CCCACATCCATCTGAATGGGTACCCATTTCTTGATGTGAAGGATGAGTTCACCCACCGTA 1860
ClC-4a    CCCACATCCATCTGAATGGGTACCCATTTCTTGATGTGAAGGATGAGTTCACCCACCGTA 1705
          ************************************************************

ClC-4     CGCTGGCCACTGATGTGATGCGGCCCCGGAGGGGAGAACCGCCATTATCGGTACTAACCC 1920
ClC-4a    CGCTGGCCACTGATGTGATGCGGCCCCGGAGGGGAGAACCGCCATTATCGGTACTAACCC 1765
          ************************************************************

ClC-4     AGGACAGCATGACTGTGGAGGACGTGGAGACTCTCATCAAGGAGACAGACTACAACGGCT 1980
ClC-4a    AGGACAGCATGACTGTGGAGGACGTGGAGACTCTCATCAAGGAGACAGACTACAACGGCT 1825
          ************************************************************

ClC-4     TTCCTGTGCTCGTCTCCAGAGACTCGGAGCGTCTCATCGGGTTTGCCCAGAGGCGGGAGC 2040
ClC-4a    TTCCTGTGCTCGTCTCCAGAGACTCGGAGCGTCTCATCGGGTTTGCCCAGAGGCGGGAGC 1885
          ************************************************************
```

Fig. 3C

```
ClC-4    TAATCTTGGCTATAAAAAATGCCAGGCAGAGGCAAGAGGGCATTGTGAGCAATTCCATCA  2100
ClC-4a   TAATCTTGGCTATAAAAAATGCCAGGCAGAGGCAAGAGGGCATTGTGAGCAATTCCATCA  1945
         ************************************************************

ClC-4    TGTACTTCACAGAGGAGCCTCCTGAGCTGCCTGCCAACAGCCCACATCCACTGAAGCTGA  2160
ClC-4a   TGTACTTCACAGAGGAGCCTCCTGAGCTGCCTGCCAACAGCCCACATCCACTGAAGCTGA  2005
         ************************************************************

ClC-4    GGCGCATTTTGAACCTGAGCCCTTTCACGGTCACAGATCACACCCCCATGGAGACGGTGG  2220
ClC-4a   GGCGCATTTTGAACCTGAGCCCTTTCACGGTCACAGATCACACCCCCATGGAGACGGTGG  2065
         ************************************************************

ClC-4    TGGACATTTTCCGGAAACTGGGGCTCCGACAATGCCTGGTGACACGGAGTGGGAGACTTC  2280
ClC-4a   TGGACATTTTCCGGAAACTGGGGCTCCGACAATGCCTGGTGACACGGAGTGGGAGACTTC  2125
         ************************************************************

ClC-4    TTGGGATCATCACAAAAAAGGATGTTCTGAGACACATGGCCCAGATGGCAAACCAGGACC  2340
ClC-4a   TTGGGATCATCACAAAAAAGGATGTTCTGAGACACATGGCCCAGATGGCAAACCAGGACC  2185
         ************************************************************

ClC-4    CTGAATCCATCATGTTTAATTAGCAATAAGATGGGCATTATTTTGAGAAGATCAATAATT  2400
ClC-4a   CTGAATCCATCATGTTTAATTAGCAATAAGATGGGCATTATTTTGAGAAGATCAATAATT  2245
         ************************************************************

ClC-4    ATATCATTTTTAAAGAAATAACCAAGTGATACATTATGATCCTAA  2445
ClC-4a   ATATCATTTTTAAAGAAATAACCAAGTGATACATTATGATCCTAA  2290
         *********************************************
```

Fig. 4

```
ClC-4   MDFLEEPFPDVGTYEDFHTIDWLREKSRDTDRHRKITSKSKESIWEFIKSLLDAWSGWVV  60
ClC-4a  ------------------------------------------------------------

ClC-4   MLLIGLLAGTLAGVIDLAVDWMTDLKEGVCLSAFWYSHEQCCWTSNETTFEDRDKCPLWQ  120
ClC-4a  MLLIGLLAGTLAGVIDLAVDWMTDLKEGVCLSAFWYSHEQCCWTSNETTFEDRDKCPLWQ  60
        ************************************************************

ClC-4   KWSELLLSQSEGASAYILNYLMYILWALLFAFLAVSLVRVFAPYACGSGIPEIKTILSGF  180
ClC-4a  KWSELLLSQSEGASAYILNYLMYILWALLFAFLAVSLVRVFAPYACGSGIPEIKTILSGF  120
        ************************************************************

ClC-4   IIRGYLGKWTLLIKTVTLVLVVSSGLSLGKEGPLVHVACCCGNFFSSLFSKYSKNEGKRR  240
ClC-4a  IIRGYLGKWTLLIKTVTLVLVVSSGLSLGKEGPLVHVACCCGNFFSSLFSKYSKNEGKRR  180
        ************************************************************

ClC-4   EVLSAAAAAGVSVAFGAPIGGVLFSLEEVSYYFPLKTLWRSFFAALVAAFTLRSINPFGN  300
ClC-4a  EVLSAAAAAGVSVAFGAPIGGVLFSLEEVSYYFPLKTLWRSFFAALVAAFTLRSINPFGN  240
        ************************************************************

ClC-4   SRLVLFYVEYHTPWYMAELFPFILLGVFGGLWGTLFTRCNIAWCRRRKTTRLGRYPVLEV  360
ClC-4a  SRLVLFYVEYHTPWYMAELFPFILLGVFGGLWGTLFTRCNIAWCRRRKTTRLGRYPVLEV  300
        ************************************************************

ClC-4   IAVTAVTAIVAYPNPYTRQSTSELISELFNDCGALESSQLCDYINDPNMTRPVDDIPDRP  420
ClC-4a  IAVTAVTAIVAYPNPYTRQSTSELISELFNDCGALESSQLCDYINDPNMTRPVDDIPDRP  359
        ************************************************************

ClC-4   AGVGVYTAMWQLALALIFKIVITIFTFGMKIPSGLFIPSMAVGAMAGRMVGIGVEQLAYH  480
ClC-4a  AGVGVYTAMWQLALALIFKIVITIFTFGMKIPSGLFIPSMAVGAMAGRMVGIGVEQLAYH  419
        ************************************************************

ClC-4   HHDWIIFRNWCRPGADCVTPGLYAMVGAAACLGGVTRMTVSLVVIMFELTGGLEYIVPLM  540
ClC-4a  HHDWIIFRNWCRPGADCVTPGLYAMVGAAACLGGVTRMTVSLVVIMFELTGGLEYIVPLM  479
        ************************************************************

ClC-4   AAAVTSKWVADAFGKEGIYEAHIHLNGYPFLDVKDEFTHRTLATDVMRPRRGEPPLSVLT  600
ClC-4a  AAAVTSKWVADAFGKEGIYEAHIHLNGYPFLDVKDEFTHRTLATDVMRPRRGEPPLSVLT  539
        ************************************************************

ClC-4   QDSMTVEDVETLIKETDYNGFPVLVSRDSERLIGFAQRRELILAIKNARQRQEGIVSNSI  660
ClC-4a  QDSMTVEDVETLIKETDYNGFPVLVSRDSERLIGFAQRRELILAIKNARQRQEGIVSNSI  599
        ************************************************************

ClC-4   MYFTEEPPELPANSPHPLKLRRILNLSPFTVTDHTPMETVVDIFRKLGLRQCLVTRSGRL  720
ClC-4a  MYFTEEPPELPANSPHPLKLRRILNLSPFTVTDHTPMETVVDIFRKLGLRQCLVTRSGRL  659
        ************************************************************

ClC-4   LGIITKKDVLRHMAQMANQDPESIMFN  747
ClC-4a  LGIITKKDVLRHMAQMANQDPESIMFN  686
        **************************
```

Panel A          Panel B          Panel C

Fig. 10
A. Murine CLC-4
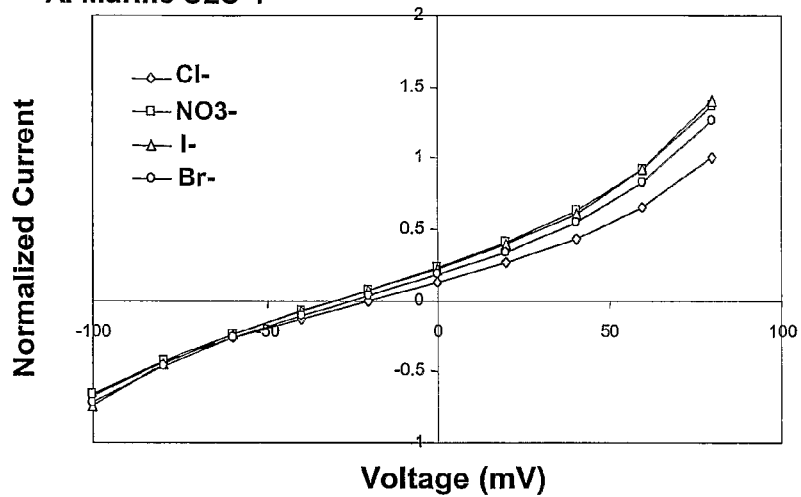
B. Murine CLC-4A
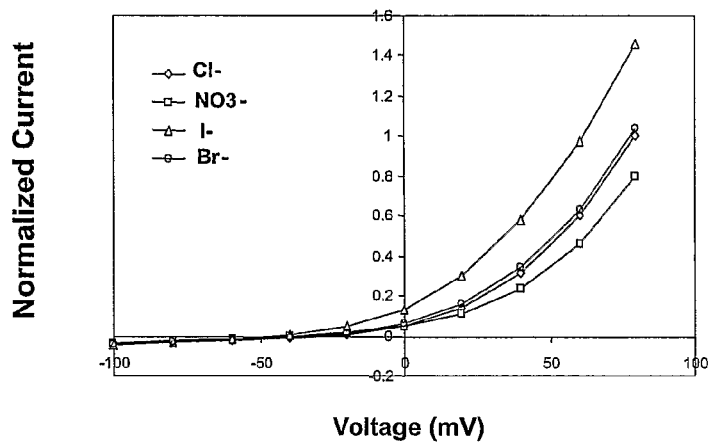
C. Human CLC-4
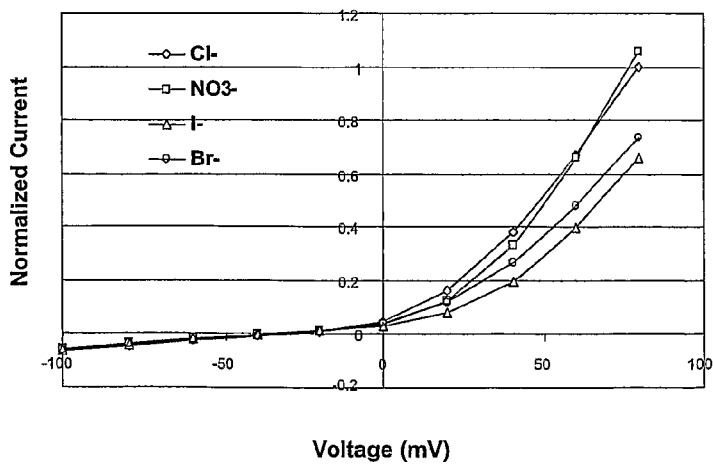

Fig. 12B
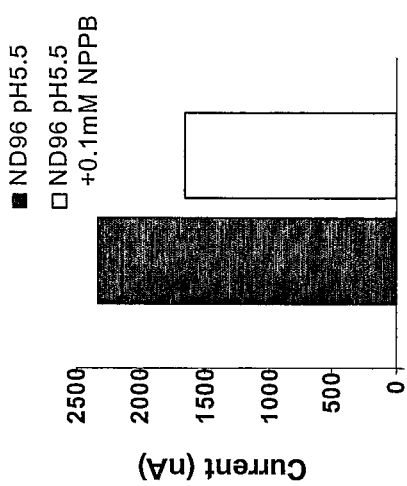
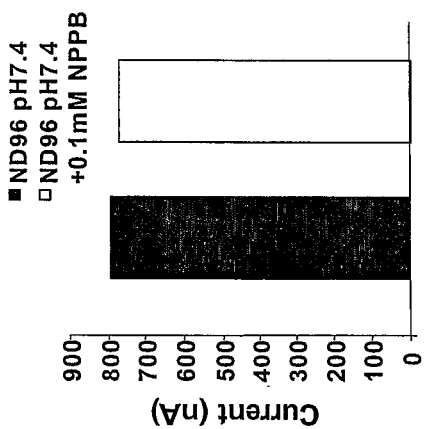
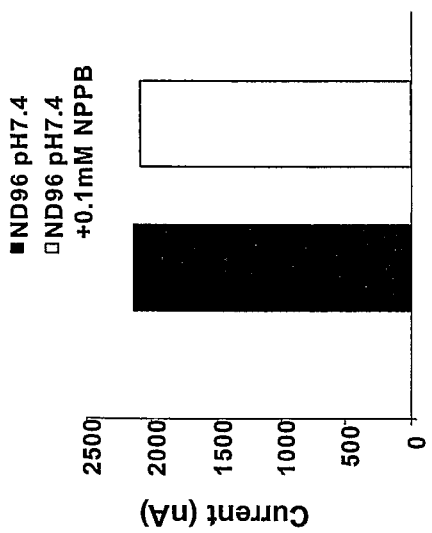

Fig. 13

```
hClC:  MLLIGLLSGSLAGLIDISAHWMTDLKEGICTGGFWFNHEHCCWNSEHVTFEERDKCPEWN 120
       MLLIGLL G LAG ID    WMTDLKEG+C  +FW++HE+CCW+S   TFE+RDKCP W+
ClC4A: MLLIGLLAGTLAGVIDLAVDWMTDLKEGVCLSAFWYSHEQCCWTSNETTFEDRDKCPLWQ  60
                            B hClC:  SWSQLIISTDEGAFAYIVNYFMYVLWALLFAFLAVSLVKVFAPYACGSGIPEIKTILSGF 180
       WS+L++S+ EGA AYI+NY MY+LWALLFAFLAVSLV+VFAPYACGSGIPEIKTILSGF
ClC4A: KWSELLLSQSEGASAYILNYLMYILWALLFAFLAVSLVRVFAPYACGSGIPEIKTILSGF 120
                                              C            D hClC:  IIRGYLGKWTLVIKTITLVLAVSSGLSLGKEGPLVHVACCCGNILCHCFNKYRKNEAKRR 240
       IIRGYLGKWTL+IKT+TLVL+VSSGLSLGKEGPLVHVACCCGN  +   F+KY KNE+KRR
ClC4A: IIRGYLGKWTLLIKTVTLVLVVSSGLSLGKEGPLVHVACCCGNFFSSLFSKYSKNEGKRR 180
                     E                        F hClC:  EVLSAAAAAGVSVAFGAPIGGVLFSLEEVSYYFPLKTLWRSFFAALVAAFTLRSINPFGN 300
       EVLSAAAAAGVSVAFGAPIGGVLFSLEEVSYYFPLKTLWRSFFAALVAAFTLRSINPFGN
ClC4A: EVLSAAAAAGVSVAFGAPIGGVLFSLEEVSYYFPLKTLWRSFFAALVAAFTLRSINPFGN 240
                 G              H                    I hClC:  SRLVLFYVEFHTPWHLFELVPFILLGIFGGLWGALFIRTNIAWCRKRKTTQLGKYPVIEV 360
       SRLVLFYVE+HTPW++ EL PFILLG+FGGLWG LF R+NIAWCR+RKTT LG+YPV+EV
ClC4A: SRLVLFYVEYHTPWYMAELFPFILLGVFGGLWGTLFTRCNIAWCRRRKTTRLGRYPVLEV 300
                                     J hClC:  LVVTAITAILAFPNEYTRMSTSELISELFNDCGLLDSSKLCDYENRFN-TSKGGELPDRP 419
       ++VTAI   +A+PN YTR+STSELISELFNDCG+L+SS+LCDY N+  N T     ++PDRP
ClC4A: IAVTAIVTAVAYPNPYTRQSTSELISELFNDCGALESSQLCDYINDPNMTRPVDDIPDRP 360
                 K              L                  * hClC:  AGVGVYSAMWQLALTLILKIVITIFTFGMKIPSGLFIPSMAVGAIAGRLLGVGMEQLAYY 479
       AGVGVY+AMWQLAL LI KIVITIFTFGMKIPSGLFIPSMAVGA+AGR++G+G+EQLAY+
ClC4A: AGVGVYTAMWQLALALIFKIVITIFTFGMKIPSGLFIPSMAVGAMAGRMVGIGVEQLAYH 420
                   M                           N hClC:  HQEWTVFNSWCSQGADCITPGLYAMVGAAACLGGVTRMTVSLVVIMFELTGGLEYIVPLM 539
       H +W +F +WC  GADC+TPGLYAMVGAAACLGGVTRMTVSLVVIMFELTGGLEYIVPLM
ClC4A: HHDWIIFRNWCRPGADCVTPGLYAMVGAAACLGGVTRMTVSLVVIMFELTGGLEYIVPLM 480
                                  O                P hClC:  AAAMTSKWVADALGREGIYDAHIRLNGYPFLEAKEEFAHKTLAMDVMKPRRNDPLLTVLT 599
       AAA+TSKWVADA+G+EGIY+AHI LNGYPFL++K+EF H+TLA DVM+PRR +P L+VLT
ClC4A: AAAVTSKWVADAFGKEGIYEAHIHLNGYPFLDVKDEFTHRTLATDVMRPRRGEPPLSVLT 540
             Q                R hClC:  QDSMTVEDVETIISETTYSGFPVVVSRESQRLVGFVLRRDLIISIENARKKQDGVVSTSI 659
       QDSMTVEDVET+I ET Y+GFPV+VSR+S+RL+GF+ RR+LI++I+NAR++Q+G+VS SI
ClC4A: QDSMTVEDVETLIKETDYNGFPVLVSRDSERLIGFAQRRELILAIKNARQRQEGIVSNSI 600
                                      CBS1 hClC:  IYFTEHSPPLPPYTPPTLKLRNILDLSPFTVTDLTPMEIVVDIFRKLGLRQCLVTHNGRL 719
       +YFTE   P LP+ +P LKLR IL+LSPFTVTD TPME VVDIFRKLGLRQCLVT +GRL
ClC4A: MYFTEEPPELPANSPHPLKLRRILNLSPFTVTDHTPMETVVDIFRKLGLRQCLVTRSGRL 660
                                                   CBS2 hClC:  LGIITKKDVLKHIAQMANQDPDSILFN 746
       LGIITKKDVL H+AQMANQDP+SI+FN
ClC4A: LGIITKKDVLRHMAQMANQDPESIMFN 687
```

US 7,785,807 B2

VOLTAGE-GATED, PH-SENSITIVE ANION CHANNEL AND ITS NOVEL SPLICE VARIANT INVOLVED IN TASTE SENSATION

CROSS-REFERENCE TO RELATED APPLICATIONS

This application is the National Stage of International Application No. PCT/US2005/045542, filed Dec. 13, 2005, which claims the benefit of U.S. Provisional Application No. 60/635,675, filed Dec. 13, 2004, the disclosure of which is incorporated herein by reference in its entirety.

STATEMENT OF GOVERNMENT INTEREST

This invention was made with government support under Grant No. DC005154 awarded by the National Institutes of Health. The government has certain rights in the invention.

FIELD OF THE INVENTION

The invention relates to a voltage-gated, pH-sensitive anion channel, polynucleotides encoding the channel, polypeptides, antibodies against the channel, transgenic animals and methods of using the same. More specifically, the invention relates to the anion channel ClC-4 and a novel splice variant of ClC-4 expressed in taste bud cells.

BACKGROUND OF THE INVENTION

The sense of taste plays an important role in the life of humans and animals. Mammals are generally thought to distinguish five primary taste qualities: sour, salty, bitter, sweet, and umami (the taste of monosodium glutamate, aspartate and some ribonucleotides). These five modalities reflect the organism's internal physiological needs. For example, salty, sweet and umami tastes enable humans and animals to seek out necessary minerals, energy- or nutrient-rich food while sour and bitter perceptions are crucial for the avoidance of putrefied foods, unripe fruits, potentially harmful plant alkaloids and other toxins. Taste stimuli can also evoke positive hedonic responses and, via the cephalic phase, initiate secretory and metabolic changes in the gut prior to food entering the stomach.

Taste sensations are mediated by specialized epithelial cells, referred to as taste receptor cells. About 50-150 taste receptor cells and supporting cells form a single taste bud. These are embedded within the epithelium of the tongue in morphologically distinct papillae or regions. Taste receptor cells utilize different receptors and signaling pathways to convey the tastes of different modalities. For example, salt taste is apparently mediated by sodium channels while sour taste may be transduced by one of several putative channels, including acid-sensing ion channels, hyperpolarization- and cyclic nucleotide-gated cation channels. In addition, electrophysiological studies suggest that chloride channels are also involved in sour taste transduction. Bitter, sweet and umami tastes are transduced by seven transmembrane receptors coupled with heterotrimeric G proteins. In addition, bitter compounds may permeate taste receptor cells and directly interact with G proteins and ion channels. Activation of receptors and ion channels by taste stimuli leads to taste cell depolarization, alteration of membrane potentials, generation of action potentials, and the triggering of neurotransmitter release onto afferent gustatory nerves, transmitting the gustatory signals to the brain.

The molecular mechanisms underlying taste transduction, especially the peripheral signal coding in the taste buds are not well understood. Molecular and genetic data indicated that subsets of taste receptor cells are responsible for bitter, sweet and umami tastes, respectively. Physiological studies showed that most taste receptor cells can be excited by stimuli representative of two or more different taste modalities. Furthermore, the molecules that are involved in generation of action potentials in taste receptor cells and in transmission of gustatory signals from taste receptor cells to afferent axons remain unknown.

Identification of proteins that respond to changes in taste cell membrane potential will allow novel insights into taste peripheral coding. The activity of some of these potential-sensitive proteins may also be pH sensitive. If so, they could represent an additional transduction process in sour taste. Possessing a more complete understanding of the activity of channel proteins will provide new targets for evaluating taste stimuli and modifiers and developing new flavors.

Currently, the molecular mechanisms underlying the transduction steps in taste, and in sour taste sensation in particular, are not fully understood. Therefore, strategies that seek to discover substances to modify tastes and to develop new flavors is based on incomplete knowledge. As a result, many potentially taste active compounds need to be taken through exhaustive and difficult animal feeding studies, or expensive human psychophysical tests. At present, the incomplete knowledge of sour taste and its interaction with other taste modalities makes rational computational design approaches difficult.

SUMMARY OF THE INVENTION

The overall objective of this invention was to discover, identify and characterize a membrane potential (voltage)-dependent, pH (sourness)-sensitive chloride channel ClC-4, and any novel isoforms that may be selective to the taste-cell. Using a PCR-based strategy, two isoforms of ClC-4 have been cloned, and characterized. One of the two isoforms, ClC-4A, appears to be taste cell-type specific. The invention further provides a means to screen compounds that can be used to modify taste and develop new flavors. In one embodiment, the channels are expressed in a heterologous cell line expression system. In another embodiment, a more stable and durable device can incorporate one or both of these channels into an active artificial support matrix. Changes in pH or membrane potential can open or close these two channels, thus regulating the flux of chloride and other anions. This movement of anions can be monitored electronically or optically, for example.

The invention provides isolated polynucleotides of comprising a splice variant of ClC-4, termed ClC-4A comprising a sequence of SEQ ID NO:6 or SEQ ID NO:11, or a sequence encoding a polypeptide having the amino acid sequence of SEQ ID NO:8. The polynucleotides may include expression vectors comprising the polynucleotide encoding ClC-4A, and the invention further provides host cells, such as mammalian cells (e.g., from humans, mice, rats, dogs, cows, pigs, cats, oxen, buffalo, llamas, sheep, horses, goats, and non-human primates) containing such expression vectors. Host cells may also be derived from non-mammals, such as, for example, frogs, birds, bacteria, yeast, insects, and nematodes. The invention also provides transgenic animals expressing the ClC-4A channel.

The invention also provides transgenic non-human animals, such as mice, rats, dogs, cows, pigs, cats, oxen, buffalo, llamas, sheep, horses, goats, and non-human primates that comprise a heterologous ClC-4A polynucleotide operably linked to expression control sequences and methods of making the same.

The invention also provides isolated ClC-4A polypeptide. In some embodiments, the ClC-4A polypeptide has the amino acid sequence of SEQ ID NO:8. In some embodiments, the ClC-4A polypeptide is a fusion protein.

The invention provides methods for identifying taste modifiers comprising contacting a ClC-4A polypeptide with a potential taste modifier and measuring the binding of the potential taste modifier to the ClC-4A polypeptide with respect to the binding of a natural ligand to ClC4-A. In some embodiments, the ClC4-A polypeptide is expressed on the surface of a host cell (e.g., *Xenopus* oocytes, human embryonic kidney cells, Chinese hamster ovary cells, HeLa cells, baby hamster kidney cells, monkey kidney cells, N1E-115 cells, and PC 12 human hepatocellular carcinoma cells) and is encoded by a nucleic acid sequence that specifically hybridizes under stringent conditions to a polynucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:10, and SEQ ID NO:11 and the polypeptide comprises as its first three amino acids, the sequence Met-Leu-Leu. In some embodiments, the potential taste modifier modulates intracellular chloride concentration. In some embodiments, the ClC-4A polypeptides are immobilized on a solid substrate.

The invention also provides a method for diagnosing a ClC-4A-related disease (i.e., excess production or insufficient production of ClC-4A in taste cells) comprising contacting a test biological sample with a polynucleotide that specifically hybridizes to a nucleic acid encoding a ClC-4A polypeptide and determining the expression level of the nucleic acid, wherein a variation from expression of the nucleic acid from a known normal biological sample indicates a ClC-4A disease state. The genetic analysis may be by any means known in the art, including, but not limited to reverse transcriptase Polymerase Chain Reaction ("rtPCR"), and northern hybridization.

The invention also provides a method for treating a ClC-4-A deficiency related disease (i.e., insufficient production of ClC-4A in taste cells) comprising administering to a subject in need of such treatment a polynucleotide encoding a ClC-4-A polypeptide operably linked to expression control sequences. In some embodiments, the polynucleotide specifically hybridizes under stringent conditions to a polynucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:10, and SEQ ID NO:11 and wherein said polynucleotide encodes a polypeptide comprising as its first three amino acids, the sequence Met-Leu-Leu. In some embodiments, the polynucleotide comprises a sequence selected from the group consisting of: SEQ ID NO:6 and SEQ ID NO:11. In some embodiments, the polynucleotide encodes a polypeptide with the amino acid sequence of SEQ ID NO:8.

The invention further provides a method for developing a food specific for a breed of animal. In some embodiments, the method comprises admixing a compound that specifically binds to a ClC-4A of the animal with a dietary preparation wherein the compound modulates the taste of the dietary preparation such that it is perceived as palatable by the breed of animal. In some embodiments, the compound blocks sour taste perception in said animal. In some embodiments, the compound binds to said ClC4-A with higher affinity than a natural ligand of ClC-4A. In some embodiments, the compound competes with a natural ligand for binding to ClC4-A.

Thus, the invention also provides dietary preparations comprising a taste modifying amount of a compound that specifically binds to a ClC4-A protein.

The invention also provides a method for modulating the taste of other orally ingested preparations, such as medicines. In some embodiments, the method for modulating the taste of a medication comprises adding a taste-modifying amount of a compound to the medication wherein said compound specifically binds to a ClC-4-A polypeptide and is perceived as palatable by a patient to which the medicine is administered. In some embodiments, the compound blocks sour taste perception in said animal. In some embodiments, the compound binds to said ClC-4-A with higher affinity than a natural ligand of ClC-4-A. In some embodiments, the compound competes with a natural ligand for binding to ClC-4-A.

The invention further provides methods for determining taste preferences in an animal by determining the relative expression of ClC-4A in the animal as compared with the expression of ClC-4, wherein higher expression of ClC-4A in the animal correlates to an increased sensitivity to sour taste and a propensity to preferring foods with high potency sweeteners.

The invention further provides a method for designing a high potency taste stimulus by determining that a test compound has high affinity for a ClC-4A polypeptide and modeling compound analogues based on the test compound. In some embodiments, the secondary compounds are screened for affinity to ClC-4A polypeptides wherein higher affinity for ClC-4A correlates to the relative potency of the secondary compound as a taste stimulus.

BRIEF DESCRIPTION OF THE DRAWINGS

FIG. 2 shows that clone GA5508 (SEQ ID NO:1) is homologous to human ClC-4 chloride channel cDNA. FIG. 2A shows the insert sequence of Clone GA5508 (SEQ ID NO:2). FIG. 2B shows a blast search against DNA databases indicating that Clone GA5508 is 83% identical to human ClC-4 cDNA (SEQ ID NO:3).

FIG. 3 shows a nucleotide sequence alignment of mouse ClC-4 and ClC-4A. The internal 155 bases are spliced out in ClC-4A (indicated as "-") and the rest of the cDNA is the same as ClC-4 (indicated as * at bottom of the alignment). The putative start codons are in bold.

FIG. 4 Amino acid sequence alignment of mouse ClC-4 and ClC-4A. The amino acid sequences of ClC-4 and ClC-4A are identical except for that ClC-4A lacks the first 60 amino acid residues of ClC-4 due to transcript splicing.

FIG. 10 shows unique ion selectivity of ClC-4 and ClC-4A. The conductance sequence of ClC-4 is $I^-=NO_3^->Br^->Cl^-$ (A) while the sequence of ClC-4A is $I^->>Br^-=Cl^->NO_3^-$ (B). These ion selectivities are quite different from those reported for the human ClC-4. To confirm our recording system, we expressed and recorded from human ClC-4, and the conductance sequence is nearly identical to the reported data: $NO_3^->Cl^->Br^->I^-$ (C), indicating that all three chloride channels tested had unique ion selectivities and that the 2% difference in amino acid sequence between human and mouse ClC-4 conferred anion selectivity.

FIG. 11 shows NFA inhibition on ion channel conductance.

FIG. 12 shows NPPB inhibition on ion channel conductance. FIG. 12A shows current-voltage curves and FIG. 12B shows corresponding bar graphs at greatest conductance. 0.1 mM NPPB had no effect on human and mouse ClC-4 conductance but inhibited ClC-4A.

FIG. 13 shows an alignment of human ClC-5 (SEQ ID NO:62) and mouse ClC-4A (SEQ ID NO:64) with conserved sequence (SEQ ID NO:63) shown between the alignments (conservative substitutions are marked with "+"). The figure also shows the relative positions of alpha helices B-R (underlined), the two CBS domains (underlined), the putative chloride selection residues (bold), and putative glycosylation site (marked by asterisk).

DETAILED DESCRIPTION OF ILLUSTRATIVE EMBODIMENTS

Figure 1:
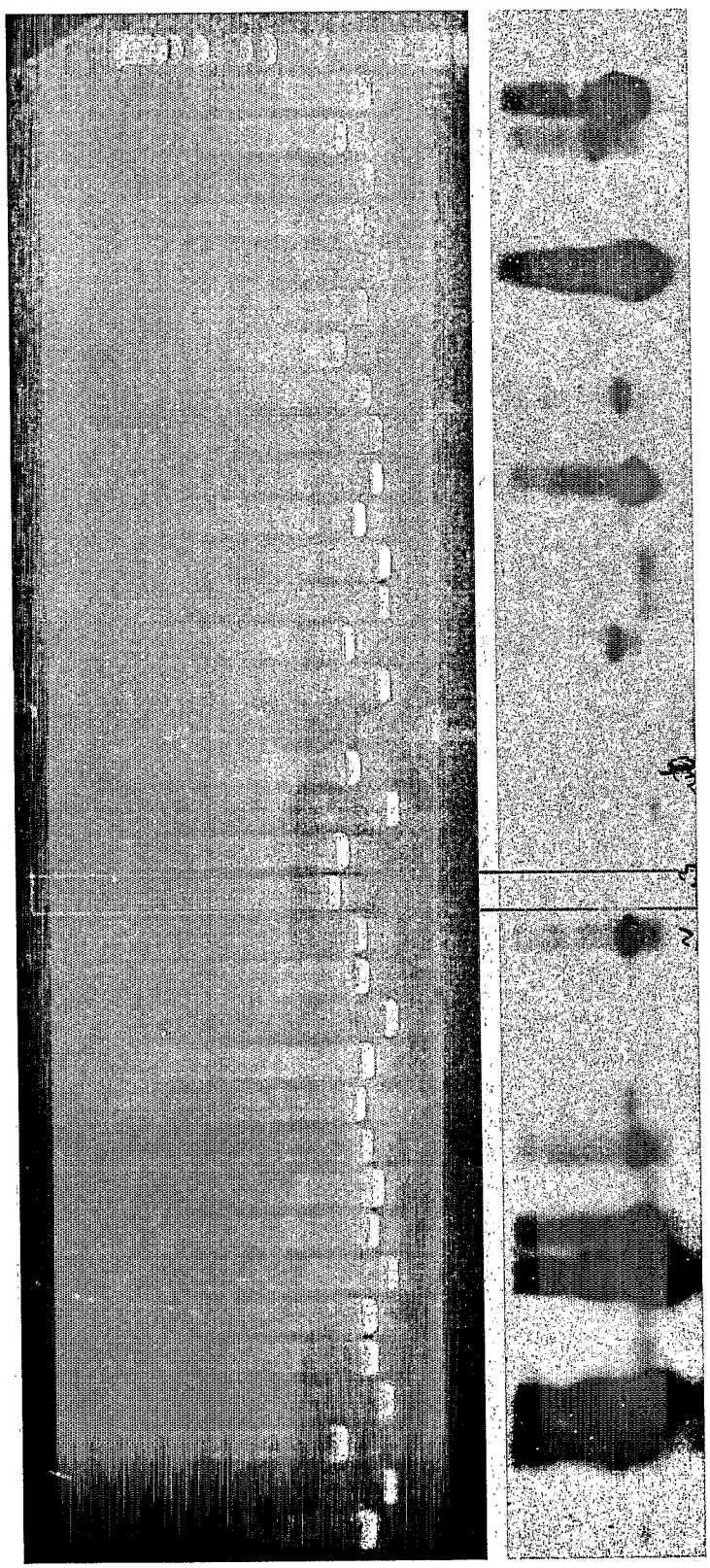
FIG. 1 shows hybridization of PCR-amplified insert DNAs from a single taste bud cell cDNA library with $^{32}$P labeled non-gustatory epithelial cDNAs. Clones that were not hybridized to the non-gustatory probes were isolated and sequenced. Boxed in the lines is Clone GA5508 that had significant similarity to the human ClC-4 cDNA.

The reference works, patents, patent applications, and scientific literature, including accession numbers to GenBank database sequences that are referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter.

Various definitions are made throughout this document. Most words have the meaning that would be attributed to those words by one skilled in the art. Words specifically defined either below or elsewhere in this document have the meaning provided in the context of the present invention as a whole and as are typically understood by those skilled in the art. Any conflict between an art-understood definition of a word or phrase and a definition of the word or phrase as specifically taught in this specification shall be resolved in favor of the latter. Headings used herein are for convenience and are not to be construed as limiting.

Standard reference works setting forth the general principles of recombinant DNA technology known to those of skill in the art include Ausubel et al., CURRENT PROTOCOLS IN MOLECULAR BIOLOGY, John Wiley & Sons, New York, 1998; Sambrook et al., MOLECULAR CLONING: A LABORATORY MANUAL, 2D ED., Cold Spring Harbor Laboratory Press, Plainview, N.Y., 1989; Kaufman et al., Eds., HANDBOOK OF MOLECULAR AND CELLULAR METHODS IN BIOLOGY AND MEDICINE, CRC Press, Boca Raton, 1995; McPherson, Ed., DIRECTED MUTAGENESIS: A PRACTICAL APPROACH, IRL Press, Oxford, 1991.

As used herein, "taste perception" refers to a response (e.g., biochemical, behavioral) or sensitivity of a ClC-4 or ClC-4A of the invention to a taste stimulus. "Taste stimulus" as used herein refers to any compound that elicits, for example at the biochemical level (e.g., activation or inhibition of a taste receptor) or behavioral level (e.g., preference, indifference, or distaste), a taste response which would be perceived by a mammal as at least one of the five taste elements, including sweet, salty, sour, bitter, and umami. "Taste perception" or "taste stimulus," or variants thereof, does not require, though it does include, transmission of a neural signal resulting in in vivo sensation of taste by a mammal. Modification of taste perception includes an alteration of (enhancement of, reduction to, or change to) a biochemical response, an ingestive response, a taste preference, or general behavior of a mammal in response to a compound.

As used herein "polynucleotide" refers to a nucleic acid molecule and includes genomic DNA, cDNA, RNA, mRNA, mixed polymers, recombinant nucleic acids, fragments and variants thereof, and the like. Polynucleotide fragments of the invention comprise at least 10, and preferably at least 12, 14, 16, 18, 20, 25, 30, 35, 40, 45, 50, 75, or 100 consecutive nucleotides of a reference polynucleotide. The polynucleotides of the invention include sense and antisense strands. The polynucleotides of the invention may be naturally occurring or non-naturally occurring polynucleotides. A "synthesized polynucleotide" as used herein refers to polynucleotides produced by purely chemical, as opposed to enzymatic, methods. "Wholly" synthesized DNA sequences are therefore produced entirely by chemical means, and "partially" synthesized DNAs embrace those wherein only portions of the resulting DNA were produced by chemical means. The polynucleotides of the invention may be single- or double-stranded. The polynucleotides of the invention may be chemically modified and may contain non-natural or derivatized nucleotide bases as will be readily appreciated by those skilled in the art. Such modifications include, for example, labels, methylation, substitution of one or more nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides, etc.), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

"Recombinant nucleic acid" is a nucleic acid generated by combination of two segments of nucleotide sequence. The combination may be, for example, by chemical means or by genetic engineering.

As used herein, "polynucleotide amplification" refers to a broad range of techniques for increasing the number of copies of specific polynucleotide sequences. Typically, amplification of either or both strand(s) of the target nucleic acid comprises the use of one or more nucleic acid-modifying enzymes, such as a DNA polymerase, ligase, RNA polymerase, or RNA-dependent reverse transcriptase. Examples of polynucleotide amplification include, but are not limited to, polymerase chain reaction (PCR), nucleic acid sequence based amplification (NASB), self-sustained sequence replication (3SR), strand displacement activation (SDA), ligase chain reaction, Qβ replicase system, and the like. A wide variety of alternative cloning and in vitro amplification methodologies are well known to those skilled in the art. Examples of these techniques are found in, for example, Berger et al., Guide to Molecular Cloning Techniques, METHODS IN ENZYMOLOGY 152, Academic Press, Inc., San Diego, Calif. (Berger), which is incorporated herein by reference in its entirety.

As used herein, the term "oligonucleotide" or "primer" refers to a series of linked nucleotide residues which has a sufficient number of bases to be used in a polymerase chain reaction (PCR). This short sequence is based on (or designed from) a genomic or cDNA sequence and is used to amplify, confirm, or reveal the presence of an identical, similar, or complementary DNA or RNA in a particular cell or tissue. Oligonucleotides comprise portions of a nucleic acid sequence having at least about 10 nucleotides and as many as about 50 nucleotides, often about 12 or 15 to about 30 nucleotides. They are chemically synthesized and may be used as probes. "Primer pair" refers to a set of primers including a 5' upstream primer that hybridizes with the 5' end of a target sequence to be amplified and a 3' downstream primer that hybridizes with the complement of the 3' end of the target sequence to be amplified.

As used herein, the term "probe" refers to nucleic acid sequences of variable length, for example between at least about 10 and as many as about 8,500 nucleotides, depending on use. Probes are used in the detection of identical, similar, or complementary target nucleic acid sequences, which target sequences may be single- or double-stranded. Longer probes are usually obtained from a natural or recombinant source, are highly specific, and are much slower to hybridize than oligomers, or shorter probes. They may be single- or double-stranded and are carefully designed to have specificity in PCR, hybridization membrane-based, or ELISA-like technologies.

As used herein, the phrase "stringent hybridization conditions" or "stringent conditions" refers to conditions under which a probe, primer, or oligonucleotide will hybridize to its target sequence, but to a minimal number of or no other sequences. Stringent conditions are sequence-dependent and will be different in different circumstances. Longer sequences will hybridize with specificity to their proper complements at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present in excess, at Tm, 50% of the probes are hybridized to their complements at equilibrium. Stringent temperature conditions will generally include temperatures in excess of 30° C., typically in excess of 37° C., and may be in excess of 45° C. Stringent salt conditions will ordinarily be less than 1.0 M, typically less than 0.5 M, and may be less than 0.2 M. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers, or oligonucleotides (e.g., 10 to 50 nucleotides) and at least about 60° C. for longer probes, primers, or oligonucleotides. Stringent conditions may also be achieved with the addition of destabilizing agents, such as formamide.

As used herein "antisense oligonucleotide" refers to a nucleic acid molecule that is complementary to at least a portion of a target nucleotide sequence of interest and specifically hybridizes to the target nucleotide sequence under physiological conditions. The term "double stranded RNA" or "dsRNA" as used herein refers to a double-stranded RNA molecule capable of RNA interference, including small interfering RNA (siRNA) (see for example, Bass, Nature, 411, 428-429 (2001); Elbashir et al., Nature, 411, 494-498 (2001)).

As used herein, the term "complementary" refers to Watson-Crick base pairing between nucleotide units of a nucleic acid molecule.

The term "marker gene" or "reporter gene" refers to a gene encoding a product that, when expressed, confers a phenotype at the physical, morphologic, or biochemical level on a transformed cell that is easily identifiable, either directly or indirectly, by standard techniques and includes, but is not limited to, genes encoding proteins that confer resistance to toxins or antibiotics such as ampicillin, neomycin, and methotrexate; genes encoding proteins that complement auxotrophic deficiencies; and genes encoding proteins that supply critical components not available from complex media. Examples of marker genes include green fluorescent protein (GFP), red fluorescent protein (DsRed), alkaline phosphatase (AP), β-lactamase, chloramphenicol acetyltransferase (CAT), adenosine deaminase (ADA), aminoglycoside phosphotransferase (NEOr, G418r) dihydrofolate reductase (DHFR), hygromycin-B-phosphotransferase (HPH), thymidine kinase (TK), lacZ (encoding β-galactosidase), β-lactamase, luciferase (luc), and xanthine guanine phosphoribosyltransferase (XGPRT). As with many of the standard procedures associated with the practice of the invention, skilled artisans will be aware of additional sequences that can serve the function of a marker or reporter. Thus, this list is merely meant to show examples of what can be used and is not meant to limit the invention.

As used herein, the term "promoter" refers to a regulatory element that regulates, controls, or drives expression of a nucleic acid molecule of interest and can be derived from sources such as from adenovirus, SV40, parvoviruses, vaccinia virus, cytomegalovirus, or mammalian genomic DNA. Examples of suitable promoters include, but are not limited to, CMV, MSH2, trp, lac, phage, and TRNA promoters. Suitable promoters that can be used in yeast include, but are not limited to, such constitutive promoters as 3-phosphoglycerate kinase and various other glycolytic enzyme gene promoters such as enolase or glyceraldehydes-3-phosphate dehydrogenase, or such inducible promoters as the alcohol dehydrogenase 2 promoter or metallothionine promoter. Again, as with many of the standard procedures associated with the practice of the invention, skilled artisans will be aware of additional promoters that can serve the function of directing the expression of a marker or reporter. Thus, the list is merely meant to show examples of what can be used and is not meant to limit the invention.

"Operably linked" refers to juxtaposition wherein the components are in a functional relationship. For example, a promoter is operably linked or connected to a coding sequence if it controls the transcription or expression of the sequence.

The terms "polypeptide," "peptide," and "protein" are used interchangeably herein. "Polypeptide" refers to a polymer of amino acids without referring to a specific length. Polypeptides of the invention include peptide fragments, derivatives, and fusion proteins. Peptide fragments preferably have at least about 10, 15, 20, 25, 30, 35, 40, 45, 50, 60, 70, 80, 90, or 100 amino acids. Some peptide fragments of the invention are biologically active. Biological activities include immunogenicity, ligand binding, and activity associated with the reference peptide. Immunogenic peptides and fragments of the invention generate an epitope-specific immune response, wherein "epitope" refers to an immunogenic determinant of a peptide and preferably contains at least three, five, eight, nine, ten, fifteen, twenty, thirty, forty, forty-five, or fifty amino acids. Some immunogenic peptides of the invention generate an immune response specific to that peptide. Polypeptides of the invention include naturally occurring and non-naturally occurring peptides. The term includes modified polypeptides (wherein examples of such modifications include glycosylation, acetylation, phosphorylation, carboxylation, ubiquitination, labeling, etc.), analogs (such as non-naturally occurring amino acids, substituted linkages, etc.), and functional mimetics. A variety of methods for labeling polypeptides are well known in the art and include radioactive isotopes such as $^{32}P$ or $^{35}S$, ligands that bind to labeled antiligands (e.g., antibodies), fluorophores, chemiluminescent agents, enzymes, and antiligands.

As used herein, the term "amino acid" denotes a molecule containing both an amino group and a carboxyl group. In some embodiments, the amino acids are $\alpha$-, $\beta$-, $\gamma$- or $\delta$-amino acids, including their stereoisomers and racemates. As used herein the term "L-amino acid" denotes an $\alpha$-amino acid having the L configuration around the $\alpha$-carbon, that is, a carboxylic acid of general formula $CH(COOH)(NH_2)$-(side chain), having the L-configuration. The term "D-amino acid" similarly denotes a carboxylic acid of general formula $CH(COOH)(NH_2)$-(side chain), having the D-configuration around the $\alpha$-carbon. Side chains of L-amino acids include naturally occurring and non-naturally occurring moieties. Non-naturally occurring (i.e., unnatural) amino acid side chains are moieties that are used in place of naturally occurring amino acid side chains in, for example, amino acid analogs. Amino acid substituents may be attached, for example, through their carbonyl groups through the oxygen or carbonyl carbon thereof, or through their amino groups, or through functionalities residing on their side chain portions.

The amino acid sequences are presented in the amino (N) to carboxy (C) direction, from left to right. The N-terminal $\alpha$-amino group and the C-terminal $\beta$-carboxy groups are not depicted in the sequence. The nucleotide sequences are presented by single strands only, in the 5' to 3' direction, from left to right. Nucleotides and amino acids are represented in the manner recommended by the IUPAC-IUB Biochemical Nomenclature Commission, or amino acids are represented by their three letters code designations.

As used herein, the term "antibody" is meant to refer to complete, intact antibodies, and Fab, Fab', F(ab)$_2$, Fv, and other fragments thereof. Complete, intact antibodies include antibodies such as polyclonal antibodies, monoclonal antibodies, chimeric antibodies, and humanized antibodies, felinized antibodies, and immunologic binding equivalents thereof. The antibodies of the invention may be labeled or unlabeled. Examples of labels of antibodies include, but are not limited to, radionuclides, enzymes, substrates, cofactors, inhibitors, fluorescent agents, chemiluminescent agents, magnetic particles, and the like. Recombinant immunoglobulins are included in the invention.

As used herein, the term "binding" means the physical or chemical interaction between two proteins or compounds or associated proteins or compounds or combinations thereof. Binding includes ionic, non-ionic, Hydrogen bonds, Van der Waals, hydrophobic interactions, etc. The physical interaction, the binding, can be either direct or indirect, indirect being through or due to the effects of another protein or compound. Direct binding refers to interactions that do not take place through or due to the effect of another protein or compound but instead are without other substantial chemical intermediates. Binding may be detected in many different manners. As a non-limiting example, the physical binding interaction between two molecules can be detected using a labeled compound. Other methods of detecting binding are well-known to those of skill in the art.

As used herein, the term "contacting" means bringing together, either directly or indirectly, a compound into physical proximity to a molecule of interest. Contacting may occur, for example, in any number of buffers, salts, solutions, or in a cell or cell extract.

As used herein, the terms "modulates" or "modifies" means an increase or decrease in the amount, quality, or effect of a particular activity or protein. "Modulators" refer to any inhibitory or activating molecules identified using in vitro and in vivo assays for, e.g., agonists, antagonists, and their homologues, including fragments, variants, and mimetics, as defined herein, that exert substantially the same biological activity as the molecule. "Inhibitors" or "antagonists" are modulating compounds that reduce, decrease, block, prevent, delay activation, inactivate, desensitize, or downregulate the biological activity or expression of a molecule or pathway of interest. "Inducers," "activators," or "agonists" are modulating compounds that increase, induce, stimulate, open, activate, facilitate, enhance activation, sensitize, or upregulate a molecule or pathway of interest. In some preferred embodiments of the invention, the level of inhibition or upregulation of the expression or biological activity of a molecule or pathway of interest refers to a decrease (inhibition or downregulation) or increase (upregulation) of greater than about 50%, 60%, 70%, 75%, 80%, 85%, 90%, 91%, 92%, 93%, 94%, 95%, 96%, 97%, 98%, or 99%. The inhibition or upregulation may be direct, i.e., operate on the molecule or pathway of interest itself, or indirect, i.e., operate on a molecule or pathway that affects the molecule or pathway of interest.

A "purified" or "substantially purified" polynucleotide or polypeptide is substantially separated from other cellular components that naturally accompany a native (or wild-type) nucleic acid or polypeptide and/or from other impurities (e.g., agarose gel). A purified polypeptide or protein will comprise about 60% to more than 99% w/w of a sample, and may be about 90%, about 95%, or about 98% pure. As used herein, the term "isolated" refers to a molecule that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules.

"About" as used herein refers to +/−10% of the reference value. As used herein, "variant" nucleotide or amino acid sequences refer to homologues, including, for example, isoforms, species variants, allelic variants, and fragments of the sequence of interest. "Homologous nucleotide sequence" or "homologous amino acid sequence," or variations thereof, refers to sequences characterized by a relative identity, at the nucleotide level with respect to a reference sequence, or homology at the amino acid level, of at least about 60%, at least about 70%, at least about 75%, at least about 80%, at least about 81%, at least about 82%, at least about 83%, at least about 84%, at least about 85%, preferably at least about 90%, at least about 95%, at least about 98%, or at least about 99%, and more preferably 100%, to a reference sequence, or portion or fragment thereof encoding or having a functional domain. The reference sequence may include, for example, but is not limited to the nucleic acid sequence of SEQ ID NO:1, SEQ ID NO:2, SEQ ID NO:3, SEQ ID NO:4, SEQ ID NO:5, SEQ ID NO:6, SEQ ID NO:10, SEQ ID NO:11, SEQ ID NO:12, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, and SEQ ID NO:36, or portions thereof which encode a functional domain of the encoded polypeptide (SEQ ID NO:9, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24) or the polypeptide having amino acid sequence SEQ ID NO:7 or SEQ ID NO:8. Functional domains of the ClC4 or ClC-4A of the invention include extracellular domains, transmembrane domains, and intracellular domains. Isoforms can be expressed in different tissues of the same organism as a result of, for example, alternative splicing of RNA. Alternatively, isoforms can be encoded by different genes. Homologous nucleotide sequences include nucleotide sequences encoding for a species variant of a protein. Homologous nucleotide sequences also include, but are not limited to, naturally occurring allelic variations and mutations of the nucleotide sequences set forth herein. Study of mutations and polymorphisms of the ClC-4 and ClC-4A receptor polynucleotide sequences may explain breed-specific and/or individual taste preferences of a mammal. The contribution of ClC-4A in taste perception may be in its interaction with other taste perceiving molecules. It is known for example that acid increases sweet taste perception and decreases salt and bitter taste perception (Sakurai N, F. Kanemura, K. Watanabe, Y. Shimizu, and K. Tonosaki (2000) "Effects of acids on neural activity elicited by other taste stimuli in the rat Chorda tympani" *Brain Res.* 859(2):369-372) and therefore, the perception of taste from mixed taste signal input may be a central event. The contribution of ClC-4A stimulators and antagonists may play an important role in central taste perception and is an important parameter to consider in the design and development of breed-specific foods and high potency taste modifiers. Homologous amino acid sequences include those amino acid sequences which encode conservative amino acid substitutions in polypeptides having an amino acid sequence of SEQ ID NO:7, SEQ ID NO:8, SEQ ID NO:9, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24 as well as in polypeptides identified according to the methods of the invention. Percent homology may be determined by, for example, the Gap program (Wisconsin Sequence Analysis Package, Version 8 for Unix, Genetics Computer Group, University Research Park, Madison Wis.), using the default settings, which uses the algorithm of Smith and Waterman (Smith and Waterman (1981) *Adv. Appl. Math.* 2:482-489). Nucleic acid fragments of the invention preferably have at least about 5, at least about 10, at least about 15, at least about 20, at least about 25, at least about 50, or at least about 100 nucleotides of the reference nucleotide sequence. The nucleic acid fragments of the invention may encode a polypeptide having at least one biological property, or function that is substantially similar to a biological property of the polypeptide encoded by the full-length nucleic acid sequence.

As is well known in the art, because of the degeneracy of the genetic code, there are numerous DNA and RNA molecules that can code for the same polypeptide as that encoded by a nucleotide sequence of interest. The present invention, therefore, contemplates those other DNA and RNA molecules which, on expression, encode a polypeptide encoded by the nucleic acid molecule of interest. DNA and RNA molecules other than those specifically disclosed herein characterized simply by a change in a codon for a particular amino acid, are within the scope of this invention.

Amino acid "insertions," "substitutions" or "deletions" are changes to or within an amino acid sequence. The variation allowed in a particular amino acid sequence may be experimentally determined by producing the peptide synthetically or by systematically making insertions, deletions, or substitutions of nucleotides in the nucleic acid sequence using recombinant DNA techniques. Alterations of the naturally occurring amino acid sequence can be accomplished by any of a number of known techniques. For example, mutations can be introduced into the polynucleotide encoding a polypeptide at particular locations by procedures well known to the skilled artisan, such as oligonucleotide-directed mutagenesis.

A polypeptide variant of the present invention may exhibit substantially the biological activity of a naturally occurring reference polypeptide. "Biological activity" as used herein refers to the level of a particular function (for example, ion conductance, ion selectivity, binding of agonist or antagonist, change in membrane potential in response to alteration of pH, inhibition by known antagonists (e.g., niflumic acid (NFA) or 5-nitro-2-(3-phenylpropylamino)-benzoic acid (NPPB)) of a molecule or pathway of interest in a biological system. Biological activity of ClC-4 and ClC-4A may be distinguished, for example by selectivity of ions. ClC4 has an ion selectivity characterized by $NO_3^->Br^->Cl^-$, while ClC-4A has an ion selectivity of $I^->>Br^-=Cl^->NO_3^-$. "Wild-type biological activity" refers to the normal level of function of a molecule or pathway of interest. "Reduced biological activity" refers to a decreased level of function of a molecule or pathway of interest relative to a reference level of biological activity of that molecule or pathway. For example, reduced biological activity may refer to a decreased level of biological activity relative to the wild-type biological activity of a molecule or pathway of interest. "Increased biological activity" refers to an increased level of function of a molecule or pathway of interest relative to a reference level of biological activity of that molecule or pathway. For example, increased biological activity may refer to an increased level of biological activity relative to the wild-type biological activity of a molecule or pathway of interest. Reference to exhibiting "substantially the biological activity of a naturally occurring polypeptide" indicates that variants within the scope of the invention can comprise conservatively substituted sequences, meaning that one or more amino acid residues of a polypeptide are replaced by different residues that do not alter the secondary and/or tertiary structure of the polypeptide. Such substitutions may include the replacement of an amino acid by a residue having similar physicochemical properties, such as substituting one aliphatic residue (Ile, Val, Leu or Ala) for another, or substitution between basic residues Lys and Arg, acidic residues Glu and Asp, amide residues Gln and Asn, hydroxyl residues Ser and Tyr, or aromatic residues Phe and Tyr. Further information regarding making phenotypically silent amino acid exchanges are known in the art (Bowie, et al. (1990) *Science* 247:1306-1310). Other polypeptide homologues which might retain substantially the biological activities of the reference polypeptide are those where amino acid substitutions have been made in areas outside functional regions of the protein. For a discussion of protein structure and correlation of structure and function of ClC-4 and ClC-4A, see sections below under "Polypeptides" and "Mimetics"). The biological activity may be assessed by, for example, measuring inhibition of conductance of ClC-4A with niflumic acid (NFA) or 5-nitro-2-(3-phenylpropylamino)-benzoic acid (NPPB). Biological activity of the polypeptides of the invention also may be determined by measuring ion conductance; ion flow; calcium imaging including with fura-2, green dextran activity, or aquorin activity; voltage measurement and/or voltage imaging with dyes or reporter genes such as β-luciferase, alkaline phosphatase, β-galactosidase, or β-lactamase; second messenger measurement, for example, IP3, cAMP, G-protein activation-based assays; or receptor phosphorylation.

A nucleotide and/or amino acid sequence of a nucleic acid molecule or polypeptide employed in the invention or of a compound identified by the screening method of the invention may be used to search a nucleotide and amino acid sequence databank for regions of similarity using Gapped BLAST (Altschul, et al. (1997) *Nucl. Acids Res.* 25:3389). Briefly, the BLAST algorithm, which stands for Basic Local Alignment Search Tool is suitable for determining sequence similarity (Altschul, et al. (1990) *J. Mol. Biol.* 215:403-410). Software or performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul, et al. (1990) *J. Mol. Biol.* 215:403-410). These initial neighborhood word hits act as seeds for initiating searches to find HSPs containing them. The word hits are extended in both directions along each sequence for as far as the cumulative alignment score can be increased. Extension for the word hits in each direction are halted when: (1) the cumulative alignment score falls off by the quantity X from its maximum achieved value; (2) the cumulative score goes to zero or below, due to the accumulation of one or more negative-scoring residue alignments; or (3) the end of either sequence is reached. The BLAST algorithm parameters W, T, and X determine the sensitivity and speed of the alignment. The BLAST program uses as defaults a word length (W) of 11, the BLOSUM62 scoring matrix (Henikoff, et al. (1992) *Proc. Natl. Acad. Sci. USA* 89:10915-10919) alignments (B) of 50, expectation (E) of 10, M=5, N=4, and a comparison of both strands. The BLAST algorithm (Karlin, et al. (1993) *Proc. Natl. Acad. Sci. USA* 90:5873-5877) and Gapped BLAST perform a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a nucleic acid is considered similar to a gene or cDNA if the smallest sum probability in comparison of the test nucleic acid to the reference nucleic acid is less than about 1, preferably less than about 0.1, more preferably less than about 0.01, and most preferably less than about 0.001.

The term "mimetic" as used herein refers to a compound that is sterically similar to a reference compound. Mimetics are structural and functional equivalents to the reference compounds.

The terms "patient" and "subject" are used interchangeably herein and include, but are not limited to amphibians, birds, dogs, cats, cattle, horses, buffalo, llama, sheep, goats, pigs, rodents, monkeys, apes, and humans. "Host cell" includes, for example, prokaryotic cells, such as bacterial cells; eukaryotic cells, such as yeast cells and animal cells, including, but not limited to invertebrate cells (e.g., insect cells and nematode cells), amphibian cells (e.g., frog cells), particularly mammalian cells (e.g., human, rodent, canine, feline, caprine, ovine, bovine, equine, porcine, simian); or plant cells. "Rodents" include, for example, rats and mice. Mammalian cell lines available as hosts for expression are known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), N1E-115 (Liles et al., (1986) *J. Biol. Chem.* 261:5307-5313), PC 12 human hepatocellular carcinoma cells (e.g., Hep G2).

The term "treatment" as used herein refers to any indicia of success of prevention, treatment, or amelioration of a disease or condition. Treatment includes any objective or subjective parameter, such as, but not limited to, abatement, remission, normalization of receptor activity, reduction in the number or severity of symptoms or side effects, or slowing of the rate of degeneration or decline of the patient. Treatment also includes a prevention of the onset of symptoms in a patient that may be at increased risk for or is suspected of having a disease or condition but does not yet experience or exhibit symptoms thereof.

As used herein, the term "compound" means any identifiable chemical or molecule, including, but not limited to a small molecule, peptide, protein, sugar, nucleotide, or nucleic acid. Such compound can be natural or synthetic.

Topologically, sensory GPCRs have an "N-terminal domain," "extracellular domains," a "transmembrane domain" comprising seven transmembrane regions, cytoplasmic, and extracellular loops, "cytoplasmic domains," and a "C-terminal domain (see, e.g., Hoon et al., Cell 96:541-551 (1999); Buck & Axel, Cell 65:175-187 (1991)). These domains can be structurally identified using methods known to those of skill in the art, such as sequence analysis programs that identify hydrophobic and hydrophilic domains (see, e.g., Stryer, Biochemistry ($3^{rd}$ ed. 1988); see also any of a number of Internet based sequence analysis programs). Such domains are useful for making chimeric proteins and for in vitro assays of the invention, e.g., ligand binding assays. In the polypeptides of the invention, the N-terminal domain is believed to be extracellular, while the C-terminal domain is believed to be cytoplasmic or intracellular.

As used herein, "bitter" refers to a basic taste characterized by solutions of such compounds as quinine, caffeine, and certain other alkaloids, that are sensed in humans primarily by taste buds at the back of the tongue, which are perceived as acrid, sharp, pungent, or harsh.

As used herein, "sweet" refers to a basic taste characterized by solutions of sugars (e.g., sucrose and glucose), alcohols, glycols, some small molecules and some amino acids that are sensed in humans primarily by taste buds on the tip of the tongue, which are perceived as agreeable or pleasing.

As used herein, "sour" refers to a basic taste characterized by solutions of vinegar and the juices of most unripe fruits and having a acid or sharp, tart, or biting taste.

As used herein, "ClC-4" and "ClC-4A" in general refers to all variants of each of these splice variants, respectively.

Polynucleotides

The invention provides purified and isolated polynucleotides (e.g., cDNA, genomic DNA, synthetic DNA, RNA, or combinations thereof, whether single- or double-stranded) that comprise a nucleotide sequence encoding the amino acid sequence of the polypeptides of the invention. Such polynucleotides are useful for recombinantly expressing the receptor and also for detecting expression of the receptor in cells (e.g., using Northern hybridization and in situ hybridization assays). Such polynucleotides also are useful in the design of antisense and other molecules for the suppression of the expression of a ClC-4 or ClC-4A channel in a cultured cell, a tissue, or an animal; for therapeutic purposes. Specifically excluded from the definition of polynucleotides of the invention are entire isolated, non-recombinant native chromosomes of host cells. Polynucleotides of the invention include the nucleotide sequences of SEQ ID NO:1, SEQ ID NO:2, SEQ ID NO:3, SEQ ID NO:4, SEQ ID NO:5, SEQ ID NO:6, SEQ ID NO:10, SEQ ID NO:11, SEQ ID NO:12, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, and SEQ ID NO:35. It will be appreciated that numerous other polynucleotide sequences exist that also encode the ClC-4 and ClC-4A receptors of the invention due to the well-known degeneracy of the universal genetic code. The polynucleotides of the invention include polynucleotides encoding and of the polypeptides of the invention.

The invention also provides a purified and isolated polynucleotide comprising a nucleotide sequence that encodes a polypeptide, wherein the polynucleotide hybridizes to a polynucleotide having a sequence of SEQ ID NO: SEQ ID NO:1, SEQ ID NO:2, SEQ ID NO:3, SEQ ID NO:4, SEQ ID NO:5, SEQ ID NO:6, SEQ ID NO:10, SEQ ID NO:11, SEQ ID NO:12, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, and SEQ ID NO:35 or the non-coding strand complementary thereto, under stringent hybridization conditions.

Genomic DNA of the invention comprises the protein-coding region for a polypeptide of the invention and is also intended to include allelic variants thereof. It is widely understood that, for many genes, genomic DNA is transcribed into RNA transcripts that undergo one or more splicing events wherein intron (i.e., non-coding regions) of the transcripts are removed, or "spliced out." RNA transcripts that can be spliced by alternative mechanisms, and therefore be subject to removal of different RNA sequences but still encode a ClC-4 polypeptide, are referred to in the art as splice variants which are embraced by the invention. Splice variants comprehended by the invention therefore are encoded by the same original genomic DNA sequences but arise from distinct mRNA transcripts. A specific splice variant of the invention is ClC-4A, which is encoded by the cDNA of SEQ ID NO:11 and which has an amino acid sequence of SEQ ID NO:8. Allelic variants are modified forms of a wild-type gene sequence, the modification resulting from recombination during chromosomal segregation or exposure to conditions which give rise to genetic mutation. Allelic variants, like wild type genes, are naturally occurring sequences (as opposed to non-naturally occurring variants that arise from in vitro manipulation).

The invention also comprehends cDNA that is obtained through reverse transcription of an RNA polynucleotide encoding a ClC-4 or ClC-4A channel (conventionally followed by second strand synthesis of a complementary strand to provide a double-stranded DNA).

One embodiment of the DNA of the invention comprises a double-stranded molecule along with the complementary molecule (the "non-coding strand" or "complement") having a sequence unambiguously deducible from the coding strand according to Watson-Crick base-pairing rules for DNA.

The present invention includes fragments of nucleotide sequences encoding a ClC-4 or ClC-4A channel comprising at least 10, and preferably at least 12, 14, 16, 18, 20, 25, 30, 35, 40, 45, 50, 75, or 100 consecutive nucleotides of a polynucleotide encoding a ClC-4 or ClC-4A channel. Fragment polynucleotides of the invention may comprise sequences unique to the ClC-4- or ClC-4A-encoding polynucleotide sequence, and therefore hybridize under highly stringent or moderately stringent conditions only (i.e., "specifically") to polynucleotides encoding a ClC-4 or ClC-4A channel (or fragments thereof). Polynucleotide fragments of genomic sequences of the invention comprise not only sequences unique to the coding region, but also include fragments of the full-length sequence derived from introns, regulatory regions, and/or other non-translated sequences. Sequences unique to polynucleotides of the invention are recognizable through sequence comparison to other known polynucleotides, and can be identified through use of alignment programs routinely utilized in the art, e.g., those made available in public sequence databases. Such sequences also are recognizable from Southern hybridization analyses to determine the number of fragments of genomic DNA to which a polynucleotide will hybridize. Polynucleotides of the invention can be labeled in a manner that permits their detection, including radioactive, fluorescent, and enzymatic labeling.

Fragment polynucleotides are particularly useful as probes for detection of full-length or fragments of ClC-4 or ClC-4A polynucleotides. One or more polynucleotides can be included in kits that are used to detect the presence of a polynucleotide encoding a ClC-4 or ClC-4A channel, or used to detect variations in a polynucleotide sequence encoding a ClC-4 or ClC-4A channel.

The invention also embraces DNAs encoding ClC-4 or ClC-4A polypeptides that hybridize under high stringency conditions to the non-coding strand, or complement, of the polynucleotides.

Exemplary highly stringent hybridization conditions are as follows: hybridization at 42° C. in a hybridization solution comprising 50% formamide, 1% SDS, 1 M NaCl, 10% Dextran sulfate, and washing twice for 30 minutes at 60° C. in a wash solution comprising 0.1×SSC and 1% SDS. It is understood in the art that conditions of equivalent stringency can be achieved through variation of temperature and buffer, or salt concentration as described, for example, in Ausubel et al. (Eds.), PROTOCOLS IN MOLECULAR BIOLOGY, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described, for example, in Sambrook et al., (Eds.), MOLECULAR CLONING: A LABORATORY MANUAL, Cold Spring Harbor Laboratory Press: Cold Spring Harbor, N.Y. (1989), pp. 9.47 to 9.51.

With the knowledge of the nucleotide sequence information disclosed in the present invention, one skilled in the art can identify and obtain nucleotide sequences which encode ClC-4 or ClC-4A channels from different sources (i.e., different tissues or different organisms) through a variety of means well known to the skilled artisan and as disclosed by, for example, Sambrook et al., MOLECULAR CLONING: A LABORATORY MANUAL, Second Edition, Cold Spring Harbor Press, Cold Spring Harbor, N.Y. (1989).

For example, DNA that encodes a ClC-4 or ClC-4A channel may be obtained by screening mRNA, cDNA, or genomic DNA with oligonucleotide probes generated from the ClC-4 or ClC-4A gene sequence information provided herein. Probes may be labeled with a detectable group, such as a fluorescent group, a radioactive atom or a chemiluminescent group in accordance with procedures known to the skilled artisan and used in conventional hybridization assays, as described by, for example, Sambrook et al.

A nucleic acid molecule comprising a ClC-4 or ClC-4A nucleotide sequence can alternatively be synthesized by use of the polymerase chain reaction (PCR) procedure, with the PCR oligonucleotide primers produced from the nucleotide sequences provided herein. The PCR reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

A wide variety of alternative cloning and in vitro amplification methodologies are well known to those skilled in the art. Examples of these techniques are found in, for example, Berger et al., "Guide to Molecular Cloning Techniques," METHODS IN ENZYMOLOGY 152, Academic Press, Inc., San Diego, Calif. (Berger), which is incorporated herein by reference in its entirety.

The polynucleotides of the invention may be used in hybridization techniques known to those skilled in the art, including but not limited to, Northern and Southern blotting and overgo hybridization. For example, polynucleotide probes of the invention may be used in tissue distribution studies and diagnostic assays.

Automated sequencing methods can be used to obtain or verify the ClC-4 or ClC-4A channel-encoding nucleotide sequence. The nucleotide sequences of the present invention are believed to be accurate. However, as is known in the art, nucleotide sequences obtained by automated methods may contain some errors. Nucleotide sequences determined by automation are typically at least about 90%, more typically at least about 95% to at least about 99.9% identical to the actual nucleotide sequence of a given nucleic acid molecule. The actual sequence may be more precisely determined using manual sequencing methods, which are well known in the art. An error in a sequence which results in an insertion or deletion of one or more nucleotides may result in a frame shift in translation such that the predicted amino acid sequence will differ from that which would be predicted from the actual nucleotide sequence of the nucleic acid molecule, starting at the point of the mutation.

The nucleic acid molecules of the present invention, and fragments derived therefrom, are useful for screening for restriction fragment length polymorphism (RFLP) associated with certain disorders, for genetic mapping, and for methods for predicting the taste perception of an organism such as a mammal involving detection of a nucleotide sequence of the invention in a biological sample of the organism. For example, an organism in which a nucleotide sequence of the invention has been identified may perceive sour compounds through the ClC-4 or ClC-4A channel.

The polynucleotide sequence information provided by the invention makes possible large-scale expression of the encoded polypeptide by techniques well known and routinely practiced in the art.

Vectors

Another aspect of the present invention is directed to vectors, or recombinant expression vectors, comprising any of the nucleic acid molecules described above. Vectors are used herein either to amplify DNA or RNA encoding a ClC-4 or ClC-4A channel and/or to express DNA which encodes a ClC-4 or ClC-4A channel. Examples of vectors include, but are not limited to, plasmids, phages, cosmids, episomes, viral particles or viruses, and integratable DNA fragments (i.e., fragments integratable into the host genome by homologous recombination). Examples of viral particles include, but are not limited to, adenoviruses, baculoviruses, parvoviruses, herpesviruses, poxviruses, adeno-associated viruses, Semliki Forest viruses, vaccinia viruses, and retroviruses. Examples of expression vectors include, but are not limited to, pcDNA3 (Invitrogen) and pSVL (Pharmacia Biotech). Other expression vectors include, but are not limited to, pSPORT™ vectors, pGEM™ vectors (Promega), pPROEXvectors™ (LTI, Bethesda, Md.), Bluescript™ vectors (Stratagene), pQE™ vectors (Qiagen), pSE420™ (Invitrogen), and pYES2™ (Invitrogen).

Expression constructs may comprise ClC-4 or ClC-4A-encoding polynucleotides operably linked to an endogenous or exogenous expression control DNA sequence and a transcription terminator. Expression control DNA sequences include promoters, enhancers, operators, and regulatory element binding sites generally, and are typically selected based on the expression systems in which the expression construct is to be utilized. Promoter and enhancer sequences are generally selected for the ability to increase gene expression, while operator sequences are generally selected for the ability to regulate gene expression. Expression constructs of the invention may also include sequences encoding one or more selectable markers that permit identification of host cells bearing the construct. Expression constructs may also include sequences that facilitate, or promote, homologous recombination in a host cell. Constructs of the invention also may include sequences necessary for replication in a host cell.

Expression constructs may be utilized for production of an encoded protein, but may also be utilized simply to amplify a ClC-4 or ClC-4A-encoding polynucleotide sequence. In some embodiments, the vector is an expression vector wherein a polynucleotide of the invention is operably linked to a polynucleotide comprising an expression control sequence. Autonomously replicating recombinant expression constructs such as plasmid and viral DNA vectors incorporating polynucleotides of the invention are also provided. Some expression vectors are replicable DNA constructs in which a DNA sequence encoding a ClC-4 or ClC-4A channel is operably linked or connected to suitable control sequence(s) capable of effecting the expression of the receptor in a suitable host. Amplification vectors do not require expression control domains, but rather need only the ability to replicate in a host, such as conferred by an origin of replication, and a selection gene to facilitate recognition of transformants. The need for control sequences in the expression vector will vary depending upon the host selected and the transformation method chosen. Control sequences include a transcriptional promoter, an optional operator sequence to control transcription, a sequence encoding suitable mRNA ribosomal binding, and sequences which control the termination of transcription and translation.

Vectors of the invention may contain a promoter that is recognized by the host organism. The promoter sequences of the present invention may be prokaryotic, eukaryotic, or viral. Examples of suitable prokaryotic sequences include the $P_R$ and $P_L$ promoters of bacteriophage lambda (THE BACTERIOPHAGE LAMBDA, Hershey, A. D., Ed., Cold Spring Harbor Press, Cold Spring Harbor, N.Y. (1973), which is incorporated herein by reference in its entirety; LAMBDA II, Hendrix, R. W., Ed., Cold Spring Harbor Press, Cold Spring Harbor, N.Y. (1980), which is incorporated herein by reference in its entirety), the trp, recA, heat shock, and lacZ promoters of *E. coli*, and the SV40 early promoter (Benoist et al. *Nature*, 1981, 290, 304-310), which is incorporated herein by reference in its entirety. Additional promoters include, but are not limited to, mouse mammary tumor virus, long terminal repeat of human immunodeficiency virus, maloney virus, cytomegalovirus immediate early promoter, Epstein Barr virus, Rous sarcoma virus, human actin, human myosin, human hemoglobin, human muscle creatine, and human metallothionein.

Additional regulatory sequences can also be included in vectors of the invention. Examples of suitable regulatory sequences are represented by the Shine-Dalgarno of the replicase gene of the phage MS-2 and of the gene cII of bacteriophage lambda. The Shine-Dalgarno sequence may be directly followed by DNA encoding a ClC-4 or ClC-4A channel, resulting in the expression of the mature protein.

Moreover, suitable expression vectors can include an appropriate marker that allows the screening of transformed host cells. The transformation of the selected host is carried out using any one of the various techniques well known to the expert in the art and described in Sambrook et al., supra.

An origin of replication or autonomously replicating sequence (ARS) can also be provided either by construction of the vector to include an exogenous origin or may be provided by the host cell chromosomal replication mechanism. If the vector is integrated into the host cell chromosome, the latter may be sufficient. Alternatively, rather than using vectors which contain viral origins of replication, one skilled in the art can transform mammalian cells by the method of co-transformation with a selectable marker and ClC-4 or ClC-4A DNA. An example of a suitable marker is dihydrofolate reductase (DHFR) or thymidine kinase (TK) (see, U.S. Pat. No. 4,399,216).

Additional regulatory sequences that may be included in the polynucleotides of the invention include secretion signals which allow the encoded polypeptide to cross and/or lodge in cell membranes, or be secreted from the cell. All regulatory sequences referred to herein that contribute to gene expression may be collectively referred to herein as "expression control sequences."

Nucleotide sequences encoding a ClC-4 or ClC-4A channel may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Sambrook et al., supra and are well known in the art. Methods for construction of mammalian expression vectors are disclosed in, for example, Okayama et al., *Mol. Cell. Biol.,* 1983, 3, 280, Cosman et al., *Mol. Immunol.,* 1986, 23, 935, Cosman et al., *Nature,* 1984, 312, 768, EP-A-0367566, and WO 91/18982, each of which is incorporated herein by reference in its entirety.

Vector of the invention are useful for expressing ClC-4 or ClC-4A in various cell systems. Overexpression of ClC-4 or ClC-4A may, for example, be useful in screening for antagonists of ClC-4 or ClC-4A as described herein. Stimulation of transcription of ClC-4 or ClC-4A polynucleotides may be used to analyze the effect of ClC-4 or ClC-4A expression on the expression of other taste receptors. Vectors may also be used to produce antisense polynucleotides that inhibit endogenous ClC-4 or ClC-4A expression to analyze the effect of a loss of the ClC-4 or ClC-4A gene.

Host Cells

According to another aspect of the invention, host cells are provided, including prokaryotic and eukaryotic cells, comprising a polynucleotide of the invention (or vector of the invention) in a manner that permits expression of the encoded ClC-4 or ClC-4A polypeptide. Polynucleotides of the invention may be introduced into the host cell as part of a circular plasmid, or as linear DNA comprising an isolated protein-coding region or a viral vector. Methods for introducing DNA into the host cell that are well known and routinely practiced in the art include transformation, transfection, electroporation, nuclear injection, or fusion with carriers such as liposomes, micelles, ghost cells, and protoplasts. Expression systems of the invention include bacterial, yeast, fungal, plant, insect, invertebrate, vertebrate, and mammalian cell systems.

The invention provides host cells that are transformed or transfected (stably or transiently) with polynucleotides of the invention or vectors of the invention. As stated above, such host cells are useful for amplifying the polynucleotides and also for expressing a ClC-4 or ClC-4A polypeptide or fragment thereof encoded by the polynucleotide.

In still another related embodiment, the invention provides a method for producing a ClC-4 or ClC-4A polypeptide (or fragment thereof) comprising the steps of growing a host cell of the invention in a nutrient medium and isolating the polypeptide or variant thereof from the cell or the medium. Because the ClC-4 or ClC-4A channel is a membrane-spanning polypeptide, it will be appreciated that, for some applications, such as certain activity assays, the preferable isolation may involve isolation of cell membranes containing the polypeptide embedded therein, whereas for other applications a more complete isolation may be preferable.

According to some aspects of the present invention, transformed host cells having an expression vector comprising any of the nucleic acid molecules described above are provided. Expression of the nucleotide sequence occurs when the expression vector is introduced into an appropriate host cell. Suitable host cells for expression of the polypeptides of the invention include, but are not limited to, prokaryotes, yeast, and eukaryotes. If a prokaryotic expression vector is employed, then the appropriate host cell would be any prokaryotic cell capable of expressing the cloned sequences. Suitable prokaryotic cells include, but are not limited to, bacteria of the genera *Escherichia, Bacillus, Salmonella, Pseudomonas, Streptomyces,* and *Staphylococcus*.

If a eukaryotic expression vector is employed, then the appropriate host cell would be any eukaryotic cell capable of expressing the cloned sequence. Eukaryotic cells may be cells of higher eukaryotes. Suitable eukaryotic cells include, but are not limited to, non-human mammalian tissue culture cells and human tissue culture cells. Host cells include, but are not limited to, insect cells, HeLa cells, Chinese hamster ovary cells (CHO cells), baby hamster kidney cells, normal dog kidney cell lines, normal cat kidney cell lines, African green monkey kidney cells (COS cells), human HEK-293 cells, and murine 3T3 fibroblasts. Propagation of such cells in cell culture has become a routine procedure (see, TISSUE CULTURE, Academic Press, Kruse and Patterson, eds. (1973), which is incorporated herein by reference in its entirety).

In addition, a yeast host may be employed as a host cell. Yeast cells include, but are not limited to, the genera *Saccharomyces, Pichia*, and *Kluveromyces*. Yeast hosts may be *S. cerevisiae* and *P. pastoris*. Yeast vectors may contain an origin of replication sequence from a 2T yeast plasmid, an autonomously replication sequence (ARS), a promoter region, sequences for polyadenylation, sequences for transcription termination, and a selectable marker gene. Shuttle vectors for replication hi both yeast and *E. coli* are also included herein.

Alternatively, insect cells may be used as host cells. In some embodiments, the polypeptides of the invention are expressed using a baculovirus expression system (see, Luckow et al., *Bio/Technology*, 1988, 6, 47; BACULOVIRUS EXPRESSION VECTORS: A LABORATORY MANUAL, O'Reilly et al (Eds.), W.H. Freeman and Company, New York, 1992; and U.S. Pat. No. 4,879,236, each of which is incorporated herein by reference in its entirety). In addition, the MAXBAC™ complete baculovirus expression system (Invitrogen) can, for example, be used for production in insect cells.

Host cells of the invention are a valuable source of immunogen for development of antibodies specifically immunoreactive with the ClC-4 or ClC-4A channel. Host cells of the invention also are useful in methods for the large-scale production of ClC-4 or ClC-4A polypeptides wherein the cells are grown in a suitable culture medium and the desired polypeptide products are isolated from the cells, or from the medium in which the cells are grown, by purification methods known in the art, e.g., conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those methods wherein the desired protein is expressed and purified as a fusion protein having a specific tag, label, or chelating moiety that is recognized by a specific binding partner or agent. The purified protein can be cleaved to yield the desired protein, or can be left as an intact fusion protein. Cleavage of the fusion component may produce a form of the desired protein having additional amino acid residues as a result of the cleavage process.

Knowledge of the ClC-4 or ClC-4A channel-encoding nucleotide sequence allows for modification of cells to permit, or increase, expression of endogenous channel. Cells can be modified (e.g., by homologous recombination) to provide increased expression by replacing, in whole or in part, the naturally occurring ClC-4 or ClC-4A promoter with all or part of a heterologous promoter so that the cells express the channel at higher or lower levels. The heterologous promoter is inserted in such a manner that it is operably linked to endogenous ClC-4 or ClC-4A coding sequence. (See, for example, PCT International Publication No. WO 94/12650, PCT International Publication No. WO 92/20808, and PCT International Publication No. WO 91/09955). It is also contemplated that, in addition to heterologous promoter DNA, amplifiable marker DNA (e.g., ada, dhfr, and the multifunctional CAD gene which encodes carbamoyl phosphate synthase, aspartate transcarbamylase, and dihydroorotase) and/or intron DNA may be inserted along with the heterologous promoter DNA. If linked to the ClC-4 or ClC-4A coding sequence, amplification of the marker DNA by standard selection methods results in co-amplification of the ClC-4 or ClC-4A coding sequences in the cells.

Knock-Out and Transplacement Animals

The DNA sequence information provided by the present invention also makes possible the development (e.g., by homologous recombination strategies; see Capecchi, *Science* 244:1288-1292 (1989), which is incorporated herein by reference) of transgenic or gene-targeted animals, including, for example, animals that fail to express functional ClC-4 or ClC-4A ("knock-out") or that express a variant thereof ("transplacement"). Such animals (especially small laboratory animals such as rats, rabbits, mice, and cats) are useful as models for studying the in vivo activities of ClC-4 or ClC-4A channels and modulators of ClC-4 or ClC-4A channels. ClC-4/ClC-4A "knockout" mice have been generated. The mutation was not lethal and the animals appear to be normal at the gross level. ClC-4 in some mouse strains is carried on the X chromosome, while in other mouse strains it is carried on an autosome. This was believed to be the first gene found to violate Ohno's law of genetics (Pahner S., J. Perry and A. Ashworth (1995) "A contravention of Ohno's law in mice" Nat. Genet. 10(4):472-476). Hybrid sterility in the two mouse strains is believed to be the result of abnormal pairing of sex chromosomes during male meiosis (Rugarli E. I. et al. (1995) "Different chromosomal localization of the Clcn4 gene in *Mus spretus* and C57BL/6J mice" *Nat. Genet*. (4):466-71).

Transgenic *Drosophila* may be produced to express any ClC-4 or ClC-4A, including those of human, by any means known in the art, for example, using the methods described in Fujioka, M. et al., (2000) "Production of Transgenic *Drosophila*" (2000) *Methods Mol. Biol*. 136:353-363.

Transgenic *Drosophila* expressing ClC-4 or ClC-4A may be used in behavioral studies to determine the activity of ClC-4 or ClC-4A alleles, variants and mutants. In some embodiments, transgenic flies may be studied for food selection based on compound selection. In other embodiments, transgenic flies may be studied for compound avoidance.

Transgenic nematodes, such as *Caenorhabditis elegans*, expressing various alleles, mutants, and portions of ClC-4 or ClC-4A, may be made using techniques known in the art. For example, but not by way of limitation, transgenic *C. elegans* may be made using protocols described in Broverman, S. M. and T. Blumenthal (1993) *Proc. Natl. Acad. Sci. USA* 90:4359-4363; Fire, A. (1986) *EMBO J*. 5:2673-2680; and Jackstadt, P. et al. (1999) *Mol. Biochem. Parasitol*. 103:261-266.

Transgenic animals for ClC-4 and ClC-4A may be made by any means known in the art.

Antisense and siRNA

Also encompassed by the invention are antisense and small interfering polynucleotides that recognize and hybridize to polynucleotides encoding ClC-4 or ClC-4A channels. Full-length and fragment antisense polynucleotides are provided. Fragment antisense molecules of the invention include (i) those that specifically recognize and hybridize to ClC-4 or ClC-4A RNA (as determined by sequence comparison of DNA encoding ClC-4 or ClC-4A channel to DNA encoding other known molecules). Identification of sequences unique to ClC-4 or ClC-4A-encoding polynucleotides can be deduced through use of any publicly available sequence database, and/or through use of commercially available sequence comparison programs. After identification of the desired sequences, isolation through restriction digestion or amplification using any of the various polymerase chain reaction techniques well known in the art can be performed. Antisense polynucleotides are particularly relevant to regulation of expression of ClC-4 or ClC-4A channel by those cells expressing ClC-4 or ClC-4A mRNA.

Antisense nucleic acids (preferably 10 to 30 base-pair oligonucleotides) capable of specifically binding to ClC-4 or ClC-4A expression control sequences or ClC-4 or ClC-4A RNA are introduced into cells (e.g., by a viral vector or colloidal dispersion system such as a liposome). The antisense nucleic acid binds to the target nucleotide sequence in the cell and prevents transcription and/or translation of the target sequence. Phosphorothioate and methylphosphonate antisense oligonucleotides are specifically contemplated for therapeutic use by the invention. Locked nucleic acids are also specifically contemplated for therapeutic use by the present invention. (See, for example, Wahlestedt et al. (2000) *Proc. Natl. Acad. Sci. USA*, 97(10):5633-5638. The antisense oligonucleotides may be further modified by adding poly-L-lysine, transferrin polylysine, or cholesterol moieties at their 5' end.

Antisense oligonucleotides, or fragments of nucleotide sequence of SEQ ID NO:1, SEQ ID NO:2, SEQ ID NO:3, SEQ ID NO:4, SEQ ID NO:5, SEQ ID NO:6, SEQ ID NO:10, SEQ ID NO:11, SEQ ID NO:12, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, and SEQ ID NO:36, or sequences complementary or homologous thereto, derived from the nucleotide sequences of the present invention encoding ClC-4 or ClC-4A channels are useful as diagnostic tools for probing gene expression in various tissues. For example, tissue can be probed in situ with oligonucleotide probes carrying detectable groups by conventional autoradiography techniques to investigate native expression of this enzyme or pathological conditions relating thereto. Antisense oligonucleotides may be directed to regulatory regions of a ClC-4 or ClC-4A nucleotide sequence, or mRNA corresponding thereto, including, but not limited to, the initiation codon, TATA box, enhancer sequences, and the like.

Those of skill in the art recognize that the antisense oligonucleotides that inhibit the expression and/or biological activity of a ClC-4 or ClC-4A channel may be predicted using any gene encoding a ClC-4 or ClC-4A channel. Specifically, antisense nucleic acid molecules comprise a sequence preferably complementary to at least about 5, 10, 15, 20, 25, 30, 35, 40, 45, 50, 100, 250 or 500 nucleotides or an entire ClC-4 or ClC-4A channel gene sequence. The antisense oligonucleotides may comprise a sequence complementary to about 15 consecutive nucleotides of the coding strand of the ClC-4 or ClC-4A channel-encoding sequence.

In one embodiment, an antisense nucleic acid molecule is antisense to a "coding region" of the coding strand of a nucleotide sequence encoding a ClC-4 or ClC-4A protein. The coding strand may also include regulatory regions of the ClC-4 or ClC-4A sequence. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding a ClC-4 or ClC-4A protein. The term "noncoding region" refers to 5' and 3' sequences which flank the coding region that are not translated into amino acids (i.e., also referred to as 5' and 3' untranslated regions (UTR)).

Antisense oligonucleotides may be directed to regulatory regions of a nucleotide sequence encoding a ClC-4 or ClC-4A protein, or mRNA corresponding thereto, including, but not limited to, the initiation codon, TATA box, enhancer sequences, and the like. Given the coding strand sequences provided herein, antisense nucleic acids of the invention can be designed according to the rules of Watson and Crick or Hoogsteen base pairing. The antisense nucleic acid molecule can be complementary to the entire coding region of a ClC-4 or ClC-4A mRNA, but also may be an oligonucleotide that is antisense to only a portion of the coding or noncoding region of the mRNA. For example, the antisense oligonucleotide can be complementary to the region surrounding the translation start site of an mRNA. An antisense oligonucleotide can be, for example, about 5, 10, 15, 20, 25, 30, 35, 40, 45 or 50 nucleotides in length.

Another means to inhibit the activity of a ClC-4 or ClC-4A channel according to the invention is via RNA interference (RNAi) (see e.g., Elbashir et al., *Nature*, 411:494-498 (2001); Elbashir et al., *Genes Development*, 15:188-200 (2001)). RNAi is the process of sequence-specific, post-transcriptional gene silencing, initiated by double-stranded RNA (dsRNA) that is homologous in sequence to the silenced gene (e.g., is homologous in sequence to the sequence encoding a ClC-4 or ClC-4A channel, for example but not limited to the sequence as set forth in SEQ ID NO:1, SEQ ID NO:2, SEQ ID NO:3, SEQ ID NO:4, SEQ ID NO:5, SEQ ID NO:6, SEQ ID NO:10, SEQ ID NO:11, SEQ ID NO:12, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, or SEQ ID NO:36). siRNA-mediated silencing is thought to occur post-transcriptionally and/or transcriptionally. For example, siRNA duplexes may mediate post-transcriptional gene silencing by reconstitution of siRNA-protein complexes (siRNPs), which guide mRNA recognition and targeted cleavage.

Accordingly, another form of a ClC-4 or ClC-4A inhibitory compound of the invention is a small interfering RNA (siRNA) directed against a ClC-4 or ClC-4A-encoding sequence. Exemplary siRNAs are siRNA duplexes (for example, 10-25, preferably 20, 21, 22, 23, 24, or 25 residues in length) having a sequence homologous or identical to a fragment of the ClC-4 or ClC-4A sequence set forth as SEQ ID NO:1, SEQ ID NO:2, SEQ ID NO:3, SEQ ID NO:4, SEQ ID NO:5, SEQ ID NO:6, SEQ ID NO:10, SEQ ID NO:11, SEQ ID NO:12, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, or SEQ ID NO:36 and having a symmetric 2-nucleotide 3'-overhang. The 2-nucleotide 3' overhang may be composed of (2'-deoxy) thymidine because it reduces costs of RNA synthesis and may enhance nuclease resistance of siRNAs in the cell culture medium and within transfected cells. Substitution of uridine by thymidine in the 3' overhang is also well tolerated in mammalian cells, and the sequence of the overhang appears not to contribute to target recognition.

Polypeptides

The invention also provides purified and isolated mammalian ClC-4 or ClC-4A channel polypeptides encoded by a polynucleotide of the invention. Some embodiments include a ClC-4 or ClC-4A polypeptide comprising the amino acid sequence of SEQ ID NO:7, SEQ ID NO:8, SEQ ID NO:9; SEQ ID NO:13, SEQ ID NO:14, SEQ ID NO:15; SEQ ID NO:16, SEQ ID NO:17, SEQ ID NO:18; SEQ ID NO:19, SEQ ID NO:20, SEQ ID NO:21; SEQ ID NO:22, SEQ ID NO:23 or SEQ ID NO:24 or fragments thereof comprising an epitope specific to the polypeptide. A reference to "epitope specific to" or "polypeptide-specific epitope," or variations thereof, indicates that a portion of the ClC-4 or ClC-4A channel or amino acid sequence is recognizable by an antibody that is specific for the ClC-4 or ClC-4A or amino acid sequence.

Included within the scope of the invention are polypeptides encoded by allelic variants of ClC-4 or ClC-4A. The allelic variants of the ClC-4 or ClC-4A channel of the invention may modify the taste perception of a mammal, to a taste stimulus. Preferably the variants have a limited number of amino acid changes. In some embodiments, there is a single amino acid change. In other embodiments 2-5 amino acids have substitutions. In other embodiments, there are up to 10 amino acid changes. In other embodiments, there are up to 15 amino acid changes. In other embodiments, there are up to 20 amino acid changes. In still other embodiments, there are up to 25 amino acid changes. In other embodiments, there are up to 30 amino acid changes or more. In some embodiments, the amino acid changes are conservative such that the function of the protein is a functional chloride channel. In other embodiments, the variant is modified such that function is lost.

The amino acid sequences of several CLC chloride channels are known and they are highly conserved. X-ray crystal structure has been determined for the CLC chloride channel of *Salmonella typhimurium* and *Escherichia coli* (Dutzler, et al. (2002) *Nature* 415:287-294). The chloride channels share 18 alpha helical structures labeled A-R, but these structures do not necessarily span the membrane (Estévez and Jentsch (2002) *Curr. Opin. Struct. Biol.* 12:531-539). The alpha helical portions of ClC-4A (SEQ ID NO:8) are defined by residues as follows B: 1-33 (SEQ ID NO:36); C: 78-100 (SEQ ID NO:37); D: 108-116 (SEQ ID NO:38); E: 125-144 (SEQ ID NO:39); F: 150-169 (SEQ ID NO:40); G: 176-193 (SEQ ID NO:41); H: 198-207 (SEQ ID NO:42); I: 217-236 (SEQ ID NO:43); J: 259-289 (SEQ ID NO:44); K: 292-311 (SEQ ID NO:45); L: 325-328 (SEQ ID NO:46); M: 378-389 (SEQ ID NO:47); N: 395-416 (SEQ ID NO:48); 0: 440-456 (SEQ ID NO:49); P: 458-470 (SEQ ID NO:50); Q: 476-493 (SEQ ID NO:51); R: 497-513 (SEQ ID NO:52). The ClC-4A protein also has two cystathionine beta synthase (CBS) domains at residues 526-586 and 624-674 of SEQ ID NO:8 (SEQ ID NO:53 and SEQ ID NO:54, respectively). ClC-4A additionally contains a conserved Asn residue at 348 which is believed to be a consensus site for glycosylation. It is conserved between human ClC-5 and mouse ClC-4A as shown in FIG. 13.

Some polymorphisms of ClC-4 and ClC-4A have been found, including a variant in which $Gln_{665}$ is replaced by a His.

Extracellular epitopes are useful for generating and screening for antibodies and other binding compounds that bind to a ClC-4 or ClC-4A channel. Thus, in another embodiment, the invention provides a purified and isolated polypeptide comprising at least one extracellular domain of the ClC-4 or ClC-4A channel. Examples of extracellular domains of the ClC-4 or ClC-4A polypeptides of the invention include residues 34-77 of ClC-4A of SEQ ID NO:8 (SEQ ID NO:55), 237-258 of SEQ ID NO:8 (SEQ ID NO:56), 329-378 of SEQ ID NO:8 (SEQ ID NO:57) and 417-439 of SEQ ID NO:8 (SEQ ID NO:58). Corresponding residues may be found for ClC-4. Intracellular portions of the ClC-4 or ClC-4A polypeptides may be important in the intracellular signaling involved in taste perception, and as such, another embodiment of the invention provides a purified and isolated polypeptide comprising at least one intracellular domain of the ClC-4 or ClC-4A channel. Examples of intracellular domains of the ClC-4 or ClC-4A polypeptides of the invention include residues 170-175 of SEQ ID NO:8 (SEQ ID NO:59), 208-216 of SEQ ID NO:8 (SEQ ID NO:60), 494-687 of SEQ ID NO:8 (SEQ ID NO:61). Corresponding residues may be found for ClC-4. Polypeptide fragments of the invention may be continuous portions of the native receptor. However, it will also be appreciated that knowledge of the ClC-4 or ClC-4A genes and protein sequences as provided herein permits recombination of various domains that are not contiguous in the native protein.

The invention embraces polypeptides that preferably have at least about 99%, at least about 95%, at least about 90%, at least about 85%, at least about 80%, at least about 75%, at least about 74%, at least about 73%, at least about 72%, at least about 71%, at least about 70%, at least about 65%, at least about 60%, at least about 55%, or at least about 50% identity and/or homology to the polypeptides of the invention, and particularly those that have substantially the same biological activity of SEQ ID NO:7 or 8.

Polypeptides of the invention may be isolated from natural cell sources or may be chemically synthesized, but are preferably produced by recombinant procedures involving host cells of the invention. Use of mammalian host cells is expected to provide for such post-translational modifications (e.g., glycosylation, truncation, lipidation, and phosphorylation) as may be needed to confer optimal biological activity on recombinant expression products of the invention.

The invention also embraces variant ClC-4 or ClC-4A polypeptides. Insertions may be located at either or both termini of the protein, or may be positioned within internal regions of the amino acid sequence. Insertional variants with additional residues at either or both termini can include, for example, fusion proteins and proteins including amino acid tags or labels. As there is an established structural/functional relationship of the chloride channels and a highly conserved amino acid sequence among family members, one can predict alterations of amino acids of the protein and the effect on the three-dimensional structure and possible functional alterations. Thus one may make alterations of the primary amino acid sequence using conservative substitutions to generate new protein homologues of ClC-4 and ClC-4A. Alternatively, one may introduce non-conservative amino acid changes to disrupt functionality of the ClC-4 or ClC-4A proteins in a targeted manner. Such mutations may be introduced to alter critical residues such as those believed to be involved in Cl⁻ selectivity are shown in bold in FIG. 13.

Insertion variants include ClC-4 or ClC-4A polypeptides wherein one or more amino acid residues are added to a biologically active fragment thereof. For example, the insertion variants of the invention include chimeric ClC-4 or ClC-4A channels wherein at least one functional domain of ClC-4 or ClC-4A channel of the invention is present.

The invention also embraces ClC-4 or ClC-4A variants having additional amino acid residues that result from use of specific expression systems. For example, use of commercially available vectors that express a desired polypeptide as part of a glutathione-S-transferase (GST) fusion product provides the desired polypeptide having an additional glycine residue at position −1 after cleavage of the GST component from the desired polypeptide. Variants that result from expression in other vector systems are also contemplated.

In another aspect, the invention provides deletion variants wherein one or more amino acid residues in a ClC-4 or ClC-4A polypeptide are removed. Deletions can be effected at one or both termini of the ClC-4 or ClC-4A polypeptide, or with removal of one or more non-terminal amino acid residues of ClC-4 or ClC-4A. Deletion variants, therefore, include all fragments of a ClC-4 or ClC-4A polypeptide.

The invention also embraces polypeptide fragments that maintain biological (e.g., ligand binding, heterodimerization, receptor activity) and/or immunological properties of a ClC-4 or ClC-4A polypeptide.

As used in the present invention, polypeptide fragments preferably comprise at least 10, 15, 20, 25, 30, 35, 40, 45, or 50 consecutive amino acids of SEQ ID NO:18, SEQ ID NO:19, SEQ ID NO:20; SEQ ID NO:21, SEQ ID NO:22, SEQ ID NO:23; SEQ ID NO:24, SEQ ID NO:25, SEQ ID NO:26; SEQ ID NO:27, or SEQ ID NO:28. Some polypeptide fragments display antigenic properties unique to, or specific for, a ClC-4 or ClC-4A channel of a given species. Fragments of the invention having the desired biological and immunological properties can be prepared by any of the methods well known and routinely practiced in the art.

In still another aspect, the invention provides substitution variants of ClC-4 or ClC-4A polypeptides. Substitution variants include those polypeptides wherein one or more amino acid residues of a ClC-4 or ClC-4A polypeptide are removed and replaced with alternative residues. In one aspect, the substitutions are conservative in nature; however, the invention embraces substitutions that are also non-conservative. Conservative substitutions for this purpose may be defined as set out in Tables 1, 2, or 3 below.

Variant polypeptides include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table 1 (from WO 97/09433, page 10, published Mar. 13, 1997 (PCT/GB96/02197, filed Sep. 6, 1996), immediately below.

TABLE 1

Conservative Substitutions I

| Side Chain Characteristic | Amino Acid |
|---|---|
| Aliphatic | G A P |
| Non-polar | I L V |
| Polar - uncharged | C S T M N Q |
| Polar - charged | D E K R |
| Aromatic | H F W Y |
| Other | N Q D E |

Alternatively, conservative amino acids can be grouped as described in Lehninger, [BIOCHEMISTRY, Second Edition; Worth Publishers, Inc. NY, N.Y. (1975), pp. 71-77] as set out in Table 2, below.

TABLE 2

Conservative Substitutions II

| SIDE CHAIN CHARACTERISTIC | AMINO ACID |
|---|---|
| Non-polar (hydrophobic) | |
| A. Aliphatic: | A I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic) | K R H |
| Negatively Charged (Acidic) | D E |

As still another alternative, exemplary conservative substitutions are set out in Table 3, below.

TABLE 3

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

It should be understood that the definition of polypeptides of the invention is intended to include polypeptides bearing modifications other than insertion, deletion, or substitution of amino acid residues. By way of example, the modifications may be covalent in nature, and include for example, chemical bonding with polymers, lipids, other organic, and inorganic moieties. Such derivatives may be prepared to increase circulating half-life of a polypeptide, or may be designed to improve the targeting capacity of the polypeptide for desired cells, tissues, or organs. Similarly, the invention further embraces ClC-4 or ClC-4A polypeptides that have been covalently modified to include one or more water-soluble polymer attachments such as polyethylene glycol, polyoxyethylene glycol, or polypropylene glycol. Variants that display ligand binding properties of native ClC-4 or ClC-4A and are expressed at higher levels, as well as variants that provide for constitutively active receptors, are particularly useful in assays of the invention.

In a related embodiment, the present invention provides compositions comprising purified polypeptides of the invention. Some compositions comprise, in addition to the polypeptide of the invention, a pharmaceutically acceptable (i.e., sterile and non-toxic) liquid, semisolid, or solid diluent that serves as a pharmaceutical vehicle, excipient, or medium. Any diluent known in the art may be used. Exemplary diluents include, but are not limited to, water, saline solutions, polyoxyethylene sorbitan monolaurate, magnesium stearate, methyl- and propylhydroxybenzoate, talc, alginates, starches, lactose, sucrose, dextrose, sorbitol, mannitol, glycerol, calcium phosphate, mineral oil, and cocoa butter.

Variants that display ligand-binding properties of native ClC-4 or ClC-4A and are expressed at higher levels, as well as variants that provide for constitutively active receptors, are particularly useful in assays of the invention; the variants are also useful in assays of the invention and in providing cellular, tissue and animal models with aberrant ClC-4 or ClC-4A activity.

Antibodies

Also included in the present invention are antibodies (e.g., monoclonal and polyclonal antibodies, single chain antibodies, chimeric antibodies, bifunctional/bispecific antibodies, humanized antibodies, human antibodies, simian antibodies, antibodies of various species including, but not limited to (dog, cat, goat, rabbit, horse, buffalo, llama, guinea pig, donkey, sheet, pig, mouse, and rat) and complementary determining region (CDR)-grafted antibodies, including compounds which include CDR sequences which specifically recognize a polypeptide of the invention) specific for a ClC-4 or ClC-4A channel of the invention or fragments thereof. Antibody fragments, including Fab, Fab', F(ab')$_2$, and F$_v$, are also provided by the invention. The term "specific for," when used to describe antibodies of the invention, indicates that the variable regions of the antibodies of the invention recognize and bind ClC-4 or ClC-4A polypeptides, preferably exclusively (i.e., are able to distinguish ClC-4 or ClC-4A polypeptides of the invention from other known polypeptides by virtue of measurable differences in binding affinity, despite the possible existence of localized sequence identity, homology, or similarity between ClC-4 or ClC-4A and such polypeptides). It will be understood that specific antibodies may also interact with other proteins (for example, S. aureus protein A or other antibodies in ELISA techniques) through interactions with sequences outside the variable region of the antibodies, and, in particular, in the constant region of the molecule. Screening assays to determine binding specificity of an antibody of the invention are well known and routinely practiced in the art. For a comprehensive discussion of such assays, see Harlow et al. (Eds.), ANTIBODIES A LABORATORY MANUAL; Cold Spring Harbor Laboratory; Cold Spring Harbor, N.Y. (1988), Chapter 6. Antibodies that recognize and bind fragments of the ClC-4 or ClC-4A polypeptides of the invention are also contemplated, provided that the antibodies are specific for ClC-4 or ClC-4A polypeptides. Antibodies of the invention can be produced using any method well known and routinely practiced in the art.

The invention provides an antibody that is specific for the ClC-4 or ClC-4A channels of the invention. Antibodies that can be generated from polypeptides that have previously been described in the literature and that are capable of fortuitously cross-reacting with ClC-4 or ClC-4A channel (e.g., due to the fortuitous existence of a similar epitope in both polypeptides) are considered "cross-reactive" antibodies. Such cross-reactive antibodies are not antibodies that are "specific" for a ClC-4 or ClC-4A channel. The determination of whether an antibody is specific for a ClC-4 or ClC-4A channel or is cross-reactive with another known receptor is made using any of several assays, such as Western blotting assays, that are well known in the art. For identifying cells that express a ClC-4 or ClC-4A channel and also for modulating ClC-4 or ClC-4A-ligand binding activity, antibodies that specifically bind to an extracellular epitope of the ClC-4 or ClC-4A channel may be used.

In some embodiments of the invention, the antibodies specifically bind ClC-4 or ClC-4A polypeptides that bind sour molecules, or block sour molecules from binding to the ClC-4 or ClC-4A polypeptides. These antibodies may also block the biological activity of the ClC-4 or ClC-4A polypeptides. In other embodiments, the antibodies preferentially bind ClC-4 or ClC-4A polypeptides of a certain species or family of ClC-4 or ClC-4A polypeptides.

In some variations, the invention provides monoclonal antibodies. Hybridomas that produce such antibodies also are intended as aspects of the invention.

In another variation, the invention provides a cell-free composition comprising polyclonal antibodies, wherein at least one of the antibodies is an antibody of the invention specific for ClC-4 or ClC-4A channel. Antiserum isolated from an animal is an exemplary composition, as is a composition comprising an antibody fraction of an antisera that has been resuspended in water or in another diluent, excipient, or carrier.

In still another related embodiment, the invention provides an anti-idiotypic antibody specific for an antibody that is specific for ClC-4 or ClC-4A channel of the invention.

It is well known that antibodies contain relatively small antigen binding domains that can be isolated chemically or by recombinant techniques. Such domains are useful ClC-4 or ClC-4A channel binding molecules themselves, and also may be reintroduced into other antibodies or fused to toxins or other polypeptides. Thus, in still another embodiment, the invention provides a polypeptide comprising a fragment of a ClC-4 or ClC-4A-specific antibody, wherein the fragment and the polypeptide bind to the ClC-4 or ClC-4A channel. By way of non-limiting example, the invention provides polypeptides that are single chain antibodies and CDR-grafted antibodies.

Antibodies of the invention are useful for, e.g., therapeutic purposes (such as by modulating activity of ClC-4 or ClC-4A channel), diagnostic purposes (such as detecting or quantitating ClC-4 or ClC-4A channel activity), for identification of compounds that may compete with the antibodies for binding to ClC-4 or ClC-4A, and also for purification of ClC-4 or ClC-4A channel. Kits comprising an antibody of the invention for any of the purposes described herein are also included within the scope of the invention. In general, a kit of the invention preferably includes a control antigen for which the antibody is immunospecific.

Methods of Identifying Ligands and Modulators

The invention also provides assays to identify compounds that bind and/or modulate ClC-4 or ClC-4A channel. A "ClC-4 or ClC-4A binding partner" is a compound that directly or indirectly binds a ClC-4 or ClC-4A polypeptide of the invention. One assay of the invention comprises the steps of: (a) contacting ClC-4 or ClC-4A channel with a compound suspected of binding ClC-4 or ClC-4A channel (the test compound); and (b) measuring binding between the compound and the ClC-4 or ClC-4A channel. In one variation, the composition comprises a cell expressing ClC-4 or ClC-4A channel on its surface. In another variation, isolated ClC-4 or ClC-4A channel or cell membranes comprising ClC-4 or ClC-4A channel are employed. The binding may be measured directly, e.g., by using a labeled compound, or may be measured indirectly. Compounds identified as binding ClC-4 or ClC-4A channel may be further tested in other assays including, but not limited to, ClC-4 or ClC-4A activity assays and/or in vivo models, in order to confirm or quantitate their activity.

Specific binding molecules, including natural ligands and synthetic compounds, can be identified or developed using isolated or recombinant ClC-4 or ClC-4A products, ClC-4 or ClC-4A variants, or preferably, cells expressing such products. Binding partners are useful for purifying ClC-4 or ClC-4A products and detection or quantification of ClC-4 or ClC-4A products in fluid and tissue samples using known immunological procedures. Binding molecules are also manifestly useful in modulating (i.e., blocking, inhibiting or stimulating) biological activities of ClC-4 or ClC-4A, especially those activities involved in signal transduction. Binding molecules also are useful in methods for predicting the taste perception of an organism such as a mammal by detecting a polypeptide of the invention in a biological sample of the organism.

The DNA and amino acid sequence information provided by the present invention also makes possible identification of binding partner compounds with which a ClC-4 or ClC-4A polypeptide or polynucleotide will interact. Methods to identify binding partner compounds include solution assays, in vitro assays wherein ClC-4 or ClC-4A polypeptides are immobilized, and cell-based assays. Identification of binding partner compounds of ClC-4 or ClC-4A polypeptides provides candidates for compounds that will be perceived as sour by the organism.

The invention includes several assay systems for identifying ClC-4 or ClC-4A-binding partners. In solution assays, methods of the invention comprise the steps of (a) contacting a ClC-4 or ClC-4A polypeptide with one or more candidate binding partner compounds and (b) identifying the compounds that bind to the ClC-4 or ClC-4A polypeptide. Identification of the compounds that bind the ClC-4 or ClC-4A polypeptide can be achieved by isolating the ClC-4 or ClC-4A polypeptide/binding partner complex, and separating the binding partner compound from the ClC-4 or ClC-4A polypeptide. An additional step of characterizing the physical, biological, and/or biochemical properties of the binding partner compound are also comprehended in another embodiment of the invention. In one aspect, the ClC-4 or ClC-4A polypeptide/binding partner complex is isolated using an antibody immunospecific for either the ClC-4 or ClC-4A polypeptide or the candidate binding partner compound.

In still other embodiments, either the ClC-4 or ClC-4A polypeptide or the candidate binding partner compound comprises a label or tag that facilitates its isolation, and methods of the invention to identify binding partner compounds include a step of isolating the ClC-4 or ClC-4A polypeptide/binding partner complex through interaction with the label or tag. An exemplary tag of this type is a poly-histidine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the invention.

In one variation of an in vitro assay, the invention provides a method comprising the steps of (a) contacting an immobilized ClC-4 or ClC-4A polypeptide with a candidate binding partner compound and (b) detecting binding of the candidate compound to the ClC-4 or ClC-4A polypeptide. In an alternative embodiment, the candidate binding partner compound is immobilized and binding of ClC-4 or ClC-4A channel is detected. Immobilization is accomplished using any of the methods well known in the art, including covalent bonding to a support, a bead, or a chromatographic resin, as well as non-covalent, high affinity interactions such as antibody binding, or use of streptavidin/biotin binding wherein the immobilized compound includes a biotin moiety. The support may, for example, be formulated into an electronic tongue or biosensor. Detection of binding can be accomplished (i) using a radioactive label on the compound that is not immobilized, (ii) using a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known and routinely practiced in the art.

The invention also provides cell-based assays to identify binding partner compounds of a ClC-4 or ClC-4A polypeptide. In one embodiment, the invention provides a method comprising the steps of contacting a ClC-4 or ClC-4A polypeptide expressed on the surface of a cell with a candidate binding partner compound and detecting binding of the candidate binding partner compound to the ClC-4 or ClC-4A polypeptide. In some embodiments, the detection comprises detecting physiological event in the cell caused by the binding of the molecule.

Another aspect of the present invention is directed to methods of identifying compounds that bind to either ClC-4 or ClC-4A channel or nucleic acid molecules encoding ClC-4 or ClC-4A channel, comprising contacting ClC-4 or ClC-4A channel, or a nucleic acid molecule encoding the same, with a compound, and determining whether the compound binds ClC-4 or ClC-4A channel or a nucleic acid molecule encoding the same. Binding can be determined by binding assays which are well known to the skilled artisan, including, but not limited to, gel-shift assays, Western blots, radiolabeled competition assay, phage-based expression cloning, co-fractionation by chromatography, co-precipitation, cross-linking, interaction trap/two-hybrid analysis, southwestern analysis, ELISA, and the like, which are described in, for example, CURRENT PROTOCOLS IN MOLECULAR BIOLOGY, 1999, John Wiley & Sons, NY, which is incorporated herein by reference in its entirety. The compounds to be screened include (which may include compounds which are suspected to bind ClC-4 or ClC-4A channel, or a nucleic acid molecule encoding the same), but are not limited to, extracellular, intracellular, biological, or chemical origin. The methods of the invention also embrace ligands, especially neuropeptides, that are attached to a label, such as a radiolabel (e.g., $^{125}$I, $^{35}$S, $^{32}$P, $^{33}$P, $^{3}$H), a fluorescence label, a chemiluminescent label, an enzymatic label, and an immunogenic label. Modulators falling within the scope of the invention include, but are not limited to, non-peptide molecules such as non-peptide mimetics, non-peptide allosteric effectors, and peptides. The ClC-4 or ClC-4A polypeptide or polynucleotide employed in such a test may either be free in solution, attached to a solid support, borne on a cell surface or located intracellularly, or associated with a portion of a cell. One skilled in the art can, for example, measure the formation of complexes between ClC-4 or ClC-4A channel and the compound being tested. Alternatively, one skilled in the art can examine the diminution in complex formation between ClC-4 or ClC-4A channel and its substrate caused by the compound being tested. In some embodiments of the invention, the recognition sites of the ClC-4 or ClC-4A channel are coupled with a monitoring system, either electrical or optical. An appropriate chemical stimulus can bind to the receptor's ligand binding domain, changing the receptor conformation to a degree that the coupled electronics or optical changes can be observed on a read-out.

In another embodiment of the invention, high throughput screening for compounds having suitable binding affinity to ClC-4 or ClC-4A channel is employed. Briefly, large numbers of different small peptide test compounds are synthesized on a solid substrate. The peptide test compounds are contacted with ClC-4 or ClC-4A channel and washed. Bound ClC-4 or ClC-4A channel is then detected by methods well known in the art. Purified polypeptides of the invention can also be coated directly onto plates for use in the aforementioned drug screening techniques. In addition, non-neutralizing antibodies can be used to capture the protein and immobilize it on the solid support.

Generally, an expressed ClC-4 or ClC-4A channel can be used for HTS binding assays in conjunction with a ligand, such as an amino acid or carbohydrate. The identified peptide is labeled with a suitable radioisotope, including, but not limited to, $^{125}$I, $^{3}$H, $^{35}$S or $^{32}$P, by methods that are well known to those skilled in the art. Alternatively, the peptides may be labeled by well-known methods with a suitable fluorescent derivative (Baindur et al. (1994) *Drug Dev. Res.*, 33:373-398; Rogers (1997) *Drug Discovery Today* 2:156-160). Radioactive ligand specifically bound to the receptor in membrane preparations made from the cell line expressing the recombinant protein can be detected in HTS assays in one of several standard ways, including filtration of the receptor-ligand complex to separate bound ligand from unbound ligand (Williams, *Med. Res. Rev.*, 1991, 11, 147-184; Sweetnam et al.

(1993) *J. Natural Products* 56: 441-455). Alternative methods include a scintillation proximity assay (SPA) or a FlashPlate format in which such separation is unnecessary (Nakayama (1998) *Cur. Opinion Drug Disc. Dev.* 1:85-91; Bossé et al (1998) *J. Biomolecular Screening* 3:285-292). Binding of fluorescent ligands can be detected in various ways, including fluorescence energy transfer (FRET), direct spectrophotofluorometric analysis of bound ligand, or fluorescence polarization (Rogers (1997) *Drug Discovery Today* 2:156-160; Hill (1998) *Cur. Opinion Drug Disc. Dev.* 1:92-97).

Other assays may be used to identify specific ligands of a ClC-4 or ClC-4A channel, including assays that identify ligands of the target protein through measuring direct binding of test ligands to the target protein, as well as assays that identify ligands of target proteins through affinity ultrafiltration with ion spray mass spectroscopy/HPLC methods or other physical and analytical methods. Alternatively, such binding interactions are evaluated indirectly using the yeast two-hybrid system described in Fields et al. (1989) *Nature* 340:245-246, and Fields et al. (1994) *Trends in Genetics* 10:286-292, both of which are incorporated herein by reference. The two-hybrid system is a genetic assay for detecting interactions between two proteins or polypeptides. It can be used to identify proteins that bind to a known protein of interest, or to delineate domains or residues critical for an interaction. Variations on this methodology have been developed to clone genes that encode DNA binding proteins, to identify peptides that bind to a protein, and to screen for drugs. The two-hybrid system exploits the ability of a pair of interacting proteins to bring a transcription activation domain into close proximity with a DNA binding domain that binds to an upstream activation sequence (UAS) of a reporter gene, and is generally performed in yeast. The assay requires the construction of two hybrid genes encoding (1) a DNA-binding domain that is fused to a first protein and (2) an activation domain fused to a second protein. The DNA-binding domain targets the first hybrid protein to the UAS of the reporter gene; however, because most proteins lack an activation domain, this DNA-binding hybrid protein does not activate transcription of the reporter gene. The second hybrid protein, which contains the activation domain, cannot by itself activate expression of the reporter gene because it does not bind the UAS. However, when both hybrid proteins are present, the noncovalent interaction of the first and second proteins tethers the activation domain to the UAS, activating transcription of the reporter gene. For example, when the first protein is a receptor, or fragment thereof, that is known to interact with another protein or nucleic acid, this assay can be used to detect agents that interfere with the binding interaction. Expression of the reporter gene is monitored as different test agents are added to the system. The presence of an inhibitory agent results in lack of a reporter signal.

The yeast two-hybrid assay can also be used to identify proteins that bind to the gene product. In an assay to identify proteins that bind to a ClC-4 or ClC-4A channel, or fragment thereof, a fusion polynucleotide encoding both a ClC-4 or ClC-4A channel (or fragment) and a UAS binding domain (i.e., a first protein) may be used. In addition, a large number of hybrid genes each encoding a different second protein fused to an activation domain are produced and screened in the assay. Typically, the second protein is encoded by one or more members of a total cDNA or genomic DNA fusion library, with each second protein-coding region being fused to the activation domain. This system is applicable to a wide variety of proteins, and it is not necessary to know the identity or function of the second binding protein. The system is highly sensitive and can detect interactions not revealed by other methods; even transient interactions may trigger transcription to produce a stable mRNA that can be repeatedly translated to yield the reporter protein.

Other assays may be used to search for agents that bind to the target protein. One such screening method to identify direct binding of test ligands to a target protein is described in U.S. Pat. No. 5,585,277, incorporated herein by reference. This method relies on the principle that proteins generally exist as a mixture of folded and unfolded states, and continually alternate between the two states. When a test ligand binds to the folded form of a target protein (i.e., when the test ligand is a ligand of the target protein), the target protein molecule bound by the ligand remains in its folded state. Thus, the folded target protein is present to a greater extent in the presence of a test ligand which binds the target protein, than in the absence of a ligand. Binding of the ligand to the target protein can be determined by any method that distinguishes between the folded and unfolded states of the target protein. The function of the target protein need not be known in order for this assay to be performed. Virtually any agent can be assessed by this method as a test ligand, including, but not limited to, metals, polypeptides, proteins, lipids, polysaccharides, polynucleotides and small organic molecules.

Another method for identifying ligands of a target protein is described in Wieboldt et al. 91997) *Anal. Chem.* 69:1683-1691, incorporated herein by reference. This technique screens combinatorial libraries of 20-30 agents at a time in solution phase for binding to the target protein. Agents that bind to the target protein are separated from other library components by simple membrane washing. The specifically selected molecules that are retained on the filter are subsequently liberated from the target protein and analyzed by HPLC and pneumatically assisted electrospray (ion spray) ionization mass spectroscopy. This procedure selects library components with the greatest affinity for the target protein, and is particularly useful for small molecule libraries.

Other embodiments of the invention comprise using competitive screening assays in which neutralizing antibodies capable of binding a polypeptide of the invention specifically compete with a test compound for binding to the polypeptide. In this manner, the antibodies can be used to detect the presence of any peptide that shares one or more antigenic determinants with ClC-4 or ClC-4A channel. Radiolabeled competitive binding studies are described in A. H. Lin et al., (1997) *Antimicrobial Agents and Chemotherapy* 41(10): 2127-2131, the disclosure of which is incorporated herein by reference in its entirety.

Another aspect of the present invention is directed to methods of identifying compounds that modulate (i.e., increase or decrease) activity of ClC-4 or ClC-4A channel comprising contacting ClC-4 or ClC-4A channel with a compound, and determining whether the compound modifies activity of ClC-4 or ClC-4A channel. The activity in the presence of the test compound is compared to the activity in the absence of the test compound. Where the activity of the sample containing the test compound is higher than the activity in the sample lacking the test compound, the compound is an agonist. Similarly, where the activity of the sample containing the test compound is lower than the activity in the sample lacking the test compound, the compound is an antagonist. In certain embodiments of the invention, the ClC-4 or ClC-4A channel has the biological activity of SEQ ID NO:16. That is, the ClC-4 or ClC-4A can sense sour compounds. Thus, agonists of such ClC-4 or ClC-4A polypeptides will perceive the agonists as sour.

Agents that modulate (i.e., increase, decrease, or block) ClC-4 or ClC-4A channel activity or expression also may be identified, for example, by incubating a putative modulator with a cell containing a ClC-4 or ClC-4A polypeptide or polynucleotide and determining the effect of the putative modulator on ClC-4 or ClC-4A channel activity or expression. The selectivity of a compound that modulates the activity of ClC-4 or ClC-4A channel can be evaluated by comparing its effects on ClC-4 or ClC-4A channel to its effect on other taste receptors. Selective modulators may include, for example, antibodies and other proteins, peptides, or organic molecules that specifically bind to a ClC-4 or ClC-4A polypeptide or a ClC-4 or ClC-4A channel-encoding nucleic acid. Compounds identified as modulating ClC-4 or ClC-4A channel activity may be further tested in other assays including, but not limited to, in vivo models, in order to confirm or quantitate their activity.

The invention also provides methods for identifying a ClC-4 or ClC-4A channel modulator by: (a) contacting a ClC-4 or ClC-4A channel binding partner and a composition comprising a ClC-4 or ClC-4A channel in the presence and in the absence of a putative modulator compound; (b) detecting binding between the binding partner and the ClC-4 or ClC-4A channel; and (c) identifying a putative modulator compound or a modulator compound in view of decreased or increased binding between the binding partner and the ClC-4 or ClC-4A channel in the presence of the putative modulator, as compared to binding in the absence of the putative modulator. Compounds identified as modulators of binding between ClC-4 or ClC-4A channel and a ClC-4 or ClC-4A binding partner may be further tested in other assays including, but not limited to, in vivo models, in order to confirm or quantitate their activity.

The invention also includes within its scope high-throughput screening (HTS) assays to identify compounds that interact with, enhance, or inhibit biological activity (i.e., affect enzymatic activity, binding activity, signal transduction, etc.) of a ClC-4 or ClC-4A polypeptide. HTS assays permit screening of large numbers of compounds in an efficient manner. Cell-based HTS systems are contemplated to investigate ClC-4 or ClC-4A channel-ligand interaction. HTS assays are designed to identify "hits" or "lead compounds" having the desired property, from which modifications can be designed to improve the desired property. Chemical modification of the "hit" or "lead compound" is often based on an identifiable structure/activity relationship between the "hit" and the ClC-4 or ClC-4A polypeptide.

For example, modulators of ClC-4 or ClC-4A channel activity may be identified by expressing the ClC-4 or ClC-4A channel in a heterologous cultured mammalian cell line, such as HEK cells, and detecting receptor activity in the presence and absence of a test compound by monitoring changes in intracellular calcium using a calcium-specific intracellular dye. In another embodiment, this process may be automated using a high-throughput screening device. In some embodiments, analysis of stimulation of ClC-4 or ClC-4A channels and receptor heterodimers may be performed using the FLIPR® assay as described by the manufacturer (Molecular Devices Corp.).

Candidate modulators contemplated by the invention include compounds selected from libraries of either potential activators or potential inhibitors. There are a number of different libraries used for the identification of small molecule modulators, including: (1) chemical libraries, (2) natural product libraries, and (3) combinatorial libraries comprised of random peptides, oligonucleotides, or organic molecules. Chemical libraries consist of random chemical structures, some of which are analogs of known compounds or analogs of compounds that have been identified as "hits" or "leads" in other drug discovery screens, some of which are derived from natural products, and some of which arise from non-directed synthetic organic chemistry. Natural product libraries are collections of microorganisms, animals, plants, or marine organisms that are used to create mixtures for screening by: (1) fermentation and extraction of broths from soil, plant, or marine microorganisms or (2) extraction of plants or marine organisms. Natural product libraries include polyketides, non-ribosomal peptides, and variants (non-naturally occurring) thereof. For a review, see *Science* 282:63-68 (1998). Combinatorial libraries are composed of large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.* 8:701-707 (1997). Identification of modulators through use of the various libraries described herein permits modification of the candidate "hit" (or "lead") to optimize the capacity of the "hit" to modulate activity.

ClC-4 or ClC-4A channel binding partners that stimulate ClC-4 or ClC-4A channel activity are useful as agonists for conditions characterized by insufficient ClC-4 or ClC-4A channel signaling (e.g., as a result of insufficient activity of a ClC-4 or ClC-4A channel ligand). ClC-4 or ClC-4A channel binding partners that block ligand-mediated ClC-4 or ClC-4A channel signaling are useful as ClC-4 or ClC-4A channel antagonists to modify excessive ClC-4 or ClC-4A channel signaling. In addition ClC-4 or ClC-4A channel modulators in general, as well as ClC-4 or ClC-4A channel encoding polynucleotides and polypeptides, are useful in diagnostic.

Mimetics

Mimetics or mimics of compounds identified herein (sterically similar compounds formulated to mimic the key portions of the structure) may be designed for pharmaceutical use. Mimetics may be used in the same manner as the compounds identified by the present invention that modulate the ClC-4 or ClC-4A channel and hence are also functional equivalents. The generation of a structural-functional equivalent may be achieved by the techniques of modeling and chemical design known to those of skill in the art. It will be understood that all such sterically similar constructs fall within the scope of the present invention.

The design of mimetics to a known pharmaceutically active compound is a known approach to the development of pharmaceuticals based on a "lead" compound. This is desirable where, for example, the active compound is difficult or expensive to synthesize, or where it is unsuitable for a particular method of administration, e.g., some peptides may be unsuitable active agents for oral compositions as they tend to be quickly degraded by proteases in the alimentary canal.

There are several steps commonly taken in the design of a mimetic. First, the particular parts of the compound that are critical and/or important in determining its ClC-4 or ClC-4A-modulating properties are determined. In the case of a polypeptide, this can be done by systematically varying the amino acid residues in the peptide, e.g. by substituting each residue in turn. Alanine scans of peptides are commonly used to refine such peptide motifs.

Once the active region of the compound has been identified, its structure is modeled according to its physical properties, e.g. stereochemistry, bonding, size, and/or charge, using data from a range of sources, such as, but not limited to, spectroscopic techniques, X-ray diffraction data, and NMR. Computational analysis, similarity mapping (which models the charge and/or volume of the active region, rather than the bonding between atoms), and other techniques known to those of skill in the art can be used in this modeling process.

In a variant of this approach, the three-dimensional structure of the compound that modulates a ClC-4 or ClC-4A channel and the active region of the ClC-4 or ClC-4A channel are modeled. This can be especially useful where either or both of these compounds change conformation upon binding. Knowledge of the structure of the ligand-binding domain the receptor also allows the design of high potency ligands and/or modulators.

A template molecule is then selected onto which chemical groups that mimic the ClC-4 or ClC-4A modulator can be grafted. The template molecule and the chemical groups grafted onto it can conveniently be selected so that the mimetic is easy to synthesize, is pharmacologically acceptable, and does not degrade in vivo, while retaining the biological activity of the lead compound. Alternatively, where the mimetic is peptide-based, further stability can be achieved by cyclizing the peptide, thereby increasing its rigidity. The mimetic or mimetics found by this approach can then be screened by the methods of the present invention to see whether they have the ability to modulate the ClC-4 or ClC-4A channel. Further optimization or modification can then be performed to arrive at one or more final mimetics for in vivo or clinical testing.

Molecular modeling for ClC-4A may be accomplished by aligning the ClC-4A sequence with other known members of the ClC chloride channel family such as those provided in Dutzler et al. (2002) *Nature* 415:287-294. In that study, Dutzler describes the x-ray structure of the ClC chloride channel and correlates the structure with the function of the protein by establishing a physical and chemical basis of the anion selectivity of the protein. Dutzler noted that all ClC chloride channels exhibit sequence conservation throughout, indicating conservation of their three-dimensional structure (Dutzler at page 289). Dutzler further states that given the sequence conservation, together with what is known about ion selectivity in a ClC chloride channel from *Escherichia coli*, one can be certain that a common set of ion selectivity principles applies to the entire family (Dutzler a 389). Thus, molecular modeling for agonists and antagonists of ClC-4A is possible as the sequence of the protein is well conserved and is correlated with a particular known structure and function. Conservative substitutions and non conservative substitutions may be made in the protein an modeled for observation of any change in structure. This approach is also useful for making mutations of ClC-4A to develop new proteins that may have different abilities to sense molecules (either enhanced or diminished, for example).

In Estévez, R. and T. J. Jentsch (2002) "CLC chloride channels: correlating structure with function" *Curr. Opin. Struct. Biol.* 12:531-539, the authors review the advances in bacterial chloride channel crystallization of Dutzler et al. and discuss the structures of chloride channels in higher organisms. From this information, the structure of ClC-4 and ClC-4A may be accurately predicted. With the predicted structure of ClC-4 and ClC-4A, it is possible to design a library of compounds with structures that would more likely interact with these channels proposed antagonists and agonists which act as inhibitors/enhancers for the channels). Such a library of compounds may be screened for interaction with ClC-4 and/or ClC-4A. Molecules that are proposed agonists may be designed to fit into the binding pocket of the natural ligands for ClC-4A. Thus, new molecules that are detected as sour may be developed as high-intensity taste stimulators. Conversely, antagonists may be modeled to bind to ClC-4A to inhibit the binding of natural ligands to ClC-4A. These antagonists may mask sour taste perception in an animal and may be useful, for example as taste masking agents for foods and medicine.

For alignment of protein sequences for the molecular modeling, any sequence analysis software known in the art may be used. For example, the proteins described by Dutzler et al. (2002) *Nature* 415:287-294 may be aligned with ClC-4A using the Clustal W Program (Thompson, J. D., D. G. Higgins and T. J. Gibson, (1994) "Clustal W: improving the sensitivity of progressive multiple sequence alignment through sequence weighting, position-specific gap penalties and weight matrix choice" *Nucl. Acids Res.* 22:4670-4680). Atomic coordinates of the bacterial channel crystal structures are obtained from the protein database and used along with the alignments as the sources of spatial restraints for modeling. The structural models of ClC-4 and ClC-4A may be generated using any modeling program know in the art, such as, for example the program MODELLER (Sali, A., and T. L. Blundell (1993) "Comparative protein modeling by satisfaction of spatial restraints" *J. Mol. Biol.* 234:779-815). The original images may be created using any programs known in the art, such as, for example, the programs Insight II and Weblab Viewer (Molecular Simulations) and may be further enhanced with a photographic enhancement program such as Adobe Photoshop.

Compositions of Binding and/or Modulating Compounds

Following identification of a compound that binds and/or or modulates a ClC-4 or ClC-4A channel, the compound may be manufactured and/or used in preparation of compositions including, but not limited to, foods, drinks, and pharmaceutical compositions. The compositions are provided or administered to patients, including, but not limited to, birds, cats, dogs, pigs, sheep, goats, cattle, horses, rodents, monkeys, apes, and humans.

Thus, the present invention extends, in various aspects, not only to compounds identified in accordance with the methods disclosed herein but also foods, drinks, pharmaceutical compositions, drugs, or other compositions comprising such a compound; uses of such a compound in the manufacture of a composition for administration to a patient; and methods of making a composition comprising admixing such a compound with a pharmaceutically acceptable excipient, vehicle or carrier, and optionally other ingredients.

Some compositions of the invention comprise a taste-modifying amount of at least one or more binding or modulating compounds. A "taste-modifying amount" is a quantity sufficient to increase or decrease the perception of a taste stimulus by a given mammal. The food and drink compositions of the invention are formulated by the addition of a binding or modulating compound to a food or drink of the mammal.

The pharmaceutical compositions of the invention comprise a therapeutically effective amount of a compound identified according to the methods disclosed herein, or a pharmaceutically acceptable salt thereof, and a pharmaceutically acceptable carrier or excipient.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Pharmaceutically acceptable carriers include but are not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents or pH buffering agents. The composition can be a liquid solution, suspension, emulsion, tablet, pill, capsule, sustained release formulation, or powder. Oral formulations can include standard carriers such as pharmaceutical grades of mannitol, lactose, starch, magnesium stearate, sodium saccharine, cellulose, magnesium carbonate, etc.

The pharmaceutical compositions of the invention may further comprise a secondary compound for the treatment of a disorder unrelated to the ClC-4 or ClC-4A channel, such as an antibiotic or other therapeutic agent, to improve the palatability of the pharmaceutical composition, thereby improving the ease of administration.

In one embodiment, the composition is formulated in accordance with routine procedures as a pharmaceutical composition adapted for oral (e.g., tablets, granules, syrups) administration to the subject.

ClC-4 or ClC-4A of the invention may also be used to identify compounds that will be perceived as sour using cell signaling assays known in the art. In such assays, polynucleotides encoding a ClC-4 or ClC-4A are incorporated into an expression vector and transfected into a host cell. The expression of ClC-4 or ClC-4A may be inducible or constitutive. The host cells expressing ClC-4 or ClC-4A are contacted with candidate sour compounds and the effect of each compound on the cells is assayed. Stimulation of a response is indicative of reactivity to the test compound and correlates with compounds that are perceived as sour. The assays that can be used to assess stimulation of ClC-4 or ClC-4A include, but are not limited to assays measuring ion conductance, ion flow, calcium imaging (e.g., using fura-2, green dextran activity or aquorin activity), voltage measurement and or voltage imaging with dyes, expression of reporter genes (e.g., luciferase, alkaline phosphatase, beta-galactosidase, beta-lactamase, fluorescent binding protein), receptor binding assays, second messenger assays (e.g., IP3, cAMP), G-protein activation based assays (e.g., modulation of GTP-gamma-S binding), receptor phosphorylation measures, and the like. Four fluorescent indicators for chloride are commercially available from Molecular Probes including: 6-methoxy-N-ethylquinolinium iodide (MEQ); 6-methoxy-N-(3-sulfopropyl) quinolinium, inner salt (SPQ); N-(ethoxycarbonylmethyl)-6-methoxyquinolinium bromide (MQAE) (See Sun, X. C. and J. A. Bonanno (2002) "Expression, localization, and functional evaluation of CFTR in bovine corneal endothelial cells" *Am. J. Physiol. Cell. Physiol.* 282(4):C673-683; Geddes C. D. K. Apperson, J. Karolin, and D. J. Birch (2001) "Chloride-sensitive fluorescent indicators" *Anal. Biochem.* 293:60-66. In some embodiments analysis of stimulation of ClC-4 or ClC-4A channels and receptor heterodimers may be determined using a FLIPR® assay as described by the manufacturer (Molecular Devices, Corp.).

Screening of cells treated with dyes and fluorescent reagents is well known in the art. Genetic engineering of cells to produce fluorescent proteins, such as modified green fluorescent protein (GFP), as a reporter molecule is also well known in the art (U.S. Pat. No. 5,491,084). Similarly, WO 96/23898 relates to methods of detecting biologically active substances affecting intracellular processes by utilizing a GFP construct having a protein kinase activation site. U.S. Pat. Nos. 5,401,629 and 5,436,128 describe assays and compositions for detecting and evaluating the intracellular transduction of an extracellular signal using recombinant cells that express cell surface receptors and contain reporter gene constructs that include transcriptional regulatory elements that are responsive to the activity of cell surface receptors. Fluorescence-based reagents are useful for the assay of may cell functions including ion concentrations, membrane potential, specific translocations, enzyme activities, gene expression, as well as the presence, amounts and patterns of metabolites, proteins, lipids, carbohydrates, and nucleic acid sequences (DeBiasio, et al. (1996) *Mol. Biol. Cell.* 7:1259; Giuliano, et al. (1995) *Ann. Rev. Biophys. Biomol. Struct.* 24:405; Heim and Tsien, (1996) *Curr. Biol.* 6:178).

Identification of Antagonists of ClC-4 or ClC-4A

Cell signaling assays known in the art may also be used to identify CC-4 or ClC-4A antagonists. Expression of G protein coupled receptors at very high concentration in a heterologous system has been shown to result in constitutive cell signaling. For example, but not by way of limitation, ClC-4 or ClC-4A may be overexpressed in ClC-4 or ClC-4A/baculovirus-infected *Spodoptera frugiperda* (Sf9) cells. Alternatively, for example, ClC-4 or ClC-4A may be operably linked to a CMV promoter and expressed in COS or HEK293 cells. In the activated constitutive state, test compounds may be assayed for their ability to inhibit constitutive cell signaling activity. Suitable assays include, but are not limited to assays measuring ion conductance, ion flow, calcium imaging (e.g., using fura-2, green dextran activity or aquorin activity), voltage measurement and or voltage imaging with dyes, expression of reporter genes (e.g., luciferase, alkaline phosphatase, β-galactosidase, β-lactamase, fluorescent binding protein), receptor binding assays, second messenger assays (e.g., IP3, cAMP), G-protein activation based assays (e.g., modulation of GTP-gamma-S binding), receptor phosphorylation measures, and the like.

The screening assays of the invention may be used to identify stimuli of ClC-4A. Compounds that specifically bind to ClC-4A may be classified as agonists or antagonists in secondary screening assays in which compounds are tested for the ability to stimulate ion conductance in ClC-4A expressing cells or which block activity of ClC-4A in competition assays with known agonists of ClC-4A. Agonists of ClC-4A may be used as new sour compounds for taste modifiers and taste aversion. Antagonists of ClC-4A may be used as taste modifiers that block sour taste perception.

In some embodiments, the ClC-4A and/or ClC-4 molecules are immobilized on a solid support. Immobilization is accomplished using any of the methods well known in the art, including covalent bonding to a support, a bead, or a chromatographic resin, as well as non-covalent, high affinity interactions such as antibody binding, or use of streptavidin/biotin binding wherein the immobilized compound includes a biotin moiety. The support may, for example, be formulated into an electronic tongue or biosensor.

ClC-4 and ClC-4A present in other parts of the body (other than the tongue) may be exploited for other effects. For example, modulation of expression or function of these receptors may be used to exert an effect on digestion, metabolism or recognition and may be used to stimulate more efficient use of nutrients. Accordingly, the invention also comprises methods of enhancing digestion, metabolism or recognition by modulating the biological activity of ClC-4 and/or ClC-4A in an animal by administering to the animal a compound that modulates expression or function of ClC-4 and/or ClC-4A.

In some embodiments of the invention, the compounds that modulate ClC-4 and/or ClC-4A in locations other than taste buds are antagonists. In other embodiments, the compounds are agonists. In some embodiments of the invention, a method is provided for enhancing an animals efficient use of nutrients comprising administering to the animal an agonist or antagonist of ClC-4 and/or ClC-4A. In some embodiments, modulation of the relative biological activity of ClC-4 to ClC-4A is accomplished by selectively stimulating either ClC-4 or ClC-4A or by selectively antagonizing either ClC-4 or ClC-4A. In some embodiments both ClC-4 and ClC-4A are stimulated. In other embodiments, both ClC-4 and ClC-4A are inhibited. In still other embodiments, modulation of the relative biological activity of ClC-4 to ClC-4A is accomplished by selectively stimulating ClC-4 (or ClC-4A) and simultaneously antagonizing either ClC-4A (or ClC-4), respectively.

Further aspects of the invention are exemplified below, however, the examples are merely illustrative of the invention and the scope of the invention is not to be limited thereto or thereby.

EXAMPLES

Example 1

The discovery of these two voltage-gated, pH-sensitive ion channels ClC-4 and ClC-4A was accomplished in two steps: (1) isolating the 3'-end cDNA fragment from a single taste cell cDNA library by differential screening of the library against non-taste cDNAs; (2) PCR amplification of ClC-4 and ClC-4A cDNAs from a mouse taste tissue cDNA library with PCR primers encompassing the entire coding regions; and PCR screening of a human fungiform (taste) cDNA library. In situ hybridization and immunohistochemistry have localized their transcripts and proteins to taste receptor cells. Electrophysiological recordings have characterized their anion selectivity and conductance in response to changes in voltage and pH.

Construction and Screening of a Single Taste Cell cDNA Library:

Circumvallate, foliate and fungiform papillae epithelium were isolated from young adult mice by enzymatic digestion (Ruiz C., M. McPheeters, and S. C. Kinnamon, "Tissue culture of rat taste buds," in EXPERIMENTAL CELL BIOLOGY OF TASTE AND OLFACTION, CURRENT TECHNIQUES AND PROTOCOLS (eds. Spielman, A. I. and Brand, J. G.) 79-84 (CRC Press, Boca Raton, Fla., 1995). Individual taste cells were dissociated from taste papillae and identified by their unique bipolar shape, and transferred individually to Eppendorf tubes. First strand cDNAs were synthesized from single cells with oligo (dT) primers, and tailed with dATP and terminal transferase, and amplified by polymerase chain reaction (Brady, G. and M. N. Iscove (1993) "Construction of cDNA libraries from single cells" *Methods Enzymol.* 225:611-623; Dulac, C. and R. A. Axel (1995) "A novel family of genes encoding putative pheromone receptors in mammals" *Cell* 83:195-206; Huang, L. et al. (1999) "Gγ13 colocalizes with gustducin in taste receptor cells and mediates IP3 responses to bitter denatonium" *Nature Neurosci.* 2:1055-1062; Perez, C. A. et al. (2002) "A transient receptor potential channel expressed in taste receptor cells" *Nature Neurosci.* 5:1169-1176). The PCR products were digested with restriction enzyme EcoR I and ligated into the λZapII vector. Individual phage plaques were picked and their inserts were amplified with vector-specific primers, size-fractionated by electrophoresis and transferred onto a nylon membrane, which was hybridized with $^{32}$P-labeled cDNAs prepared from non-gustatory lingual epithelium. Inserts of the clones that were not hybridized with the probe were presumed to be expressed selectively in taste cells. These were sequenced and searched against genome and EST (expressed sequence tag) databases.

Isolation of ClC-4 and ClC-4A from Taste Papillae:

Blast search of insert cDNA sequences of one of the clones that was selectively expressed in taste epithelium was 83% identical to human chloride channel 4. PCR amplification was performed with mouse taste tissue cDNAs with primers that were designed to encompass the entire mouse ClC-4. Two fragments were obtained and subcloned into pCR Blunt II TOPO vector. DNA sequencing analysis and sequence alignment showed that the long fragment was the same as the mouse ClC-4 while the short fragment was a splicing isoform of ClC-4, which we designated ClC-4A.

To determine whether these two isoforms are expressed in all three types of lingual taste papillae, a new set of PCR primers were designed and synthesized to encompass the variable region, and PCR reactions were performed with first strand cDNAs from circumvallate, foliate, fungiform and non-gustatory lingual epithelium.

A human fungiform cDNA library was also screened by PCR amplification with human ClC-4 gene specific primers. By dividing PCR screening-positive fractions of the library DNA into subpools, one clone was isolated, which contained the entire coding region.

In Situ Hybridization:

Digoxigenin-labeled RNA probes (ClC-4, 2.2 kb) were used for in situ hybridization on frozen sections (8 μm) as described (Schaeren-Wiemers, N. and A. Gerfin-Moser (1993) "A single protocol to detect transcripts of various types and expression levels in neural tissue and cultured cells: in situ hybridization using digoxigenin-labeled cRNA probes. Histochemistry 100:431-440). Detection was with an alkaline phosphatase-conjugated anti-DIG antibody in the presence of nitroblue tetrazolium (NBT) and 5-bromo-4-chloro-3-indolyl phosphate (BCIP).

Immunohistochemistry:

Polyclonal antiserum against a KLH-conjugated 13-amino acid peptide near the C-terminus of mouse, rat and human ClC-4/ClC-4A was raised in rabbit (Alpha Diagnostic International). Frozen sections (10 μm) of murine lingual tissue (previously fixed in 4% paraformaldehyde and cryoprotected in 20% sucrose) were blocked in 3% BSA, 0.3% Triton X-100, 2% goat serum and 0.1% sodium azide in PBS for 1 hour at room temperature and then incubated overnight at 4° C. with the polyclonal antiserum (1:1,000). The secondary antibody was Cy3-conjugated goat-anti-rabbit Ig.

To determine the type of cells expressing ClC-4/ClC-4A, double immunostaining was carried out on taste sections with the rabbit polyclonal antibody against ClC-4/ClC-4A and the mouse monoclonal antibody against IP3R3 (BD Bioscience, 1:50 dilution). Secondary antibodies were FITC-conjugated and Cy3-conjugated anti-mouse and anti-rabbit antibodies, respectively.

Heterologous Expression in *Xenopus* Oocytes and Electrophysiological Recording:

ClC-4 and ClC-4A cDNAs were subcloned into the expression vector pCR Blunt II TOPO. Capped sense cRNA was synthesized from the linearized expression constructs by T7 RNA polymerase with nMessage mMachine in vitro transcription kit and tailed with polyA tailing kit (Ambion). The synthesized cRNA products were phenol extracted, ethyl alcohol precipitated, and then dissolved in nuclease-free water at about 0.5 ng/nl for injection. Dumont stage V or VI oocytes were obtained from adult female laboratory bred *Xenopus laevis*, and their follicles were removed by collagenase digestion. Oocytes were injected with 50 nl of 0.5 ng/nl cRNA, and maintained at 18° C. for 4-6 days in modified Barth's solution supplemented with 5 mM sodium pyruvate (Goldin, A. L. (1992) "Maintenance of *Xenopus laevis* and oocyte injection" *Methods Enzymol.* 207:266-279). Membrane currents were recorded using the two-electrode voltage-clamp technique in ND96 solution (96 mM NaCl, 2 mM KCl, 1.8 mM $CaCl_2$, 1 mM $MgCl_2$, 5 mM Na-HEPES, pH 7.4). For anion replacement, 80 mM $Cl^-$ was substituted by equivalent amounts of $Br^-$, $I^-$, $NO_3^-$. When using different pH values; 5 mM HEPES (for pH 7.4) was replaced with 5 mM MES (for pH<7.0). For pharmacological analysis, inhibitors of NFA (niflumic acid) at 0.3 mM, or NPPB [5-nitro-2-(3-phenylpropylamino)-benzoic acid] at 0.1 mM were dissolved in ND96 solution.

Recording and current-passing micropipettes with tip resistance <5 MΩ when filled with 3 M KCl were pulled from glass capillaries (A-M Systems Inc., Carlsburg, Wash., USA) using a horizontal puller (Suffer P-80/PC). Currents were recorded with a GeneClamp 500 amplifier, digitized with a Digidata 1200 A/D-D/A system, and stored on a computer running pCLAMP 6 software (all from Axon Instruments, Foster City, Calif., USA). Currents were low-pass filtered at 2 kHz and are shown without subtraction of leakage currents.

Results

Isolation of a Partial Mouse ClC-4 cDNA Sequence:

We isolated circumvallate, foliate and fungiform papillae epithelium from young adult mice and dissociate them into single cells by enzymatic digestion. Individual taste cells were identified by their unique bipolar shape and transferred to Eppendorf tubes, where poly (A) RNAs in each cell were reverse transcribed into first strand cDNAs with oligo (dT) primers. The first strand cDNAs were then tailed with dATP and amplified by polymerase chain reaction (PCR) with restriction enzyme site attached oligo (dT) primers. The amplified products were digested with EcoRI and ligated into the λZapII vector to construct single taste cell cDNA libraries. Individual phage plaques from one of the libraries were picked and their inserts were amplified by PCR with vector-specific primers, sized-fractionated by electrophoresis and transferred onto a nylon membrane. Hybridization of the nylon membranes with radiolabeled cDNAs prepared from non-gustatory lingual epithelium showed that many inserts from the single cell cDNA libraries could hybridize with the non-gustatory lingual epithelium cDNA, generating strong signal after exposed to X-ray film while other insert DNAs did not hybridize to the probe and produce background level signal (FIG. 1). Insert DNAs that did not hybridize to the probe were believed to be the genes that were selectively expressed in gustatory tissue only and their DNAs were isolated, sequenced and blast searched against genome and EST databases. Blast search results showed that one of the clones with a 906 bp insert was 83% identical to a voltage-gated, pH-sensitive human chloride channel 4 (ClC-4) (FIG. 2).

Isolation of a Full-Length ClC-4 cDNAs from Mouse and Human Taste Tissue:

To isolate the full-length ClC-4 cDNA expressed in gustatory tissue, a pair of PCR primers was designed to encompass the entire coding region. PCR amplification with taste tissue cDNA yielded two fragments of 2.4 kb and 2.23 kb. DNA sequencing analysis showed that the 2.4 kb fragment is the same as the previously known mouse chloride channel ClC-4. However, the 2.23 kb fragment is a novel splicing variant, lacking 155 bases near the 5'-end of the ClC-4, including the presumed start codon ATG (FIG. 3). We designated the shorter splicing variant ClC-4A, and its amino acid sequence was deduced from the next in-frame starting codon (FIG. 4).

Figure 5:
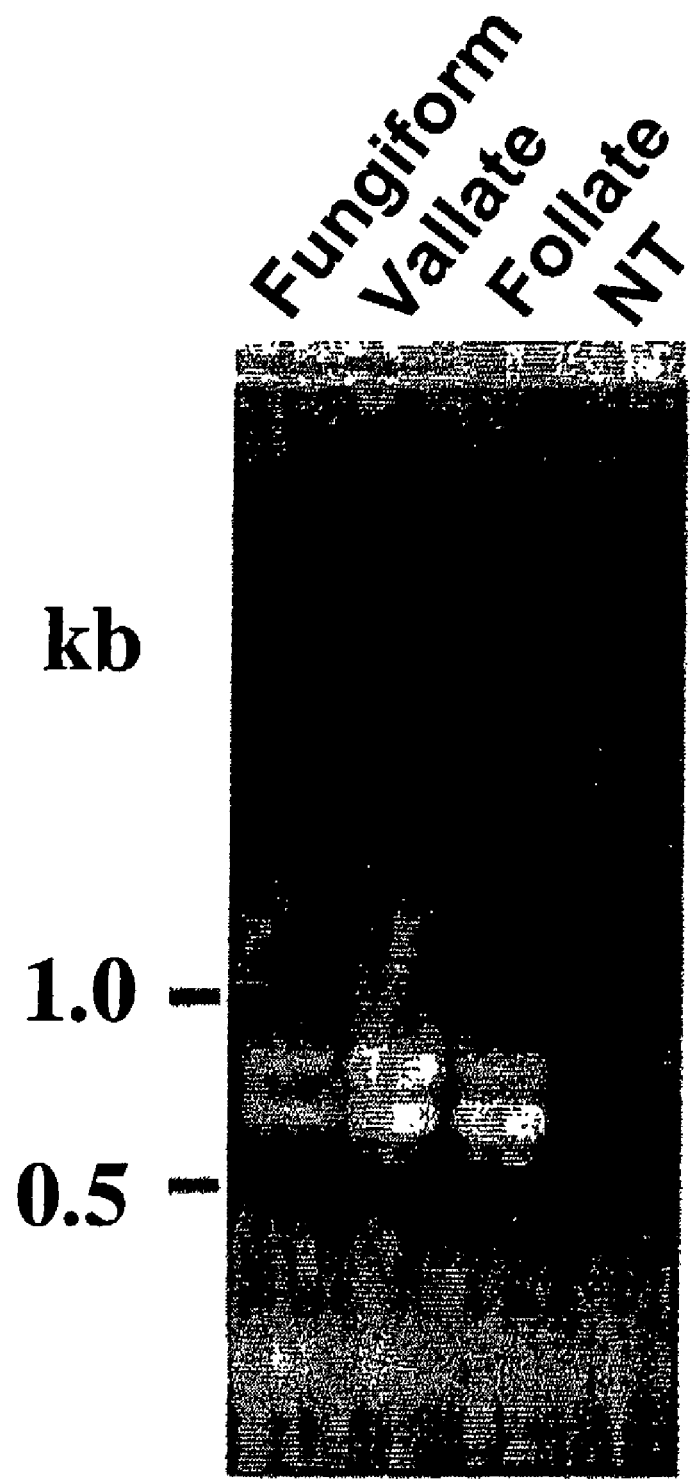
FIG. 5 shows expression of the chloride channels in taste papillae. Both ClC-4 and ClC-4A are expressed in all three types of taste papillae but not in the negative control (non-taste lingual epithelium). PCR amplification was carried out with primers covering the splicing region and first strand cDNAs prepared from taste and non-taste tissues. The expected PCR products for ClC-4 and ClC-4A were detected in cDNAs from fungiform, vallate, foliate papillae but not in the cDNA of non-gustatory lingual epithelium.

To determine whether these two isoforms are expressed in all three types of lingual taste papillae, a new set of PCR primers were designed and synthesized to make the amplification of the variable region of the cDNAs more efficient. PCR amplification with the first strand cDNAs from circumvallate, foliate, fungiform and non-gustatory lingual epithelium showed that both forms of cDNA are present in all three types of papillae, but absent in the non-gustatory lingual epithelium (FIG. 5).

To isolate human ClC-4 cDNA, a human fungiform cDNA library was screened by PCR amplification of pools of the library DNA and dividing the positive pools into subpools. One clone was isolated and sequencing analysis showed that it was a human ClC-4 cDNA. Isolation of human ClC-4A is in process with a new human taste tissue cDNA library.

Figure 6:
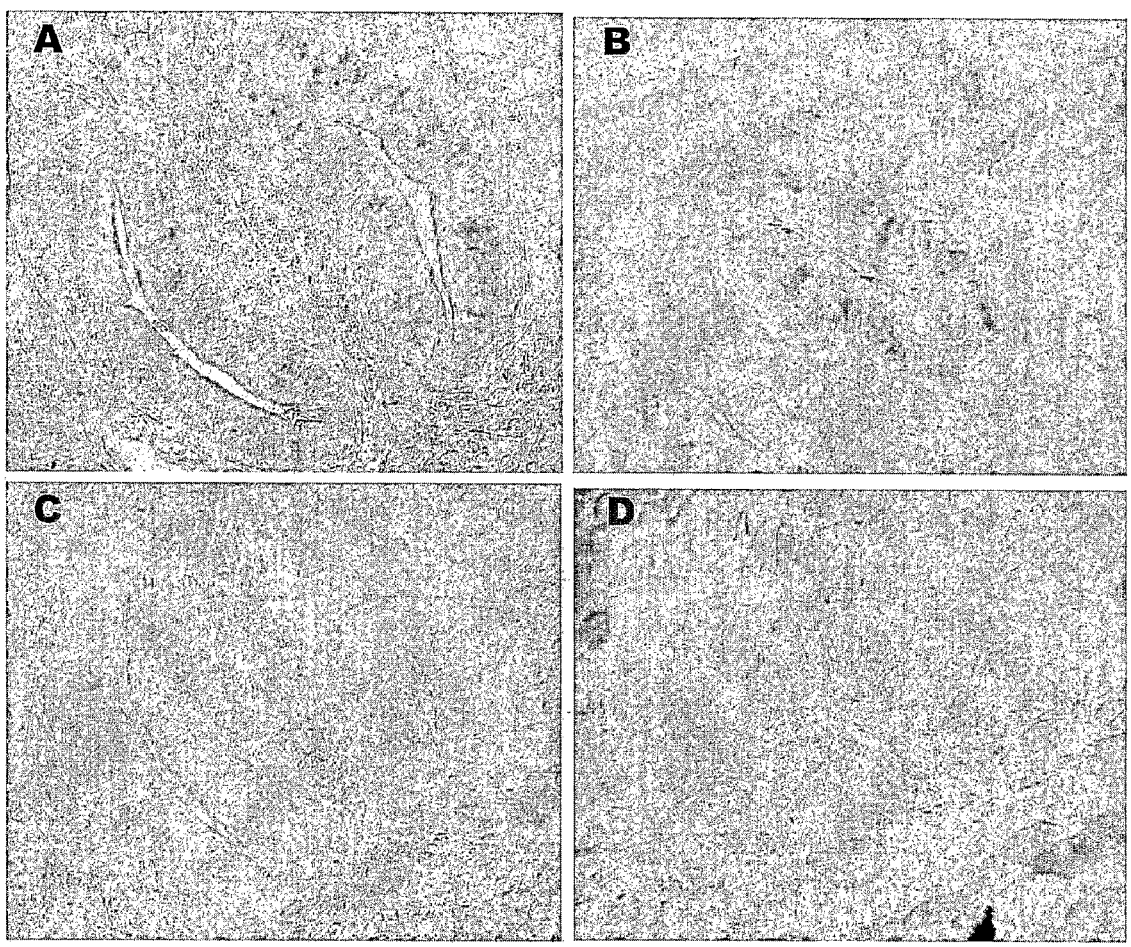
FIG. 6 shows localization of ClC-4/ClC-4A messenger RNAs to taste bud cells. In situ hybridization with antisense probes of ClC-4/ClC-4A detected the expression of ClC-4/ClC-4A in mouse circumvallate (A) and foliate (B) papillae while sense probes showed no non-specific background on these tissues, i.e., circumvallate (C) and foliate (D) papillae.

Localization of ClC-4 RNA Transcripts to Taste Bud Cells:

To localize the RNA transcripts to taste bud cells, in situ hybridization was carried out with a 2.2 kb probe which is common in both ClC-4 and ClC-4A. Results demonstrated that ClC-4/ClC-4A were expressed in many taste bud cells but absent from the surrounding non-gustatory lingual epithelium (FIG. 6). Sense probe controls showed no non-specific hybridization to lingual tissue.

Figure 7:
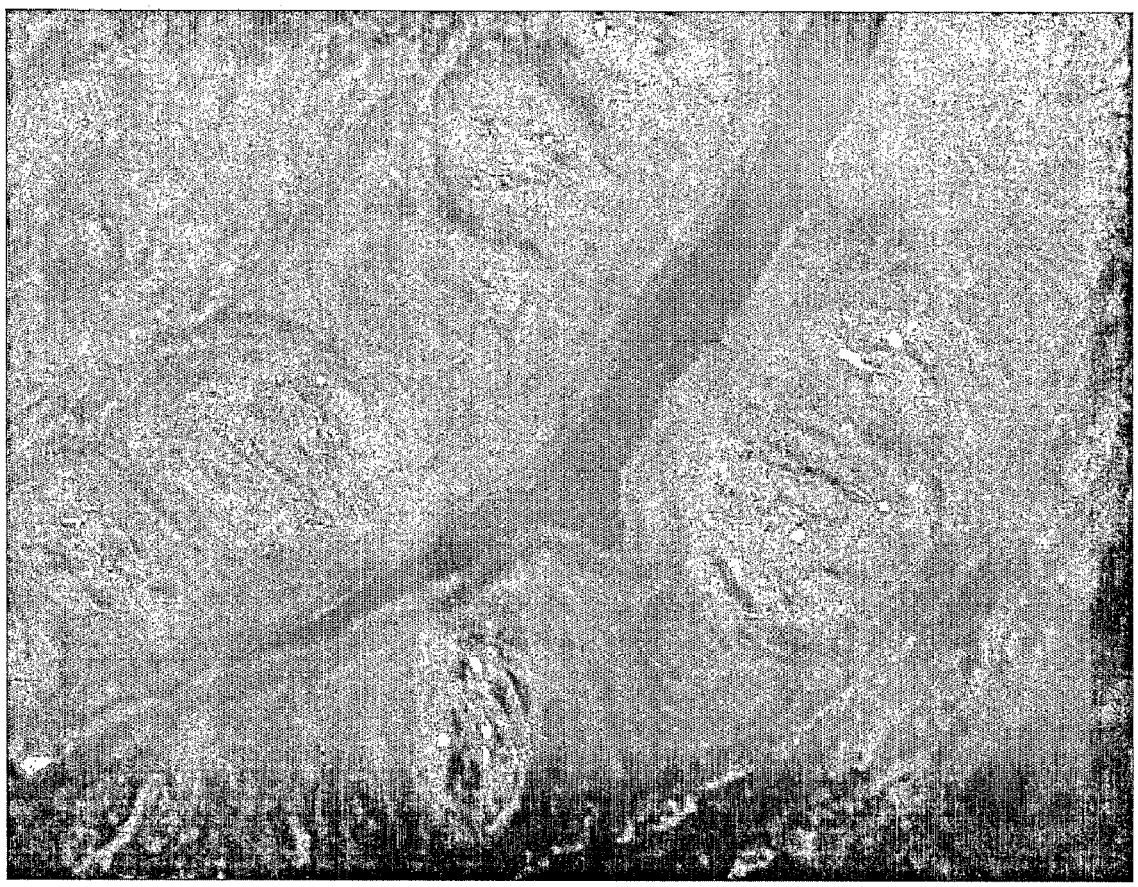
FIG. 7 shows expression of ClC-4/ClC-4A proteins in taste bud cells. Immunohistochemistry of mouse taste tissue with an antibody against a C-terminal peptide sequence of ClC-4/ClC-4A indicated the presence of the proteins in taste bud cells. Some spotty staining suggested that the proteins may also be enriched in some intracellular vesicles such as endosomes and synaptic vesicles.

Expression of ClC-4/ClC-4A Proteins in Taste Receptor Cells:

To determine if the ClC-4/ClC-4A proteins localized to taste receptor cells, we used immunohistochemistry with antiserum to a peptide near C-termini of ClC-4/ClC-4A proteins on sections of murine lingual tissue. This antibody was able to recognize both ClC-4 and ClC-4A. Immunostaining results indicated that the ClC-4/ClC-4A proteins are present on plasma membrane. Some spotty staining seen in cells within the body of the bud suggested that the proteins could also be present in the vesicles such as endosomes and synaptic vesicles (FIG. 7).

Figure 8:
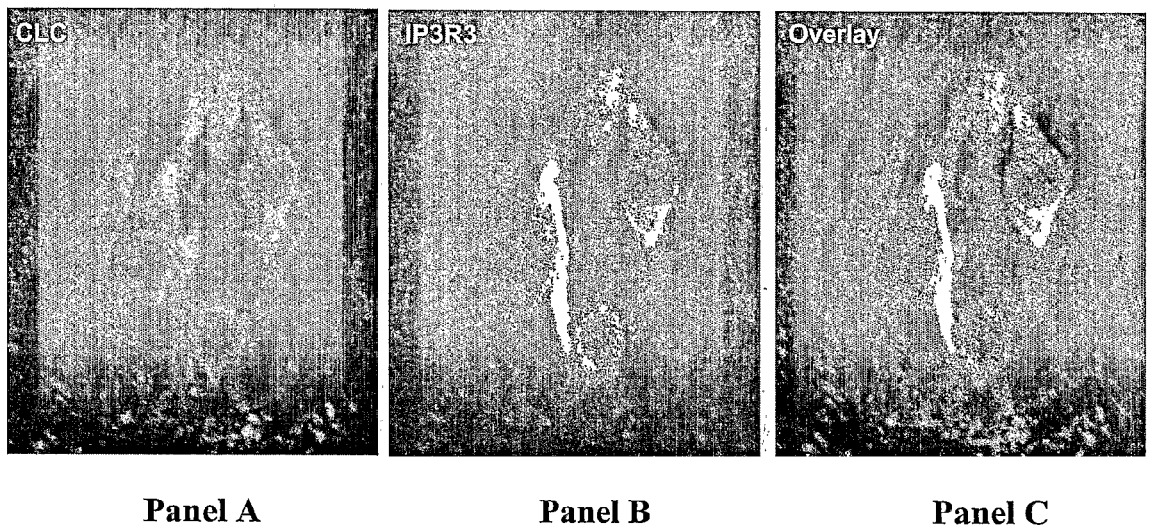
FIG. 8 shows co-expression of ClC channels with IP3R3 in taste bud cells. Double immunostaining was carried out with antibodies against ClC-4/ClC-4A and IP3R3. ClC-4/ClC-4A proteins (Panel A) are overlapping with IP3R3 (Panel B). Overlap is shown in Panel C.

To determine the type of cells expressing ClC-4/ClC-4A, double immunostaining was carried out on taste sections with the ClC-4/ClC-4A antibody produced from rabbit and the IP3R3 monoclonal antibody generated by a mouse cell line. Confocal laser scanning microscopy images (FIG. 8) showed that ClC-4/ClC-4A proteins are nearly overlapping with IP3R3. Since IP3 has been implicated in bitter, sweet and umami sensation, co-expression of ClC-4/ClC-4A with IP3R3 suggests that these chloride channels may play an important role in bitter, sweet and umami taste signal transduction and transmission in taste bud cells.

Figure 9:
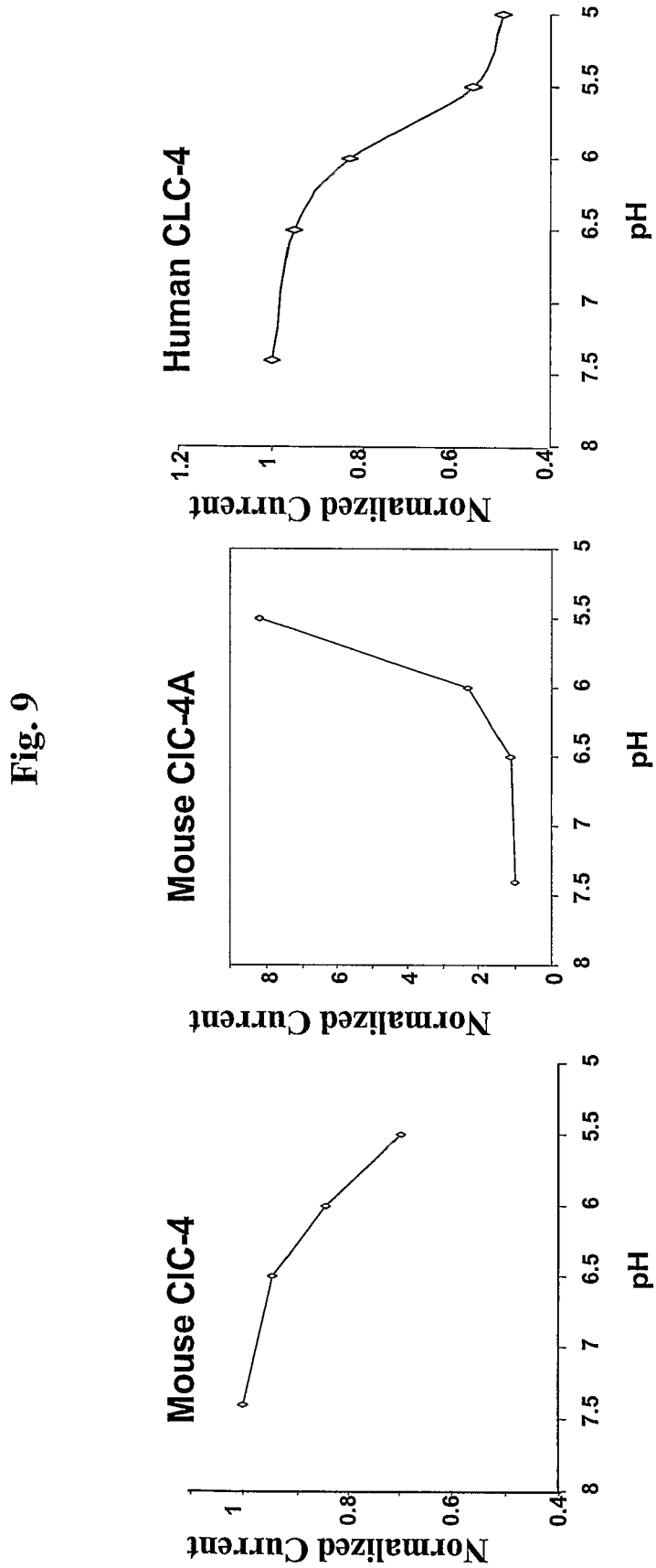
FIG. 9 shows the difference of heterologously expressed ClC-4 and ClC-4A in response to changes in pH. Mouse and human ClC-4 channels had great conductance at pH 7.5-6.5 and began to close at lower pH (left and right panels). In contrast, the splicing variant ClC-4A was closed at neutral pH and open at acidic pH (middle panel).

Functional Characterization of ClC-4 and ClC-4A Channels:

To characterize the function of ClC-4 and ClC-4A, we subcloned their cDNAs into the expression vector pCR Blunt II TOPO and synthesized the capped sense cRNA with in vitro transcription and tailed the cRNA with poly (A), which was then purified and injected into *Xenopus* oocytes. Membrane currents were recorded using the two-electrode voltage-clamp technique 4-6 days after injection. Strong outward currents were recorded in ClC-4 cRNA-injected oocytes, which were absent in the control oocytes. ClC-4-mediated currents were markedly reduced by extracellular acidification (FIG. 9, left panel), indicating that ClC-4 channels were open in pH 7.5-6.5, and began to close from pH 6.5. By contrast, currents in ClC-4A-injected oocytes at pH 7.5 and 6.5 were close to the basal level as recorded from the control oocytes, and strong outward currents were recorded at pH 6.5, 6.0 and 5.5, indicating that ClC-4A was closed at pH 7.5 and 6.5, but open at the lower pH (FIG. 9, middle panel). We also tested the sensitivity of human ClC-4 activity to external pH (FIG. 9, right panel), and found that like mouse ClC-4, human counterpart was closed at acidic pH, which is consistent with previous studies.

When chloride was replaced with other anions, results showed the different ion selectivity for ClC-4 and ClC-4A (FIG. 10). The conductance sequence of ClC-4 is I$^-$=NO$_3^-$>Br$^-$>Cl$^-$ (FIG. 10a) while the sequence of ClC-4A is I$^-$>>Br$^-$=Cl$^-$>NO$_3^-$ (FIG. 10b). These ion selectivities were quite different from those reported for the human ClC-4. To confirm our results, we expressed and recorded from human ClC-4, and the conductance sequence is nearly identical to the reported data: NO$_3^-$>Cl$^-$>Br$^-$>I$^-$ (FIG. 10c), indicating that the 2% difference in amino acid sequence between human and mouse ClC-4 confers anion selectivity.

Figure 11A:
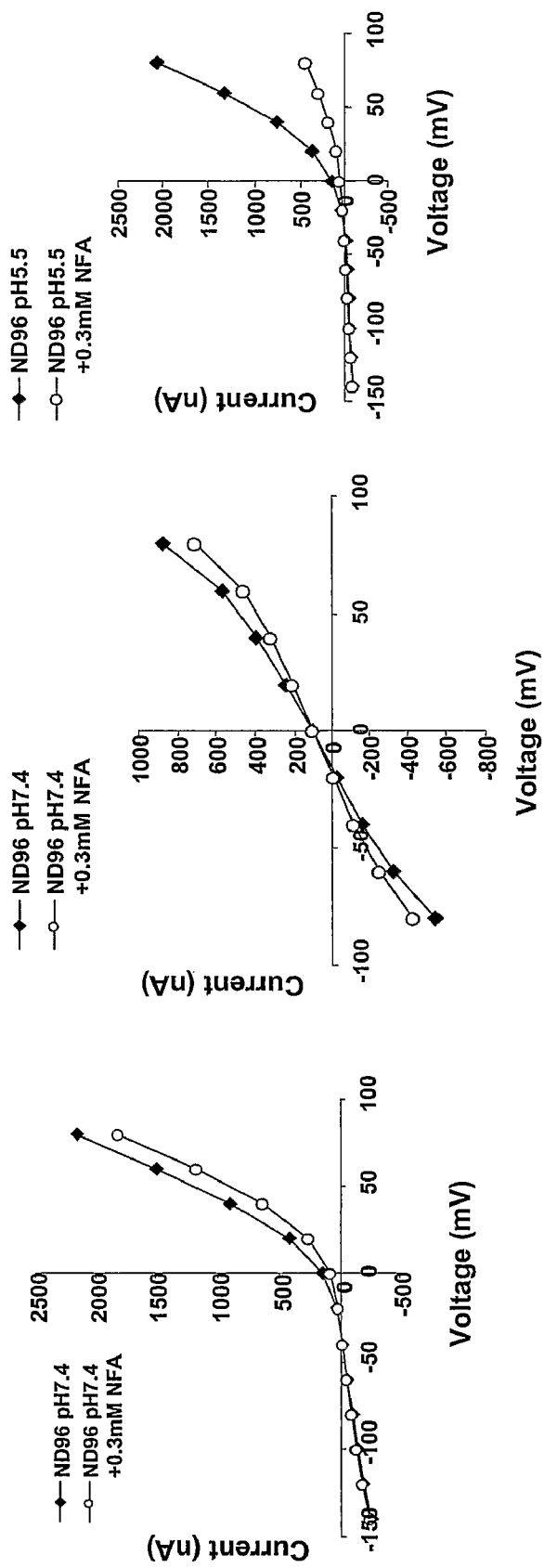
FIG. 11A shows current-voltage curves and FIG. 11B shows corresponding bar graphs at greatest conductance. 0.3 mM NFA had slight effect on human and mouse ClC-4 conductance but significantly inhibited ClC-4A.
Figure 11B:
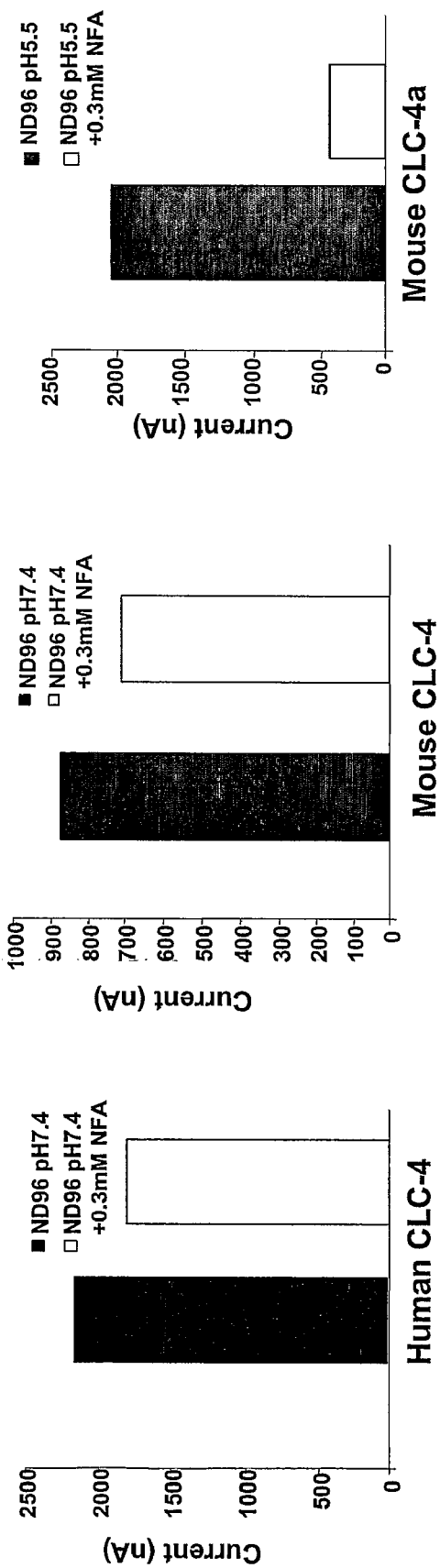
Figure 12A:
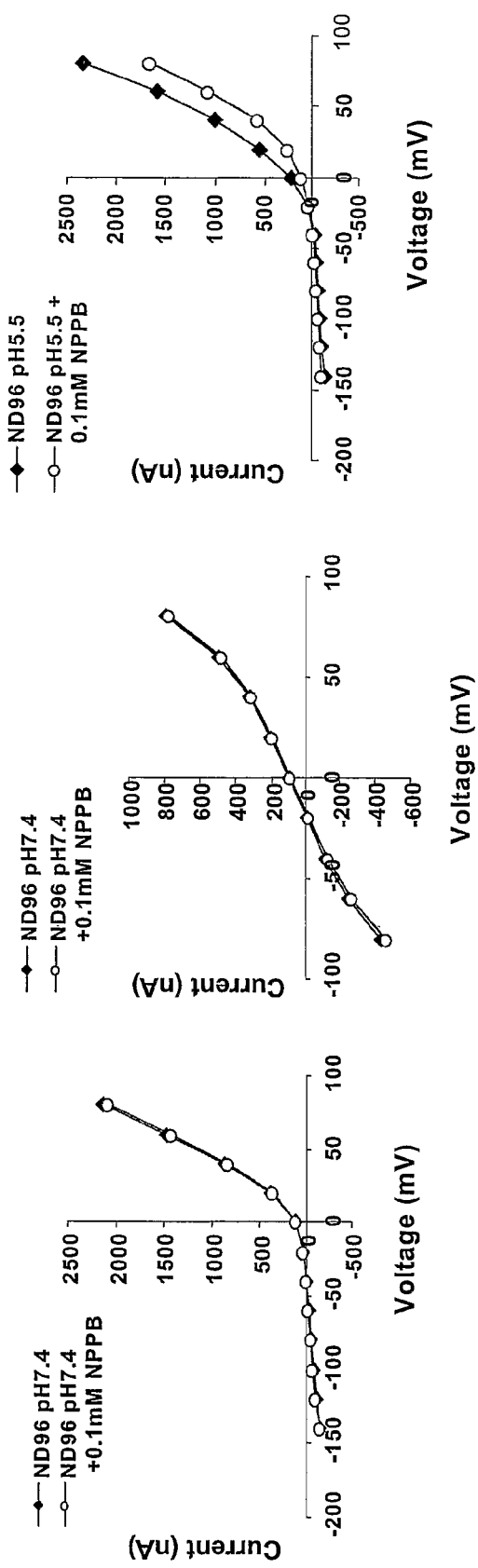

To pharmacologically characterize these ion channels, we tested the effect of chloride channel inhibitors on these channels at their optimal pH: NFA (niflumic acid) and NPPB [5-nitro-2-(3-phenylpropylamino)-benzoic acid]. Results indicated that NFA had only a slight inhibitory effect on human and mouse ClC-4 (FIG. 11, left and middle panels) at pH 7.4, but significantly inhibited the conductance of ClC-4A at pH 5.5 (FIG. 11, right panels). NPPB had no apparent effect on the conductance of human and mouse ClC-4 channels but did slightly inhibit ClC-4A (FIG. 12).

What is claimed:

1. An isolated polynucleotide comprising the nucleotide sequence of SEQ ID NO:6, the nucleotide sequence of SEQ ID NO:11, or a sequence encoding a polypeptide wherein said polypeptide consists of the amino acid sequence of SEQ ID NO:8 or an amino acid sequence comprising up to 15 amino acid changes relative to SEQ ID NO: 8.

2. An expression vector comprising the polynucleotide of claim 1 operably linked to a promoter.

3. A host cell comprising the expression vector of claim 2.

4. The host cell of claim 3 wherein said cell is a mammalian cell.

5. The host cell of claim 3 wherein said cell is from an animal selected from the group consisting of human, mouse, rat, dog, cow, pig, cat, ox, buffalo, llama, sheep, horse, goat, llama, monkey, and ape.

6. The host cell of claim 3 wherein said cell is from an animal selected from the group consisting of a frog, bird, bacterium, yeast, insect, and nematode.

7. A cell culture comprising at least one cell of claim 5 or 6.

8. An isolated and purified ClC-4A polypeptide consisting of the amino acid sequence of SEQ ID NO:8 or an amino acid sequence comprising up to 15 amino acid changes relative to the amino acid sequence of SEQ ID NO:8 or comprising the amino acid sequence encoded by the nucleotide sequence of SEQ ID NO:6 or SEQ ID NO:11.

9. The polypeptide of claim 8 wherein said polypeptide consists of the amino acid sequence of SEQ ID NO:8.

10. A method for identifying taste modifiers comprising contacting a ClC-4A polypeptide, wherein said ClC-4A polypeptide is encoded by the nucleotide sequence of SEQ ID NO:6 or SEQ ID NO: 11 or consists of the amino acid sequence of SEQ ID NO: 8 or an amino acid sequence comprising up to 15 amino acid changes relative to the amino acid sequence of SEQ ID NO: 8, with a potential taste modifier and detecting binding of said potential taste modifier to said ClC-4A polypeptide.

11. The method of claim 10 wherein said ClC4-A polypeptide is expressed on the surface of a host cell.

12. The method of claim 10 wherein said potential taste modifier modulates intracellular chloride concentration.

13. The method of claim 11 wherein said host cells are *Xenopus* oocytes.

14. The method of claim 11 wherein said host cells are mammalian cells.

15. The method of claim 14 wherein said mammalian cells are selected from the group consisting of human embryonic kidney cells, Chinese hamster ovary cells, HeLa cells, baby hamster kidney cells, monkey kidney cells, N1E-115 cells, and PC 12 human hepatocellular carcinoma cells.

16. The method of claim 10 wherein said ClC4-A polypeptide is immobilized on a solid substrate.

* * * * *

SEQUENCE LISTING

<160> NUMBER OF SEQ ID NOS: 64

<210> SEQ ID NO 1
<211> LENGTH: 906
<212> TYPE: DNA
<213> ORGANISM: Mus musculus

<400> SEQUENCE: 1

| | | | | | | |
|---|---|---|---|---|---|---|
| atagagccat | gatgagagtg | aggcatatga | gttctcagtg | ggaactcctc | caaatggatt | 60 |
| acaagagaaa | tagtaaattg | attctaaatc | tgttccattc | tcttccctgt | aggatataaa | 120 |
| atgtccagtt | ttaacgccta | agcatggact | ttcaaactag | caatcacagc | gcgggacaga | 180 |
| gtcacatttt | atacagccaa | ttgaagcact | gggtctcttt | gtgtttgaac | ttaatggcaa | 240 |
| ttttattctt | taaattctgc | acatctgtct | tttcttcagg | aaggaattag | tgtttcaggc | 300 |
| ccatcgcatg | atctgtgtaa | gatttgtgtc | acttgccatt | tcacttcatc | tttgcccctc | 360 |
| acttttcact | gagtcatcct | cctccttttc | agtcttactg | tcattgggta | tcgttgaatc | 420 |
| acgtatgtgc | acttgactgt | atgtaataga | tcctgacagt | gcacctaaga | aacctgggac | 480 |
| atggccagtc | caggactgtc | tctacactat | tgccagggtt | ccaaaatctt | ctggttttca | 540 |
| ttttccctct | tcttattctc | tgtcctctgg | cttactgcct | catagttgta | aaattgttgc | 600 |
| ccagatgcca | ggtgcgatgt | ctactttctg | tgagggaagg | aggggagag | gcgagtacga | 660 |
| agatgaatgt | gtatatcttt | cccagagatg | cgcagcatac | aaccattggc | tggaaatctg | 720 |
| ttatatgccc | cattcgccta | gatgtctgta | aatacaggaa | ggaaaattgt | tttagctata | 780 |
| cattataaca | cattactttc | tggatggaat | ttcgattctg | tggataggga | agtgggattg | 840 |
| gtatctgtca | tattaaattc | caacatcatg | tccctgccat | tgttttttt | tttttttt | 900 |
| tttttt | | | | | | 906 |

<210> SEQ ID NO 2
<211> LENGTH: 216
<212> TYPE: DNA
<213> ORGANISM: Mus musculus

<400> SEQUENCE: 2

| | | | | | | |
|---|---|---|---|---|---|---|
| tgaggcatat | gagttctcag | tgggaactcc | tccaaatgga | ttacaagaga | aatagtaaat | 60 |
| tgattctaaa | tctgttccat | tctcttccct | gtaggatata | aaatgtccag | ttttaacgcc | 120 |
| taagcatgga | ctttcaaact | agcaatcaca | gcgcgggaca | gagtcacatt | ttatacagcc | 180 |
| aattgaagca | ctgggtctct | ttgtgtttga | acttaa | | | 216 |

<210> SEQ ID NO 3
<211> LENGTH: 218
<212> TYPE: DNA
<213> ORGANISM: Homo sapiens

<400> SEQUENCE: 3

| | | |
|---|---|---|
| tgaggcatat gcgttgtcag ttggaatccc tccaaatgga ttgcaagaga aatactaaat | 60 |
| tgattctaaa tctgttccat tatcttctct gtaggatgca aaacatccag ttgtaatgta | 120 |
| taagcatgca cttcatacta gcaatcacag cacaggagga cagcattaaa ttttatatag | 180 |
| ccaatttggg cactgggcat ctttgtattt gaacttaa | 218 |

<210> SEQ ID NO 4
<211> LENGTH: 217
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t

<400> SEQUENCE: 4

| | | |
|---|---|---|
| tgaggcatat gmgttstcag tkggaayycc tccaaatgga ttrcaagaga aatastaaat | 60 |
| tgattctaaa tctgttccat tmtcttcyct gtaggatrya aaayrtccag ttktaaygym | 120 |
| taagcatgsa cnttcawact agcaatcaca gcngsrggac agmrtyamat tttatayagc | 180 |
| caattkrrgc actgggymtc tttgtrtttg aacttaa | 217 |

<210> SEQ ID NO 5
<211> LENGTH: 2445
<212> TYPE: DNA
<213> ORGANISM: Mus musculus

<400> SEQUENCE: 5

| | | |
|---|---|---|
| ctgaagagag gaggatgatc taggacgctg tccgggtgga cggccacgcc gcaagacgcg | 60 |
| gccctgcagg agtgactagc acggtcaggg cgggagccac gagcgcctct gggaacctca | 120 |
| tggacttcct cgaggagccc ttccctgacg tggggaccta cgaggacttc cacaccatag | 180 |
| actggctgag ggaaaagtcc cgggataccg acagacatag gaagatcacc agcaaaagta | 240 |
| aggagtctat ttgggagttc atcaagagcc tgctggacgc gtggtcggga tgggtggtga | 300 |
| tgctactcat tgggctgctg gcaggtacct tggctggagt catcgatctc gctgtggatt | 360 |
| ggatgacgga cctcaaggag ggggtctgtc tgtccgcatt ctggtacagc catgaacagt | 420 |
| gctgttggac ctccaacgag accacttttg aggacaggga caagtgtccc ctgtggcaga | 480 |
| agtggtcaga gcttcttctg agccagtcag agggcgccag cgcttacatt ctgaattact | 540 |
| taatgtacat tctatgggcg ttgctgtttg catttctggc tgtctccctg gtacgtgtgt | 600 |
| tcgcaccgta tgcctgtggc tctggcatac ccgagataaa gactattttg agtggcttta | 660 |
| tcatcagggg atacttgggg aaatggactc ttctaatcaa gactgtcacc ctcgtgctcg | 720 |
| tcgtatcctc tggcctgagc cttggcaaag agggcccact ggtgcatgtg gcatgttgct | 780 |
| gtggcaactt cttcagcagc cttttctcca agtatagcaa gaatgaaggc aagaggcgtg | 840 |

```
aggtgctttc agctgcagct gctgctggtg tctctgtggc cttttggtgct ccgataggag      900
gtgtgctctt cagtctagag gaggtcagtt actactttcc cttgaaaacc ttgtggaggt      960
cattctttgc agccctggtg gctgccttca cactgcgctc catcaacccc tttggaaata     1020
gccgcctggt tctctttat gtggagtatc atacaccctg gtacatggct gaactcttcc      1080
ctttcatcct gcttggagtc tttggggggtt tatggggaac cctcttcaca cgctgcaaca    1140
ttgcttggtg caggaggcgt aagaccacca ggctgggcag gtacccagtg ttggaggtta     1200
ttgcggtgac agccgtcacc gccatcgtgg cctaccccaa tccctacact cgccagagca     1260
ccagtgagct catctctgag ctcttcaacg attgtggggc tctcgagtct tctcagctct     1320
gtgactacat caacgacccc aacatgactc ggcctgtgga tgacattccg gaccggccgg     1380
ctggggttgg agtttacaca gccatgtggc agctggcctt ggcactgatc ttcaaaatag     1440
tcattactat atttaccttt ggcatgaaga ttccctcagg tctcttcatc cccagtatgg     1500
ctgtcggagc catggcaggc cggatggtgg gaatcggtgt ggagcagctg gcctaccatc     1560
accatgactg gatcatcttc aggaactggt gcaggcctgg agcggactgt gtcacaccag     1620
ggctttatgc gatggtggga gctgcagcct gtcaggtgg ggtgactagg atgacagtgt      1680
ctctagtggt cattatgttt gaactgactg gaggtctgga gtatattgta cccctgatgg     1740
cagctgctgt caccagcaag tgggtggctg atgcctttgg gaaagaaggg atttatgaag     1800
cccacatcca tctgaatggg tacccatttc ttgatgtgaa ggatgagttc acccaccgta     1860
cgctggccac tgatgtgatg cggccccgga ggggagaacc gccattatcg gtactaaccc     1920
aggacagcat gactgtggag gacgtggaga ctctcatcaa ggagacagac tacaacggct     1980
ttcctgtgct cgtctccaga gactcggagc gtctcatcgg gtttgcccag aggcgggagc     2040
taatcttggc tataaaaaat gccaggcaga ggcaagaggg cattgtgagc aattccatca     2100
tgtacttcac agaggagcct cctgagctgc ctgccaacag cccacatcca ctgaagctga     2160
ggcgcatttt gaacctgagc cctttcacgg tcacagatca caccccatg gagacggtgg      2220
tggacatttt ccggaaactg gggctccgac aatgcctggt gacacggagt gggagacttc     2280
ttgggatcat cacaaaaaag gatgttctga cacacatggc ccagatggca aaccaggacc     2340
ctgaatccat catgtttaat tagcaataag atgggcatta ttttgagaag atcaataatt     2400
atatcatttt taaagaaata accaagtgat acattatgat cctaa                    2445

<210> SEQ ID NO 6
<211> LENGTH: 2290
<212> TYPE: DNA
<213> ORGANISM: Mus Musculus

<400> SEQUENCE: 6
ctgaagagag gaggatgatc taggacgctg tccgggtgga cggccacgcc gcaagacgcg       60
gccctgcaga tcaccagcaa aagtaaggag tctatttggg agttcatcaa gagcctgctg      120
gacgcgtggt cgggatgggt ggtgatgcta ctcattgggc tgctggcagg taccttggct      180
ggagtcatcg atctcgctgt ggattggatg acgacctca aggagggggt ctgtctgtcc       240
gcattctggt acagccatga acagtgctgt tggacctcca acgagaccac ttttgaggac      300
agggacaagt gtccctgtg gcagaagtgg tcagagcttc ttctgagcca gtcagagggc      360
gccagcgctt acattctgaa ttacttaatg tacattctat gggcgttgct gtttgcattt      420
ctggctgtct ccctggtacg tgtgttcgca ccgtatgcct gtggctctgg catacccgag      480
ataaagacta ttttgagtgg ctttatcatc aggggatact tggggaaatg gactcttcta     540
```

```
atcaagactg tcaccctcgt gctcgtcgta tcctctggcc tgagccttgg caaagagggc    600
ccactggtgc atgtggcatg ttgctgtggc aacttcttca gcagccttt  ctccaagtat    660
agcaagaatg aaggcaagag gcgtgaggtg ctttcagctg cagctgctgc tggtgtctct    720
gtggcctttg gtgctccgat aggaggtgtg ctcttcagtc tagaggaggt cagttactac    780
tttcccttga aaaccttgtg gaggtcattc tttgcagccc tggtgctgc  cttcacactg    840
cgctccatca ccccctttgg aaatagccgc ctggttctct tttatgtgga gtatcataca    900
ccctggtaca tggctgaact cttcccttc  atcctgcttg gagtctttgg gggtttatgg    960
ggaaccctct tcacacgctg caacattgct tggtgcagga ggcgtaagac caccaggctg   1020
ggcaggtacc cagtgttgga ggttattgcg gtgacagccg tcaccgccat cgtggcctac   1080
cccaatccct acactcgcca gagcaccagt gagctcatct ctgagctctt caacgattgt   1140
ggggctctcg agtcttctca gctctgtgac tacatcaacg accccaacat gactcggcct   1200
gtggatgaca ttccggaccg gccggctggg gttggagttt acacagccat gtggcagctg   1260
gccttggcac tgatcttcaa aatagtcatt actatattta cctttggcat gaagattccc   1320
tcaggtctct tcatccccag tatggctgtc ggagccatgg caggccggat ggtgggaatc   1380
ggtgtggagc agctggccta ccatcaccat gactggatca tcttcaggaa ctggtgcagg   1440
cctggagcgg actgtgtcac accagggctt tatgcgatgg tgggagctgc agcctgtcta   1500
ggtggggtga ctaggatgac agtgtctcta gtggtcatta tgtttgaact gactggaggt   1560
ctggagtata ttgtaccct  gatggcagct gctgtcacca gcaagtgggt ggctgatgcc   1620
tttgggaaag aagggattta tgaagcccac atccatctga atgggtaccc atttcttgat   1680
gtgaaggatg agttcaccca ccgtacgctg ccactgatg  tgatgcggcc ccggagggga   1740
gaaccgccat tatcggtact aacccaggac agcatgactg tggaggacgt ggagactctc   1800
atcaaggaga cagactacaa cggctttcct gtgctcgtct ccagagactc ggagcgtctc   1860
atcgggtttg cccagaggcg ggagctaatc ttggctataa aaatgccag  gcagaggcaa   1920
gagggcattg tgagcaattc catcatgtac ttcacagagg agcctcctga gctgcctgcc   1980
aacagcccac atccactgaa gctgaggcgc attttgaacc tgagcccttt cacggtcaca   2040
gatcacaccc ccatggagac ggtggtggac attttccgga aactgggct  ccgacaatgc   2100
ctggtgacac ggagtgggag acttcttggg atcatcacaa aaaggatgt  tctgagacac   2160
atggcccaga tggcaaacca ggaccctgaa tccatcatgt taattagca  ataagatggg   2220
cattattttg agaagatcaa taattatatc attttttaaag aaataaccaa gtgatacatt   2280
atgatcctaa                                                          2290
```

<210> SEQ ID NO 7
<211> LENGTH: 747
<212> TYPE: PRT
<213> ORGANISM: Mus musculus

<400> SEQUENCE: 7

Met Asp Phe Leu Glu Glu Pro Phe Pro Asp Val Gly Thr Tyr Glu Asp
1               5                   10                  15

Phe His Thr Ile Asp Trp Leu Arg Glu Lys Ser Arg Asp Thr Asp Arg
            20                  25                  30

His Arg Lys Ile Thr Ser Lys Ser Lys Glu Ser Ile Trp Glu Phe Ile
        35                  40                  45

Lys Ser Leu Leu Asp Ala Trp Ser Gly Trp Val Val Met Leu Leu Ile

-continued

```
                 50                  55                  60
Gly Leu Leu Ala Gly Thr Leu Ala Gly Val Ile Asp Leu Ala Val Asp
 65                  70                  75                  80

Trp Met Thr Asp Leu Lys Glu Gly Val Cys Leu Ser Ala Phe Trp Tyr
                 85                  90                  95

Ser His Glu Gln Cys Cys Trp Thr Ser Asn Glu Thr Thr Phe Glu Asp
                100                 105                 110

Arg Asp Lys Cys Pro Leu Trp Gln Lys Trp Ser Glu Leu Leu Leu Ser
                115                 120                 125

Gln Ser Glu Gly Ala Ser Ala Tyr Ile Leu Asn Tyr Leu Met Tyr Ile
    130                 135                 140

Leu Trp Ala Leu Leu Phe Ala Phe Leu Ala Val Ser Leu Val Arg Val
145                 150                 155                 160

Phe Ala Pro Tyr Ala Cys Gly Ser Gly Ile Pro Glu Ile Lys Thr Ile
                165                 170                 175

Leu Ser Gly Phe Ile Ile Arg Gly Tyr Leu Gly Lys Trp Thr Leu Leu
                180                 185                 190

Ile Lys Thr Val Thr Leu Val Leu Val Val Ser Ser Gly Leu Ser Leu
    195                 200                 205

Gly Lys Glu Gly Pro Leu Val His Val Ala Cys Cys Cys Gly Asn Phe
210                 215                 220

Phe Ser Ser Leu Phe Ser Lys Tyr Ser Lys Asn Glu Gly Lys Arg Arg
225                 230                 235                 240

Glu Val Leu Ser Ala Ala Ala Ala Gly Val Ser Val Ala Phe Gly
                245                 250                 255

Ala Pro Ile Gly Gly Val Leu Phe Ser Leu Glu Glu Val Ser Tyr Tyr
                260                 265                 270

Phe Pro Leu Lys Thr Leu Trp Arg Ser Phe Phe Ala Ala Leu Val Ala
                275                 280                 285

Ala Phe Thr Leu Arg Ser Ile Asn Pro Phe Gly Asn Ser Arg Leu Val
    290                 295                 300

Leu Phe Tyr Val Glu Tyr His Thr Pro Trp Tyr Met Ala Glu Leu Phe
305                 310                 315                 320

Pro Phe Ile Leu Leu Gly Val Phe Gly Gly Leu Trp Gly Thr Leu Phe
                325                 330                 335

Thr Arg Cys Asn Ile Ala Trp Cys Arg Arg Arg Lys Thr Thr Arg Leu
                340                 345                 350

Gly Arg Tyr Pro Val Leu Glu Val Ile Ala Val Thr Ala Val Thr Ala
    355                 360                 365

Ile Val Ala Tyr Pro Asn Pro Tyr Thr Arg Gln Ser Thr Ser Glu Leu
    370                 375                 380

Ile Ser Glu Leu Phe Asn Asp Cys Gly Ala Leu Glu Ser Ser Gln Leu
385                 390                 395                 400

Cys Asp Tyr Ile Asn Asp Pro Asn Met Thr Arg Pro Val Asp Asp Ile
                405                 410                 415

Pro Asp Arg Pro Ala Gly Val Gly Val Tyr Thr Ala Met Trp Gln Leu
                420                 425                 430

Ala Leu Ala Leu Ile Phe Lys Ile Val Ile Thr Ile Phe Thr Phe Gly
    435                 440                 445

Met Lys Ile Pro Ser Gly Leu Phe Ile Pro Ser Met Ala Val Gly Ala
    450                 455                 460

Met Ala Gly Arg Met Val Gly Ile Gly Val Glu Gln Leu Ala Tyr His
465                 470                 475                 480
```

```
His His Asp Trp Ile Ile Phe Arg Asn Trp Cys Arg Pro Gly Ala Asp
            485                 490                 495

Cys Val Thr Pro Gly Leu Tyr Ala Met Val Gly Ala Ala Cys Leu
            500                 505                 510

Gly Gly Val Thr Arg Met Thr Val Ser Leu Val Val Ile Met Phe Glu
            515                 520                 525

Leu Thr Gly Gly Leu Glu Tyr Ile Val Pro Leu Met Ala Ala Ala Val
            530                 535                 540

Thr Ser Lys Trp Val Ala Asp Ala Phe Gly Lys Glu Gly Ile Tyr Glu
545                 550                 555                 560

Ala His Ile His Leu Asn Gly Tyr Pro Phe Leu Asp Val Lys Asp Glu
                565                 570                 575

Phe Thr His Arg Thr Leu Ala Thr Asp Val Met Arg Pro Arg Arg Gly
                580                 585                 590

Glu Pro Pro Leu Ser Val Leu Thr Gln Asp Ser Met Thr Val Glu Asp
                595                 600                 605

Val Glu Thr Leu Ile Lys Glu Thr Asp Tyr Asn Gly Phe Pro Val Leu
                610                 615                 620

Val Ser Arg Asp Ser Glu Arg Leu Ile Gly Phe Ala Gln Arg Arg Glu
625                 630                 635                 640

Leu Ile Leu Ala Ile Lys Asn Ala Arg Gln Arg Gln Glu Gly Ile Val
                645                 650                 655

Ser Asn Ser Ile Met Tyr Phe Thr Glu Glu Pro Pro Glu Leu Pro Ala
                660                 665                 670

Asn Ser Pro His Pro Leu Lys Leu Arg Arg Ile Leu Asn Leu Ser Pro
                675                 680                 685

Phe Thr Val Thr Asp His Thr Pro Met Glu Thr Val Val Asp Ile Phe
                690                 695                 700

Arg Lys Leu Gly Leu Arg Gln Cys Leu Val Thr Arg Ser Gly Arg Leu
705                 710                 715                 720

Leu Gly Ile Ile Thr Lys Lys Asp Val Leu Arg His Met Ala Gln Met
                725                 730                 735

Ala Asn Gln Asp Pro Glu Ser Ile Met Phe Asn
                740                 745

<210> SEQ ID NO 8
<211> LENGTH: 687
<212> TYPE: PRT
<213> ORGANISM: Mus musculus

<400> SEQUENCE: 8

Met Leu Leu Ile Gly Leu Leu Ala Gly Thr Leu Ala Gly Val Ile Asp
1               5                   10                  15

Leu Ala Val Asp Trp Met Thr Asp Leu Lys Glu Gly Val Cys Leu Ser
                20                  25                  30

Ala Phe Trp Tyr Ser His Glu Gln Cys Cys Trp Thr Ser Asn Glu Thr
                35                  40                  45

Thr Phe Glu Asp Arg Asp Lys Cys Pro Leu Trp Gln Lys Trp Ser Glu
            50                  55                  60

Leu Leu Leu Ser Gln Ser Glu Gly Ala Ser Ala Tyr Ile Leu Asn Tyr
65                  70                  75                  80

Leu Met Tyr Ile Leu Trp Ala Leu Leu Phe Ala Phe Leu Ala Val Ser
                85                  90                  95

Leu Val Arg Val Phe Ala Pro Tyr Ala Cys Gly Ser Gly Ile Pro Glu
```

-continued

```
            100                 105                 110
Ile Lys Thr Ile Leu Ser Gly Phe Ile Ile Arg Gly Tyr Leu Gly Lys
            115                 120                 125

Trp Thr Leu Leu Ile Lys Thr Val Thr Leu Val Leu Val Val Ser Ser
            130                 135                 140

Gly Leu Ser Leu Gly Lys Glu Gly Pro Leu Val His Val Ala Cys Cys
145                 150                 155                 160

Cys Gly Asn Phe Phe Ser Ser Leu Phe Ser Lys Tyr Ser Lys Asn Glu
                165                 170                 175

Gly Lys Arg Arg Glu Val Leu Ser Ala Ala Ala Ala Gly Val Ser
            180                 185                 190

Val Ala Phe Gly Ala Pro Ile Gly Gly Val Leu Phe Ser Leu Glu Glu
            195                 200                 205

Val Ser Tyr Tyr Phe Pro Leu Lys Thr Leu Trp Arg Ser Phe Phe Ala
            210                 215                 220

Ala Leu Val Ala Ala Phe Thr Leu Arg Ser Ile Asn Pro Phe Gly Asn
225                 230                 235                 240

Ser Arg Leu Val Leu Phe Tyr Val Glu Tyr His Thr Pro Trp Tyr Met
                245                 250                 255

Ala Glu Leu Phe Pro Phe Ile Leu Leu Gly Val Phe Gly Gly Leu Trp
            260                 265                 270

Gly Thr Leu Phe Thr Arg Cys Asn Ile Ala Trp Cys Arg Arg Lys
            275                 280                 285

Thr Thr Arg Leu Gly Arg Tyr Pro Val Leu Glu Val Ile Ala Val Thr
            290                 295                 300

Ala Val Thr Ala Ile Val Ala Tyr Pro Asn Pro Tyr Thr Arg Gln Ser
305                 310                 315                 320

Thr Ser Glu Leu Ile Ser Glu Leu Phe Asn Asp Cys Gly Ala Leu Glu
                325                 330                 335

Ser Ser Gln Leu Cys Asp Tyr Ile Asn Asp Pro Asn Met Thr Arg Pro
            340                 345                 350

Val Asp Asp Ile Pro Asp Arg Pro Ala Gly Val Gly Val Tyr Thr Ala
            355                 360                 365

Met Trp Gln Leu Ala Leu Ala Leu Ile Phe Lys Ile Val Ile Thr Ile
            370                 375                 380

Phe Thr Phe Gly Met Lys Ile Pro Ser Gly Leu Phe Ile Pro Ser Met
385                 390                 395                 400

Ala Val Gly Ala Met Ala Gly Arg Met Val Gly Ile Gly Val Glu Gln
                405                 410                 415

Leu Ala Tyr His His His Asp Trp Ile Ile Phe Arg Asn Trp Cys Arg
            420                 425                 430

Pro Gly Ala Asp Cys Val Thr Pro Gly Leu Tyr Ala Met Val Gly Ala
            435                 440                 445

Ala Ala Cys Leu Gly Gly Val Thr Arg Met Thr Val Ser Leu Val Val
            450                 455                 460

Ile Met Phe Glu Leu Thr Gly Gly Leu Glu Tyr Ile Val Pro Leu Met
465                 470                 475                 480

Ala Ala Ala Val Thr Ser Lys Trp Val Ala Asp Ala Phe Gly Lys Glu
                485                 490                 495

Gly Ile Tyr Glu Ala His Ile His Leu Asn Gly Tyr Pro Phe Leu Asp
            500                 505                 510

Val Lys Asp Glu Phe Thr His Arg Thr Leu Ala Thr Asp Val Met Arg
            515                 520                 525
```

US 7,785,807 B2

Pro Arg Arg Gly Glu Pro Pro Leu Ser Val Leu Thr Gln Asp Ser Met
            530                 535                 540

Thr Val Glu Asp Val Glu Thr Leu Ile Lys Glu Thr Asp Tyr Asn Gly
545                 550                 555                 560

Phe Pro Val Leu Val Ser Arg Asp Ser Glu Arg Leu Ile Gly Phe Ala
                565                 570                 575

Gln Arg Arg Glu Leu Ile Leu Ala Ile Lys Asn Ala Arg Gln Arg Gln
            580                 585                 590

Glu Gly Ile Val Ser Asn Ser Ile Met Tyr Phe Thr Glu Glu Pro Pro
        595                 600                 605

Glu Leu Pro Ala Asn Ser Pro His Pro Leu Lys Leu Arg Arg Ile Leu
    610                 615                 620

Asn Leu Ser Pro Phe Thr Val Thr Asp His Thr Pro Met Glu Thr Val
625                 630                 635                 640

Val Asp Ile Phe Arg Lys Leu Gly Leu Arg Gln Cys Leu Val Thr Arg
                645                 650                 655

Ser Gly Arg Leu Leu Gly Ile Ile Thr Lys Lys Asp Val Leu Arg His
            660                 665                 670

Met Ala Gln Met Ala Asn Gln Asp Pro Glu Ser Ile Met Phe Asn
        675                 680                 685

<210> SEQ ID NO 9
<211> LENGTH: 60
<212> TYPE: PRT
<213> ORGANISM: Mus musculus

<400> SEQUENCE: 9

Met Asp Phe Leu Glu Glu Pro Phe Pro Asp Val Gly Thr Tyr Glu Asp
1               5                   10                  15

Phe His Thr Ile Asp Trp Leu Arg Glu Lys Ser Arg Asp Thr Asp Arg
            20                  25                  30

His Arg Lys Ile Thr Ser Lys Ser Lys Glu Ser Ile Trp Glu Phe Ile
        35                  40                  45

Lys Ser Leu Leu Asp Ala Trp Ser Gly Trp Val Val
    50                  55                  60

<210> SEQ ID NO 10
<211> LENGTH: 2244
<212> TYPE: DNA
<213> ORGANISM: Mus musculus

<400> SEQUENCE: 10
atggacttcc tcgaggagcc cttccctgac gtggggacct acgaggactt ccacaccata      60
gactggctga gggaaaagtc ccgggatacc gacagacata ggaagatcac cagcaaaagt     120
aaggagtcta tttgggagtt catcaagagc ctgctggacg cgtggtcggg atgggtggtg     180
atgctactca ttgggctgct ggcaggtacc ttggctggag tcatcgatct cgctgtggat     240
tggatgacgg acctcaagga gggggtctgt ctgtccgcat tctggtacag ccatgaacag     300
tgctgttgga cctccaacga ccactttt gaggacaggg acaagtgtcc cctgtggcag     360
aagtggtcag agcttcttct gagccagtca gagggcgcca gcgcttacat tctgaattac     420
ttaatgtaca ttctatgggc gttgctgttt gcatttctgg ctgtctccct ggtacgtgtg     480
ttcgcaccgt atgcctgtgg ctctggcata cccgagataa agactatttt gagtggcttt     540
atcatcaggg gatacttggg gaaatggact cttctaatca agactgtcac cctcgtgctc     600

| | |
|---|---|
| gtcgtatcct ctggcctgag ccttggcaaa gagggcccac tggtgcatgt ggcatgttgc | 660 |
| tgtggcaact tcttcagcag ccttttctcc aagtatagca agaatgaagg caagaggcgt | 720 |
| gaggtgcttt cagctgcagc tgctgctggt gtctctgtgg cctttggtgc tccgatagga | 780 |
| ggtgtgctct tcagtctaga ggaggtcagt tactactttc ccttgaaaac cttgtggagg | 840 |
| tcattctttg cagccctggt ggctgccttc acactgcgct ccatcaaccc ctttggaaat | 900 |
| agccgcctgg ttctctttta tgtggagtat catacaccct ggtacatggc tgaactcttc | 960 |
| cctttcatcc tgcttggagt ctttgggggt ttatggggaa ccctcttcac acgctgcaac | 1020 |
| attgcttggt gcaggaggcg taagaccacc aggctgggca ggtacccagt gttggaggtt | 1080 |
| attgcggtga cagccgtcac cgccatcgtg gcctacccca tccctacac tcgccagagc | 1140 |
| accagtgagc tcatctctga gctcttcaac gattgtgggg ctctcgagtc ttctcagctc | 1200 |
| tgtgactaca tcaacgaccc caacatgact cggcctgtgg atgacattcc ggaccggccg | 1260 |
| gctgggggttg gagtttacac agccatgtgg cagctggcct tggcactgat cttcaaaata | 1320 |
| gtcattacta tatttacctt tggcatgaag attccctcag gtctcttcat ccccagtatg | 1380 |
| gctgtcggag ccatggcagg ccggatggtg ggaatcggtg tggagcagct ggcctaccat | 1440 |
| caccatgact ggatcatctt caggaactgg tgcaggcctg gagcggactg tgtcacacca | 1500 |
| gggctttatg cgatggtggg agctgcagcc tgtctaggtg gggtgactag gatgacagtg | 1560 |
| tctctagtgg tcattatgtt tgaactgact ggaggtctgg agtatattgt accctgatg | 1620 |
| gcagctgctg tcaccagcaa gtgggtggct gatgcctttg ggaaagaagg gatttatgaa | 1680 |
| gcccacatcc atctgaatgg gtacccattt cttgatgtga aggatgagtt cacccaccgt | 1740 |
| acgctggcca ctgatgtgat gcggccccgg aggggagaac cgccattatc ggtactaacc | 1800 |
| caggacagca tgactgtgga ggacgtggag actctcatca aggagacaga ctacaacggc | 1860 |
| tttcctgtgc tcgtctccag agactcggag cgtctcatcg ggtttgccca gaggcgggag | 1920 |
| ctaatcttgg ctataaaaaa tgccaggcag aggcaagagg gcattgtgag caattccatc | 1980 |
| atgtacttca cagaggagcc tcctgagctg cctgccaaca gcccacatcc actgaagctg | 2040 |
| aggcgcattt tgaacctgag ccctttcacg gtcacagatc acaccccat ggagacggtg | 2100 |
| gtggacattt tccggaaact ggggctccga caatgcctgg tgacacgag tgggagactt | 2160 |
| cttgggatca tcacaaaaaa ggatgttctg agacacatgg cccagatggc aaaccaggac | 2220 |
| cctgaatcca tcatgtttaa ttag | 2244 |

<210> SEQ ID NO 11
<211> LENGTH: 2064
<212> TYPE: DNA
<213> ORGANISM: Mus musculus

<400> SEQUENCE: 11

| | |
|---|---|
| atgctactca ttgggctgct ggcaggtacc ttggctggag tcatcgatct cgctgtggat | 60 |
| tggatgacgg acctcaagga gggggtctgt ctgtccgcat tctggtacag ccatgaacag | 120 |
| tgctgttgga cctccaacga gaccactttt gaggacaggg acaagtgtcc cctgtggcag | 180 |
| aagtggtcag agcttcttct gagccagtca gagggcgcca cgcttacat tctgaattac | 240 |
| ttaatgtaca ttctatgggc gttgctgttt gcatttctgg ctgtctccct ggtacgtgtg | 300 |
| ttcgcaccgt atgcctgtgg ctctggcata cccgagataa agactatttt gagtggcttt | 360 |
| atcatcaggg gatacttggg gaaatggact cttctaatca agactgtcac cctcgtgctc | 420 |
| gtcgtatcct ctggcctgag ccttggcaaa gagggcccac tggtgcatgt ggcatgttgc | 480 |

-continued

```
tgtggcaact tcttcagcag cctttctcc aagtatagca agaatgaagg caagaggcgt      540
gaggtgcttt cagctgcagc tgctgctggt gtctctgtgg cctttggtgc tccgatagga      600
ggtgtgctct tcagtctaga ggaggtcagt tactactttc ccttgaaaac cttgtggagg      660
tcattctttg cagccctggt ggctgccttc acactgcgct ccatcaaccc ctttggaaat      720
agccgcctgg ttctctttta tgtggagtat catacaccct ggtacatggc tgaactcttc      780
cctttcatcc tgcttggagt ctttggggt ttatggggaa ccctcttcac acgctgcaac      840
attgcttggt gcaggaggcg taagaccacc aggctgggca ggtacccagt gttggaggtt      900
attgcggtga cagccgtcac cgccatcgtg gcctacccca tccctacac tcgccagagc      960 accagtgagc tcatctctga gctcttcaac gattgtgggg ctctcgagtc ttctcagctc     1020
tgtgactaca tcaacgaccc caacatgact cggcctgtgg atgacattcc ggaccggccg     1080
gctggggttg gagtttacac agccatgtgg cagctggcct tggcactgat cttcaaaata     1140
gtcattacta tatttacctt tggcatgaag attccctcag gtctcttcat ccccagtatg     1200
gctgtcggag ccatggcagg ccggatggtg ggaatcggtg tggagcagct ggcctaccat     1260
caccatgact ggatcatctt caggaactgg tgcaggcctg gagcggactg tgtcacacca     1320
gggctttatg cgatggtggg agctgcagcc tgtctaggtg gggtgactag atgacagtg      1380 tctctagtgg tcattatgtt tgaactgact ggaggtctgg agtatattgt accctgatg      1440 gcagctgctg tcaccagcaa gtgggtggct gatgcctttg gaaagaagg gatttatgaa      1500 gcccacatcc atctgaatgg gtacccattt cttgatgtga aggatgagtt cacccaccgt     1560
acgctggcca ctgatgtgat gcggccccgg aggagaaac cgccattatc ggtactaacc      1620
caggacagca tgactgtgga ggacgtggag actctcatca aggagacaga ctacaacggc     1680
tttcctgtgc tcgtctccag agactcggag cgtctcatcg ggtttgccca gaggcgggag     1740
ctaatcttgg ctataaaaaa tgccaggcag aggcaagagg gcattgtgag caattccatc     1800
atgtacttca cagaggagcc tcctgagctg cctgccaaca gcccacatcc actgaagctg     1860
aggcgcattt tgaacctgag ccctttcacg gtcacagatc acaccccat ggagacggtg      1920 gtggacattt tccggaaact ggggctccga caatgcctgg tgacacggag tgggagactt     1980
cttgggatca tcacaaaaaa ggatgttctg agacacatgg cccagatggc aaaccaggac     2040
cctgaatcca tcatgtttaa ttag                                           2064
```

```
<210> SEQ ID NO 12
<211> LENGTH: 180
<212> TYPE: DNA
<213> ORGANISM: Mus musculus

<400> SEQUENCE: 12
atggacttcc tcgaggagcc cttccctgac gtggggacct acgaggactt ccacaccata       60
gactggctga gggaaaagtc ccgggatacc gacagacata ggaagatcac cagcaaaagt      120
aaggagtcta tttgggagtt catcaagagc ctgctggacg cgtggtcggg atgggtggtg      180

<210> SEQ ID NO 13
<211> LENGTH: 21
<212> TYPE: PRT
<213> ORGANISM: Mus musculus

<400> SEQUENCE: 13

Trp Ser Gly Trp Val Val Met Leu Leu Ile Gly Leu Leu Ala Gly Thr
1               5                   10                  15
```

Leu Ala Gly Val Ile
            20

<210> SEQ ID NO 14
<211> LENGTH: 21
<212> TYPE: PRT
<213> ORGANISM: Mus musculus

<400> SEQUENCE: 14

Ala Tyr Ile Leu Asn Tyr Leu Met Tyr Ile Leu Trp Ala Leu Leu Phe
1               5                   10                  15

Ala Phe Leu Ala Val
            20

<210> SEQ ID NO 15
<211> LENGTH: 21
<212> TYPE: PRT
<213> ORGANISM: Mus musculus

<400> SEQUENCE: 15

Trp Thr Leu Leu Ile Lys Thr Val Thr Leu Val Leu Val Val Ser Ser
1               5                   10                  15

Gly Leu Ser Leu Gly
            20

<210> SEQ ID NO 16
<211> LENGTH: 21
<212> TYPE: PRT
<213> ORGANISM: Mus musculus

<400> SEQUENCE: 16

Ala Ala Ala Ala Gly Val Ser Val Ala Phe Gly Ala Pro Ile Gly Gly
1               5                   10                  15

Val Leu Phe Ser Leu
            20

<210> SEQ ID NO 17
<211> LENGTH: 21
<212> TYPE: PRT
<213> ORGANISM: Mus musculus

<400> SEQUENCE: 17

Ala Glu Leu Phe Pro Phe Ile Leu Leu Gly Val Phe Gly Gly Leu Trp
1               5                   10                  15

Gly Thr Leu Phe Thr
            20

<210> SEQ ID NO 18
<211> LENGTH: 21
<212> TYPE: PRT
<213> ORGANISM: Mus musculus

<400> SEQUENCE: 18

Leu Gly Arg Tyr Pro Val Leu Glu Val Ile Ala Val Thr Ala Val Thr
1               5                   10                  15

Ala Ile Val Ala Tyr
            20

<210> SEQ ID NO 19
<211> LENGTH: 21
<212> TYPE: PRT
<213> ORGANISM: Mus musculus

```
<400> SEQUENCE: 19

Met Trp Gln Leu Ala Leu Ala Leu Ile Phe Lys Ile Val Ile Thr Ile
1               5                   10                  15

Phe Thr Phe Gly Met
            20

<210> SEQ ID NO 20
<211> LENGTH: 21
<212> TYPE: PRT
<213> ORGANISM: Mus musculus

<400> SEQUENCE: 20

Gly Leu Phe Ile Pro Ser Met Ala Val Gly Ala Met Ala Gly Arg Met
1               5                   10                  15

Val Gly Ile Gly Val
            20

<210> SEQ ID NO 21
<211> LENGTH: 21
<212> TYPE: PRT
<213> ORGANISM: Mus musculus

<400> SEQUENCE: 21

Ala Asp Cys Val Thr Pro Gly Leu Tyr Ala Met Val Gly Ala Ala Ala
1               5                   10                  15

Cys Leu Gly Gly Val
            20

<210> SEQ ID NO 22
<211> LENGTH: 21
<212> TYPE: PRT
<213> ORGANISM: Mus musculus

<400> SEQUENCE: 22

Leu Val Val Ile Met Phe Glu Leu Thr Gly Gly Leu Glu Tyr Ile Val
1               5                   10                  15

Pro Leu Met Ala Ala
            20

<210> SEQ ID NO 23
<211> LENGTH: 61
<212> TYPE: PRT
<213> ORGANISM: Mus musculus

<400> SEQUENCE: 23

Val Met Arg Pro Arg Gly Glu Pro Pro Leu Ser Val Leu Thr Gln
1               5                   10                  15

Asp Ser Met Thr Val Glu Asp Val Glu Thr Leu Ile Lys Glu Thr Asp
                20                  25                  30

Tyr Asn Gly Phe Pro Val Leu Val Ser Arg Asp Ser Glu Arg Leu Ile
            35                  40                  45

Gly Phe Ala Gln Arg Arg Glu Leu Ile Leu Ala Ile Lys
        50                  55                  60

<210> SEQ ID NO 24
<211> LENGTH: 50
<212> TYPE: PRT
<213> ORGANISM: Mus musculus

<400> SEQUENCE: 24
```

-continued

```
Leu Asn Leu Ser Pro Phe Thr Val Thr Asp His Thr Pro Met Glu Thr
1               5                   10                  15

Val Val Asp Ile Phe Arg Lys Leu Gly Leu Arg Gln Cys Leu Val Thr
                20                  25                  30

Arg Ser Gly Arg Leu Leu Gly Ile Ile Thr Lys Lys Asp Val Leu Arg
            35                  40                  45

His Met
    50
```

<210> SEQ ID NO 25
<211> LENGTH: 63
<212> TYPE: DNA
<213> ORGANISM: Mus musculus

<400> SEQUENCE: 25
tggtcgggat gggtggtgat gctactcatt gggctgctgg caggtacctt ggctggagtc   60
atc                                                                 63

<210> SEQ ID NO 26
<211> LENGTH: 63
<212> TYPE: DNA
<213> ORGANISM: Mus musculus

<400> SEQUENCE: 26
gcttacattc tgaattactt aatgtacatt ctatgggcgt tgctgtttgc atttctggct   60
gtc                                                                 63

<210> SEQ ID NO 27
<211> LENGTH: 63
<212> TYPE: DNA
<213> ORGANISM: Mus musculus

<400> SEQUENCE: 27
tggactcttc taatcaagac tgtcaccctc gtgctcgtcg tatcctctgg cctgagcctt   60
ggc                                                                 63

<210> SEQ ID NO 28
<211> LENGTH: 63
<212> TYPE: DNA
<213> ORGANISM: Mus musculus

<400> SEQUENCE: 28
gcagctgctg ctggtgtctc tgtggccttt ggtgctccga taggaggtgt gctcttcagt   60
cta                                                                 63

<210> SEQ ID NO 29
<211> LENGTH: 63
<212> TYPE: DNA
<213> ORGANISM: Mus musculus

<400> SEQUENCE: 29
gctgaactct tccctttcat cctgcttgga gtctttgggg gtttatgggg aaccctcttc   60
aca                                                                 63

<210> SEQ ID NO 30
<211> LENGTH: 63
<212> TYPE: DNA
<213> ORGANISM: Mus musculus

<400> SEQUENCE: 30

```
ctgggcaggt acccagtgtt ggaggttatt gcggtgacag ccgtcaccgc catcgtggcc    60
tac                                                                  63

<210> SEQ ID NO 31
<211> LENGTH: 63
<212> TYPE: DNA
<213> ORGANISM: Mus musculus

<400> SEQUENCE: 31
atgtggcagc tggccttggc actgatcttc aaaatagtca ttactatatt tacctttggc    60
atg                                                                  63

<210> SEQ ID NO 32
<211> LENGTH: 63
<212> TYPE: DNA
<213> ORGANISM: Mus musculus

<400> SEQUENCE: 32
ggtctcttca tccccagtat ggctgtcgga gccatggcag gccggatggt gggaatcggt    60
gtg                                                                  63

<210> SEQ ID NO 33
<211> LENGTH: 63
<212> TYPE: DNA
<213> ORGANISM: Mus musculus

<400> SEQUENCE: 33
gcggactgtg tcacaccagg gctttatgcg atggtgggag ctgcagcctg tctaggtggg    60
gtg                                                                  63

<210> SEQ ID NO 34
<211> LENGTH: 183
<212> TYPE: DNA
<213> ORGANISM: Mus musculus

<400> SEQUENCE: 34
gtgatgcggc cccggagggg agaaccgcca ttatcggtac taacccagga cagcatgact    60
gtggaggacg tggagactct catcaaggag acagactaca acggctttcc tgtgctcgtc   120
tccagagact cggagcgtct catcgggttt gcccagaggc gggagctaat cttggctata   180
aaa                                                                 183

<210> SEQ ID NO 35
<211> LENGTH: 150
<212> TYPE: DNA
<213> ORGANISM: Mus musculus

<400> SEQUENCE: 35
ttgaacctga gcccttttcac ggtcacagat cacaccccca tggagacggt ggtggacatt    60
ttccggaaac tggggctccg acaatgcctg gtgacacgga gtgggagact tcttgggatc   120
atcacaaaaa aggatgttct gagacacatg                                    150

<210> SEQ ID NO 36
<211> LENGTH: 33
<212> TYPE: PRT
<213> ORGANISM: Mus musculus

<400> SEQUENCE: 36
```

-continued

Met Leu Leu Ile Gly Leu Leu Ala Gly Thr Leu Ala Gly Val Ile Asp
1               5                   10                  15

Leu Ala Val Asp Trp Met Thr Asp Leu Lys Glu Gly Val Cys Leu Ser
            20                  25                  30

Ala

<210> SEQ ID NO 37
<211> LENGTH: 23
<212> TYPE: PRT
<213> ORGANISM: Mus musculus

<400> SEQUENCE: 37

Leu Asn Tyr Leu Met Tyr Ile Leu Trp Ala Leu Leu Phe Ala Phe Leu
1               5                   10                  15

Ala Val Ser Leu Val Arg Val
            20

<210> SEQ ID NO 38
<211> LENGTH: 9
<212> TYPE: PRT
<213> ORGANISM: Mus musculus

<400> SEQUENCE: 38

Ser Gly Ile Pro Glu Ile Lys Thr Ile
1               5

<210> SEQ ID NO 39
<211> LENGTH: 20
<212> TYPE: PRT
<213> ORGANISM: Mus musculus

<400> SEQUENCE: 39

Tyr Leu Gly Lys Trp Thr Leu Leu Ile Lys Thr Val Thr Leu Val Leu
1               5                   10                  15

Val Val Ser Ser
            20

<210> SEQ ID NO 40
<211> LENGTH: 20
<212> TYPE: PRT
<213> ORGANISM: Mus musculus

<400> SEQUENCE: 40

Lys Glu Gly Pro Leu Val His Val Ala Cys Cys Cys Gly Asn Phe Phe
1               5                   10                  15

Ser Ser Leu Phe
            20

<210> SEQ ID NO 41
<211> LENGTH: 18
<212> TYPE: PRT
<213> ORGANISM: Mus musculus

<400> SEQUENCE: 41

Glu Gly Lys Arg Arg Glu Val Leu Ser Ala Ala Ala Ala Gly Val
1               5                   10                  15

Ser Val

<210> SEQ ID NO 42
<211> LENGTH: 10
<212> TYPE: PRT
<213> ORGANISM: Mus musculus -continued

```
<400> SEQUENCE: 42

Pro Ile Gly Gly Val Leu Phe Ser Leu Glu
1               5                   10

<210> SEQ ID NO 43
<211> LENGTH: 20
<212> TYPE: PRT
<213> ORGANISM: Mus musculus

<400> SEQUENCE: 43

Thr Leu Trp Arg Ser Phe Phe Ala Ala Leu Val Ala Ala Phe Thr Leu
1               5                   10                  15

Arg Ser Ile Asn
            20

<210> SEQ ID NO 44
<211> LENGTH: 31
<212> TYPE: PRT
<213> ORGANISM: Mus musculus

<400> SEQUENCE: 44

Leu Phe Pro Phe Ile Leu Leu Gly Val Phe Gly Gly Leu Trp Gly Thr
1               5                   10                  15

Leu Phe Thr Arg Cys Asn Ile Ala Trp Cys Arg Arg Arg Lys Thr
            20                  25                  30

<210> SEQ ID NO 45
<211> LENGTH: 20
<212> TYPE: PRT
<213> ORGANISM: Mus musculus

<400> SEQUENCE: 45

Leu Gly Arg Tyr Pro Val Leu Glu Val Ile Ala Val Thr Ala Val Thr
1               5                   10                  15

Ala Ile Val Ala
            20

<210> SEQ ID NO 46
<211> LENGTH: 4
<212> TYPE: PRT
<213> ORGANISM: Mus musculus

<400> SEQUENCE: 46

Ile Ser Glu Leu
1

<210> SEQ ID NO 47
<211> LENGTH: 22
<212> TYPE: PRT
<213> ORGANISM: Mus musculus

<400> SEQUENCE: 47

Phe Lys Ile Val Ile Thr Ile Phe Thr Phe Gly Met Lys Ile Pro Ser
1               5                   10                  15

Gly Leu Phe Ile Pro Ser
            20

<210> SEQ ID NO 48
<211> LENGTH: 22
<212> TYPE: PRT
<213> ORGANISM: Mus musculus
```

-continued

<400> SEQUENCE: 48

Leu Phe Ile Pro Ser Met Ala Val Gly Ala Met Ala Gly Arg Met Val
1               5                   10                  15

Gly Ile Gly Val Glu Gln
            20

<210> SEQ ID NO 49
<211> LENGTH: 17
<212> TYPE: PRT
<213> ORGANISM: Mus musculus

<400> SEQUENCE: 49

Pro Gly Leu Tyr Ala Met Val Gly Ala Ala Cys Leu Gly Gly Val
1               5                   10                  15

Thr

<210> SEQ ID NO 50
<211> LENGTH: 13
<212> TYPE: PRT
<213> ORGANISM: Mus musculus

<400> SEQUENCE: 50

Met Thr Val Ser Leu Val Val Ile Met Phe Glu Leu Thr
1               5                   10

<210> SEQ ID NO 51
<211> LENGTH: 18
<212> TYPE: PRT
<213> ORGANISM: Mus musculus

<400> SEQUENCE: 51

Ile Val Pro Leu Met Ala Ala Ala Val Thr Ser Lys Trp Val Ala Asp
1               5                   10                  15

Ala Phe

<210> SEQ ID NO 52
<211> LENGTH: 17
<212> TYPE: PRT
<213> ORGANISM: Mus musculus

<400> SEQUENCE: 52

Gly Ile Tyr Glu Ala His Ile His Leu Asn Gly Tyr Pro Phe Leu Asp
1               5                   10                  15

Val

<210> SEQ ID NO 53
<211> LENGTH: 61
<212> TYPE: PRT
<213> ORGANISM: Mus musculus

<400> SEQUENCE: 53

Val Met Arg Pro Arg Gly Glu Pro Pro Leu Ser Val Leu Thr Gln
1               5                   10                  15

Asp Ser Met Thr Val Glu Asp Val Glu Thr Leu Ile Lys Glu Thr Asp
                20                  25                  30

Tyr Asn Gly Phe Pro Val Leu Val Ser Arg Asp Ser Glu Arg Leu Ile
            35                  40                  45

Gly Phe Ala Gln Arg Arg Glu Leu Ile Leu Ala Ile Lys
        50                  55                  60

<210> SEQ ID NO 54
<211> LENGTH: 51
<212> TYPE: PRT
<213> ORGANISM: Mus musculus

<400> SEQUENCE: 54

Leu Asn Leu Ser Pro Phe Thr Val Thr Asp His Thr Pro Met Glu Thr
1               5                   10                  15

Val Val Asp Ile Phe Arg Lys Leu Gly Leu Arg Gln Cys Leu Val Thr
            20                  25                  30

Arg Ser Gly Arg Leu Leu Gly Ile Ile Thr Lys Lys Asp Val Leu Arg
        35                  40                  45

His Met Ala
    50

<210> SEQ ID NO 55
<211> LENGTH: 44
<212> TYPE: PRT
<213> ORGANISM: Mus Musculus

<400> SEQUENCE: 55

Phe Trp Tyr Ser His Glu Gln Cys Cys Trp Thr Ser Asn Glu Thr Thr
1               5                   10                  15

Phe Glu Asp Arg Asp Lys Cys Pro Leu Trp Gln Lys Trp Ser Glu Leu
            20                  25                  30

Leu Leu Ser Gln Ser Glu Gly Ala Ser Ala Tyr Ile
        35                  40

<210> SEQ ID NO 56
<211> LENGTH: 22
<212> TYPE: PRT
<213> ORGANISM: Mus Musculus

<400> SEQUENCE: 56

Pro Phe Gly Asn Ser Arg Leu Val Leu Phe Tyr Val Glu Tyr His Thr
1               5                   10                  15

Pro Trp Tyr Met Ala Glu
            20

<210> SEQ ID NO 57
<211> LENGTH: 50
<212> TYPE: PRT
<213> ORGANISM: Mus Musculus

<400> SEQUENCE: 57

Phe Asn Asp Cys Gly Ala Leu Glu Ser Ser Gln Leu Cys Asp Tyr Ile
1               5                   10                  15

Asn Asp Pro Asn Met Thr Arg Pro Val Asp Ile Pro Asp Arg Pro
            20                  25                  30

Ala Gly Val Gly Val Tyr Thr Ala Met Trp Gln Leu Ala Leu Ala Leu
        35                  40                  45

Ile Phe
    50

<210> SEQ ID NO 58
<211> LENGTH: 23
<212> TYPE: PRT
<213> ORGANISM: Mus Musculus

<400> SEQUENCE: 58

Leu Ala Tyr His His His Asp Trp Ile Ile Phe Arg Asn Trp Cys Arg

Pro Gly Ala Asp Cys Val Thr
            20

<210> SEQ ID NO 59
<211> LENGTH: 6
<212> TYPE: PRT
<213> ORGANISM: Mus Musculus

<400> SEQUENCE: 59

Ser Lys Tyr Ser Lys Asn
1               5

<210> SEQ ID NO 60
<211> LENGTH: 9
<212> TYPE: PRT
<213> ORGANISM: Mus Musculus

<400> SEQUENCE: 60

Glu Val Ser Tyr Tyr Phe Pro Leu Lys
1               5

<210> SEQ ID NO 61
<211> LENGTH: 194
<212> TYPE: PRT
<213> ORGANISM: Mus Musculus

<400> SEQUENCE: 61

Gly Lys Glu Gly Ile Tyr Glu Ala His Ile His Leu Asn Gly Tyr Pro
1               5                   10                  15

Phe Leu Asp Val Lys Asp Glu Phe Thr His Arg Thr Leu Ala Thr Asp
            20                  25                  30

Val Met Arg Pro Arg Gly Glu Pro Pro Leu Ser Val Leu Thr Gln
        35                  40                  45

Asp Ser Met Thr Val Glu Asp Val Glu Thr Leu Ile Lys Glu Thr Asp
    50                  55                  60

Tyr Asn Gly Phe Pro Val Leu Val Ser Arg Asp Ser Glu Arg Leu Ile
65                  70                  75                  80

Gly Phe Ala Gln Arg Arg Glu Leu Ile Leu Ala Ile Lys Asn Ala Arg
                85                  90                  95

Gln Arg Gln Glu Gly Ile Val Ser Asn Ser Ile Met Tyr Phe Thr Glu
            100                 105                 110

Glu Pro Pro Glu Leu Pro Ala Asn Ser Pro His Pro Leu Lys Leu Arg
        115                 120                 125

Arg Ile Leu Asn Leu Ser Pro Phe Thr Val Thr Asp His Thr Pro Met
    130                 135                 140

Glu Thr Val Val Asp Ile Phe Arg Lys Leu Gly Leu Arg Gln Cys Leu
145                 150                 155                 160

Val Thr Arg Ser Gly Arg Leu Leu Gly Ile Ile Thr Lys Lys Asp Val
                165                 170                 175

Leu Arg His Met Ala Gln Met Ala Asn Gln Asp Pro Glu Ser Ile Met
            180                 185                 190

Phe Asn

<210> SEQ ID NO 62
<211> LENGTH: 686
<212> TYPE: PRT
<213> ORGANISM: Homo sapiens

<400> SEQUENCE: 62

```
Met Leu Leu Ile Gly Leu Leu Ser Gly Ser Leu Ala Gly Leu Ile Asp
1               5                   10                  15

Ile Ser Ala His Trp Met Thr Asp Leu Lys Glu Gly Ile Cys Thr Gly
            20                  25                  30

Gly Phe Trp Phe Asn His Glu His Cys Cys Trp Asn Ser Glu His Val
        35                  40                  45

Thr Phe Glu Glu Arg Asp Lys Cys Pro Glu Trp Asn Ser Trp Ser Gln
    50                  55                  60

Leu Ile Ile Ser Thr Asp Glu Gly Ala Phe Ala Tyr Ile Val Asn Tyr
65                  70                  75                  80

Phe Met Tyr Val Leu Trp Ala Leu Leu Phe Ala Phe Leu Ala Val Ser
                85                  90                  95

Leu Val Lys Val Phe Ala Pro Tyr Ala Cys Gly Ser Gly Ile Pro Glu
            100                 105                 110

Ile Lys Thr Ile Leu Ser Gly Phe Ile Ile Arg Gly Tyr Leu Gly Lys
            115                 120                 125

Trp Thr Leu Val Ile Lys Thr Ile Thr Leu Val Leu Ala Val Ser Ser
        130                 135                 140

Gly Leu Ser Leu Gly Lys Glu Gly Pro Leu Val His Val Ala Cys Cys
145                 150                 155                 160

Cys Gly Asn Ile Leu Cys His Cys Phe Asn Lys Tyr Arg Lys Asn Glu
            165                 170                 175

Ala Lys Arg Arg Glu Val Leu Ser Ala Ala Ala Ala Gly Val Ser
            180                 185                 190

Val Ala Phe Gly Ala Pro Ile Gly Gly Val Leu Phe Ser Leu Glu Glu
        195                 200                 205

Val Ser Tyr Tyr Phe Pro Leu Lys Thr Leu Trp Arg Ser Phe Phe Ala
    210                 215                 220

Ala Leu Val Ala Ala Phe Thr Leu Arg Ser Ile Asn Pro Phe Gly Asn
225                 230                 235                 240

Ser Arg Leu Val Leu Phe Tyr Val Glu Phe His Thr Pro Trp His Leu
            245                 250                 255

Phe Glu Leu Val Pro Phe Ile Leu Leu Gly Ile Phe Gly Gly Leu Trp
            260                 265                 270

Gly Ala Leu Phe Ile Arg Thr Asn Ile Ala Trp Cys Arg Lys Arg Lys
        275                 280                 285

Thr Thr Gln Leu Gly Lys Tyr Pro Val Ile Glu Val Leu Val Val Thr
    290                 295                 300

Ala Ile Thr Ala Ile Leu Ala Phe Pro Asn Glu Tyr Thr Arg Met Ser
305                 310                 315                 320

Thr Ser Glu Leu Ile Ser Glu Leu Phe Asn Asp Cys Gly Leu Leu Asp
            325                 330                 335

Ser Ser Lys Leu Cys Asp Tyr Glu Asn Arg Phe Asn Thr Ser Lys Gly
            340                 345                 350

Gly Glu Leu Pro Asp Arg Pro Ala Gly Val Gly Val Tyr Ser Ala Met
        355                 360                 365

Trp Gln Leu Ala Leu Thr Leu Ile Leu Lys Ile Val Ile Thr Ile Phe
    370                 375                 380

Thr Phe Gly Met Lys Ile Pro Ser Gly Leu Phe Ile Pro Ser Met Ala
385                 390                 395                 400

Val Gly Ala Ile Ala Gly Arg Leu Leu Gly Val Gly Met Glu Gln Leu
            405                 410                 415
```

```
Ala Tyr Tyr His Gln Glu Trp Thr Val Phe Asn Ser Trp Cys Ser Gln
            420                 425                 430

Gly Ala Asp Cys Ile Thr Pro Gly Leu Tyr Ala Met Val Gly Ala Ala
            435                 440                 445

Ala Cys Leu Gly Gly Val Thr Arg Met Thr Val Ser Leu Val Val Ile
            450                 455                 460

Met Phe Glu Leu Thr Gly Gly Leu Glu Tyr Ile Val Pro Leu Met Ala
465                 470                 475                 480

Ala Ala Met Thr Ser Lys Trp Val Ala Asp Ala Leu Gly Arg Glu Gly
            485                 490                 495

Ile Tyr Asp Ala His Ile Arg Leu Asn Gly Tyr Pro Phe Leu Glu Ala
            500                 505                 510

Lys Glu Glu Phe Ala His Lys Thr Leu Ala Met Asp Val Met Lys Pro
            515                 520                 525

Arg Arg Asn Asp Pro Leu Leu Thr Val Leu Thr Gln Asp Ser Met Thr
            530                 535                 540

Val Glu Asp Val Glu Thr Ile Ile Ser Glu Thr Thr Tyr Ser Gly Phe
545                 550                 555                 560

Pro Val Val Val Ser Arg Glu Ser Gln Arg Leu Val Gly Phe Val Leu
            565                 570                 575

Arg Arg Asp Leu Ile Ile Ser Ile Glu Asn Ala Arg Lys Lys Gln Asp
            580                 585                 590

Gly Val Val Ser Thr Ser Ile Ile Tyr Phe Thr Glu His Ser Pro Pro
            595                 600                 605

Leu Pro Pro Tyr Thr Pro Pro Thr Leu Lys Leu Arg Asn Ile Leu Asp
            610                 615                 620

Leu Ser Pro Phe Thr Val Thr Asp Leu Thr Pro Met Glu Ile Val Val
625                 630                 635                 640

Asp Ile Phe Arg Lys Leu Gly Leu Arg Gln Cys Leu Val Thr His Asn
            645                 650                 655

Gly Arg Leu Leu Gly Ile Ile Thr Lys Lys Asp Val Leu Lys His Ile
            660                 665                 670

Ala Gln Met Ala Asn Gln Asp Pro Asp Ser Ile Leu Phe Asn
            675                 680                 685

<210> SEQ ID NO 63
<211> LENGTH: 687
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (8)..(8)
<223> OTHER INFORMATION: Xaa = Ser or Ala
<220> FEATURE:
<221> NAME/KEY: MISC_FEATURE
<222> LOCATION: (10)..(10)
<223> OTHER INFORMATION: Xaa = Ser of Thr
<220> FEATURE:
<221> NAME/KEY: MISC_FEATURE
<222> LOCATION: (14)..(14)
<223> OTHER INFORMATION: Xaa = Leu or Val
<220> FEATURE:
<221> NAME/KEY: MISC_FEATURE
<222> LOCATION: (17)..(17)
<223> OTHER INFORMATION: Xaa = Ile or Leu
<220> FEATURE:
<221> NAME/KEY: MISC_FEATURE
<222> LOCATION: (18)..(18)
<223> OTHER INFORMATION: Xaa = Ser or Ala
```

```
<220> FEATURE:
<221> NAME/KEY: MISC_FEATURE
<222> LOCATION: (19)..(19)
<223> OTHER INFORMATION: Xaa = Ala or Val
<220> FEATURE:
<221> NAME/KEY: MISC_FEATURE
<222> LOCATION: (20)..(20)
<223> OTHER INFORMATION: Xaa = His or Asp
<220> FEATURE:
<221> NAME/KEY: MISC_FEATURE
<222> LOCATION: (29)..(29)
<223> OTHER INFORMATION: Xaa = Ile or Val
<220> FEATURE:
<221> NAME/KEY: MISC_FEATURE
<222> LOCATION: (31)..(31)
<223> OTHER INFORMATION: Xaa = Thr or Leu
<220> FEATURE:
<221> NAME/KEY: MISC_FEATURE
<222> LOCATION: (32)..(32)
<223> OTHER INFORMATION: Xaa = Gly or Ser
<220> FEATURE:
<221> NAME/KEY: MISC_FEATURE
<222> LOCATION: (33)..(33)
<223> OTHER INFORMATION: Xaa = Gly or Ala
<220> FEATURE:
<221> NAME/KEY: MISC_FEATURE
<222> LOCATION: (36)..(36)
<223> OTHER INFORMATION: Xaa = Phe or Tyr
<220> FEATURE:
<221> NAME/KEY: MISC_FEATURE
<222> LOCATION: (37)..(37)
<223> OTHER INFORMATION: Xaa = Asn or Ser
<220> FEATURE:
<221> NAME/KEY: MISC_FEATURE
<222> LOCATION: (40)..(40)
<223> OTHER INFORMATION: Xaa = His or Gln
<220> FEATURE:
<221> NAME/KEY: MISC_FEATURE
<222> LOCATION: (44)..(44)
<223> OTHER INFORMATION: Xaa = Asn or Thr
<220> FEATURE:
<221> NAME/KEY: MISC_FEATURE
<222> LOCATION: (46)..(46)
<223> OTHER INFORMATION: Xaa = Glu or Asn
<220> FEATURE:
<221> NAME/KEY: MISC_FEATURE
<222> LOCATION: (47)..(47)
<223> OTHER INFORMATION: Xaa = His or Glu
<220> FEATURE:
<221> NAME/KEY: MISC_FEATURE
<222> LOCATION: (48)..(48)
<223> OTHER INFORMATION: Xaa = Val or Thr
<220> FEATURE:
<221> NAME/KEY: MISC_FEATURE
<222> LOCATION: (52)..(52)
<223> OTHER INFORMATION: Xaa = Glu or Asp
<220> FEATURE:
<221> NAME/KEY: MISC_FEATURE
<222> LOCATION: (58)..(58)
<223> OTHER INFORMATION: Xaa = Glu or Leu
<220> FEATURE:
<221> NAME/KEY: MISC_FEATURE
<222> LOCATION: (60)..(60)
<223> OTHER INFORMATION: Xaa = Asn or Gln
<220> FEATURE:
<221> NAME/KEY: MISC_FEATURE
<222> LOCATION: (61)..(61)
<223> OTHER INFORMATION: Xaa = Ser or Lys
<220> FEATURE:
<221> NAME/KEY: MISC_FEATURE
<222> LOCATION: (64)..(64)
<223> OTHER INFORMATION: Xaa = Gln or Glu
<220> FEATURE:
<221> NAME/KEY: MISC_FEATURE
<222> LOCATION: (66)..(66)
<223> OTHER INFORMATION: Xaa = Ile or Leu
<220> FEATURE:
<221> NAME/KEY: MISC_FEATURE
<222> LOCATION: (67)..(67)
```

```
<223> OTHER INFORMATION: Xaa = Ile or Leu
<220> FEATURE:
<221> NAME/KEY: MISC_FEATURE
<222> LOCATION: (69)..(69)
<223> OTHER INFORMATION: Xaa = Thr or Gln
<220> FEATURE:
<221> NAME/KEY: MISC_FEATURE
<222> LOCATION: (70)..(70)
<223> OTHER INFORMATION: Xaa = Asp or Ser
<220> FEATURE:
<221> NAME/KEY: MISC_FEATURE
<222> LOCATION: (74)..(74)
<223> OTHER INFORMATION: Xaa = Phe or Ser
<220> FEATURE:
<221> NAME/KEY: MISC_FEATURE
<222> LOCATION: (78)..(78)
<223> OTHER INFORMATION: Xaa = Val or Leu
<220> FEATURE:
<221> NAME/KEY: MISC_FEATURE
<222> LOCATION: (81)..(81)
<223> OTHER INFORMATION: Xaa = Phe or Leu
<220> FEATURE:
<221> NAME/KEY: MISC_FEATURE
<222> LOCATION: (84)..(84)
<223> OTHER INFORMATION: Xaa = Val or Ile
<220> FEATURE:
<221> NAME/KEY: MISC_FEATURE
<222> LOCATION: (99)..(99)
<223> OTHER INFORMATION: Xaa = Lys or Arg
<220> FEATURE:
<221> NAME/KEY: MISC_FEATURE
<222> LOCATION: (132)..(132)
<223> OTHER INFORMATION: Xaa = Val or Leu
<220> FEATURE:
<221> NAME/KEY: MISC_FEATURE
<222> LOCATION: (136)..(136)
<223> OTHER INFORMATION: Xaa = Ile or Val
<220> FEATURE:
<221> NAME/KEY: MISC_FEATURE
<222> LOCATION: (141)..(141)
<223> OTHER INFORMATION: Xaa = Ala or Val
<220> FEATURE:
<221> NAME/KEY: MISC_FEATURE
<222> LOCATION: (164)..(164)
<223> OTHER INFORMATION: Xaa = Ile or Phe
<220> FEATURE:
<221> NAME/KEY: MISC_FEATURE
<222> LOCATION: (165)..(165)
<223> OTHER INFORMATION: Xaa = Leu or Phe
<220> FEATURE:
<221> NAME/KEY: MISC_FEATURE
<222> LOCATION: (166)..(166)
<223> OTHER INFORMATION: Xaa = Cys or Ser
<220> FEATURE:
<221> NAME/KEY: MISC_FEATURE
<222> LOCATION: (167)..(167)
<223> OTHER INFORMATION: Xaa = His or Ser
<220> FEATURE:
<221> NAME/KEY: MISC_FEATURE
<222> LOCATION: (168)..(168)
<223> OTHER INFORMATION: Xaa = Cys or Leu
<220> FEATURE:
<221> NAME/KEY: MISC_FEATURE
<222> LOCATION: (170)..(170)
<223> OTHER INFORMATION: Xaa = Asn or Ser
<220> FEATURE:
<221> NAME/KEY: MISC_FEATURE
<222> LOCATION: (173)..(173)
<223> OTHER INFORMATION: Xaa = Arg or Ser
<220> FEATURE:
<221> NAME/KEY: MISC_FEATURE
<222> LOCATION: (177)..(177)
<223> OTHER INFORMATION: Xaa = Ala or Gly
<220> FEATURE:
<221> NAME/KEY: MISC_FEATURE
<222> LOCATION: (250)..(250)
<223> OTHER INFORMATION: Xaa = Phe or Tyr
<220> FEATURE:
<221> NAME/KEY: MISC_FEATURE
```

```
<222> LOCATION: (255)..(255)
<223> OTHER INFORMATION: Xaa = His or Tyr
<220> FEATURE:
<221> NAME/KEY: MISC_FEATURE
<222> LOCATION: (256)..(256)
<223> OTHER INFORMATION: Xaa = Leu or Met
<220> FEATURE:
<221> NAME/KEY: MISC_FEATURE
<222> LOCATION: (257)..(257)
<223> OTHER INFORMATION: Xaa = Phe or Ala
<220> FEATURE:
<221> NAME/KEY: MISC_FEATURE
<222> LOCATION: (260)..(260)
<223> OTHER INFORMATION: Xaa = Val or Phe
<220> FEATURE:
<221> NAME/KEY: MISC_FEATURE
<222> LOCATION: (267)..(267)
<223> OTHER INFORMATION: Xaa = Ile or Val
<220> FEATURE:
<221> NAME/KEY: MISC_FEATURE
<222> LOCATION: (274)..(274)
<223> OTHER INFORMATION: Xaa = Ala or Thr
<220> FEATURE:
<221> NAME/KEY: MISC_FEATURE
<222> LOCATION: (277)..(277)
<223> OTHER INFORMATION: Xaa = Ile or Thr
<220> FEATURE:
<221> NAME/KEY: MISC_FEATURE
<222> LOCATION: (279)..(279)
<223> OTHER INFORMATION: Xaa = Thr or Cys
<220> FEATURE:
<221> NAME/KEY: MISC_FEATURE
<222> LOCATION: (286)..(286)
<223> OTHER INFORMATION: Xaa = Lys or Arg
<220> FEATURE:
<221> NAME/KEY: MISC_FEATURE
<222> LOCATION: (291)..(291)
<223> OTHER INFORMATION: Xaa = Gln or Arg
<220> FEATURE:
<221> NAME/KEY: MISC_FEATURE
<222> LOCATION: (294)..(294)
<223> OTHER INFORMATION: Xaa = Lys or Arg
<220> FEATURE:
<221> NAME/KEY: MISC_FEATURE
<222> LOCATION: (298)..(298)
<223> OTHER INFORMATION: Xaa = Ile or Leu
<220> FEATURE:
<221> NAME/KEY: MISC_FEATURE
<222> LOCATION: (301)..(301)
<223> OTHER INFORMATION: Xaa = Leu or Ile
<220> FEATURE:
<221> NAME/KEY: MISC_FEATURE
<222> LOCATION: (302)..(302)
<223> OTHER INFORMATION: Xaa = Val or Ala
<220> FEATURE:
<221> NAME/KEY: MISC_FEATURE
<222> LOCATION: (307)..(307)
<223> OTHER INFORMATION: Xaa = Thr or Val
<220> FEATURE:
<221> NAME/KEY: MISC_FEATURE
<222> LOCATION: (308)..(308)
<223> OTHER INFORMATION: Xaa = Ala or Thr
<220> FEATURE:
<221> NAME/KEY: MISC_FEATURE
<222> LOCATION: (309)..(309)
<223> OTHER INFORMATION: Xaa = Ile or Ala
<220> FEATURE:
<221> NAME/KEY: MISC_FEATURE
<222> LOCATION: (310)..(310)
<223> OTHER INFORMATION: Xaa = Leu or Val
<220> FEATURE:
<221> NAME/KEY: MISC_FEATURE
<222> LOCATION: (312)..(312)
<223> OTHER INFORMATION: Xaa = Phe or Tyr
<220> FEATURE:
<221> NAME/KEY: MISC_FEATURE
<222> LOCATION: (315)..(315)
<223> OTHER INFORMATION: Xaa = Glu or Pro
<220> FEATURE:
```

```
<221> NAME/KEY: MISC_FEATURE
<222> LOCATION: (319)..(319)
<223> OTHER INFORMATION: Xaa = Met or Gln
<220> FEATURE:
<221> NAME/KEY: MISC_FEATURE
<222> LOCATION: (334)..(334)
<223> OTHER INFORMATION: Xaa = Leu or Ala
<220> FEATURE:
<221> NAME/KEY: MISC_FEATURE
<222> LOCATION: (336)..(336)
<223> OTHER INFORMATION: Xaa = Asp or Glu
<220> FEATURE:
<221> NAME/KEY: MISC_FEATURE
<222> LOCATION: (339)..(339)
<223> OTHER INFORMATION: Xaa = Lys or Gln
<220> FEATURE:
<221> NAME/KEY: MISC_FEATURE
<222> LOCATION: (344)..(344)
<223> OTHER INFORMATION: Xaa = Glu or Ile
<220> FEATURE:
<221> NAME/KEY: MISC_FEATURE
<222> LOCATION: (346)..(346)
<223> OTHER INFORMATION: Xaa = Arg or Asp
<220> FEATURE:
<221> NAME/KEY: MISC_FEATURE
<222> LOCATION: (347)..(347)
<223> OTHER INFORMATION: Xaa = Phe or Pro
<220> FEATURE:
<221> NAME/KEY: MISC_FEATURE
<222> LOCATION: (349)..(349)
<223> OTHER INFORMATION: Xaa = Met
<220> FEATURE:
<221> NAME/KEY: MISC_FEATURE
<222> LOCATION: (351)..(351)
<223> OTHER INFORMATION: Xaa = Ser or Arg
<220> FEATURE:
<221> NAME/KEY: MISC_FEATURE
<222> LOCATION: (352)..(352)
<223> OTHER INFORMATION: Xaa = Lys or Pro
<220> FEATURE:
<221> NAME/KEY: MISC_FEATURE
<222> LOCATION: (353)..(353)
<223> OTHER INFORMATION: Xaa = Gly or Val
<220> FEATURE:
<221> NAME/KEY: MISC_FEATURE
<222> LOCATION: (354)..(354)
<223> OTHER INFORMATION: Xaa = Gly or Asp
<220> FEATURE:
<221> NAME/KEY: MISC_FEATURE
<222> LOCATION: (355)..(355)
<223> OTHER INFORMATION: Xaa = Glu or Asp
<220> FEATURE:
<221> NAME/KEY: MISC_FEATURE
<222> LOCATION: (356)..(356)
<223> OTHER INFORMATION: Xaa = Leu or Ile
<220> FEATURE:
<221> NAME/KEY: MISC_FEATURE
<222> LOCATION: (367)..(367)
<223> OTHER INFORMATION: Xaa = Ser or Thr
<220> FEATURE:
<221> NAME/KEY: MISC_FEATURE
<222> LOCATION: (375)..(375)
<223> OTHER INFORMATION: Xaa = Thr or Ala
<220> FEATURE:
<221> NAME/KEY: MISC_FEATURE
<222> LOCATION: (378)..(378)
<223> OTHER INFORMATION: Xaa = Leu or Phe
<220> FEATURE:
<221> NAME/KEY: MISC_FEATURE
<222> LOCATION: (405)..(405)
<223> OTHER INFORMATION: Xaa = Ile or Met
<220> FEATURE:
<221> NAME/KEY: MISC_FEATURE
<222> LOCATION: (409)..(409)
<223> OTHER INFORMATION: Xaa = Leu or Met
<220> FEATURE:
<221> NAME/KEY: MISC_FEATURE
<222> LOCATION: (410)..(410)
<223> OTHER INFORMATION: Xaa = Leu or Val
```

```
<220> FEATURE:
<221> NAME/KEY: MISC_FEATURE
<222> LOCATION: (412)..(412)
<223> OTHER INFORMATION: Xaa = Val or Ile
<220> FEATURE:
<221> NAME/KEY: MISC_FEATURE
<222> LOCATION: (414)..(414)
<223> OTHER INFORMATION: Xaa = Met or Val
<220> FEATURE:
<221> NAME/KEY: MISC_FEATURE
<222> LOCATION: (420)..(420)
<223> OTHER INFORMATION: Xaa = Tyr or His
<220> FEATURE:
<221> NAME/KEY: MISC_FEATURE
<222> LOCATION: (422)..(422)
<223> OTHER INFORMATION: Xaa = Gln or His
<220> FEATURE:
<221> NAME/KEY: MISC_FEATURE
<222> LOCATION: (423)..(423)
<223> OTHER INFORMATION: Xaa = Glu or Asp
<220> FEATURE:
<221> NAME/KEY: MISC_FEATURE
<222> LOCATION: (425)..(425)
<223> OTHER INFORMATION: Xaa = Thr or Ile
<220> FEATURE:
<221> NAME/KEY: MISC_FEATURE
<222> LOCATION: (426)..(426)
<223> OTHER INFORMATION: Xaa = Val or Ile
<220> FEATURE:
<221> NAME/KEY: MISC_FEATURE
<222> LOCATION: (428)..(428)
<223> OTHER INFORMATION: Xaa = Asn or Arg
<220> FEATURE:
<221> NAME/KEY: MISC_FEATURE
<222> LOCATION: (429)..(429)
<223> OTHER INFORMATION: Xaa = Ser or Asn
<220> FEATURE:
<221> NAME/KEY: MISC_FEATURE
<222> LOCATION: (432)..(432)
<223> OTHER INFORMATION: Xaa = Ser or Arg
<220> FEATURE:
<221> NAME/KEY: MISC_FEATURE
<222> LOCATION: (433)..(433)
<223> OTHER INFORMATION: Xaa = Gln or Pro
<220> FEATURE:
<221> NAME/KEY: MISC_FEATURE
<222> LOCATION: (438)..(438)
<223> OTHER INFORMATION: Xaa = Ile or Val
<220> FEATURE:
<221> NAME/KEY: MISC_FEATURE
<222> LOCATION: (484)..(484)
<223> OTHER INFORMATION: Xaa = Met or Val
<220> FEATURE:
<221> NAME/KEY: MISC_FEATURE
<222> LOCATION: (493)..(493)
<223> OTHER INFORMATION: Xaa = Leu or Phe
<220> FEATURE:
<221> NAME/KEY: MISC_FEATURE
<222> LOCATION: (495)..(495)
<223> OTHER INFORMATION: Xaa = Arg or Lys
<220> FEATURE:
<221> NAME/KEY: MISC_FEATURE
<222> LOCATION: (500)..(500)
<223> OTHER INFORMATION: Xaa = Asp or Glu
<220> FEATURE:
<221> NAME/KEY: MISC_FEATURE
<222> LOCATION: (504)..(504)
<223> OTHER INFORMATION: Xaa = Arg or His
<220> FEATURE:
<221> NAME/KEY: MISC_FEATURE
<222> LOCATION: (512)..(512)
<223> OTHER INFORMATION: Xaa = Glu or Asp
<220> FEATURE:
<221> NAME/KEY: MISC_FEATURE
<222> LOCATION: (513)..(513)
<223> OTHER INFORMATION: Xaa = Ala or Val
<220> FEATURE:
<221> NAME/KEY: MISC_FEATURE
<222> LOCATION: (515)..(515)
```

```
<223> OTHER INFORMATION: Xaa = Glu or Asp
<220> FEATURE:
<221> NAME/KEY: MISC_FEATURE
<222> LOCATION: (518)..(518)
<223> OTHER INFORMATION: Xaa = Ala or Thr
<220> FEATURE:
<221> NAME/KEY: MISC_FEATURE
<222> LOCATION: (520)..(520)
<223> OTHER INFORMATION: Xaa = Lys or Arg
<220> FEATURE:
<221> NAME/KEY: MISC_FEATURE
<222> LOCATION: (524)..(524)
<223> OTHER INFORMATION: Xaa = Met or Thr
<220> FEATURE:
<221> NAME/KEY: MISC_FEATURE
<222> LOCATION: (528)..(528)
<223> OTHER INFORMATION: Xaa = Lys or Arg
<220> FEATURE:
<221> NAME/KEY: MISC_FEATURE
<222> LOCATION: (532)..(532)
<223> OTHER INFORMATION: Xaa = Asn or Gly
<220> FEATURE:
<221> NAME/KEY: MISC_FEATURE
<222> LOCATION: (533)..(533)
<223> OTHER INFORMATION: Xaa = Asp or Glu
<220> FEATURE:
<221> NAME/KEY: MISC_FEATURE
<222> LOCATION: (535)..(535)
<223> OTHER INFORMATION: Xaa = Leu or Pro
<220> FEATURE:
<221> NAME/KEY: MISC_FEATURE
<222> LOCATION: (537)..(537)
<223> OTHER INFORMATION: Xaa = Thr or Ser
<220> FEATURE:
<221> NAME/KEY: MISC_FEATURE
<222> LOCATION: (552)..(552)
<223> OTHER INFORMATION: Xaa = Ile or Leu
<220> FEATURE:
<221> NAME/KEY: MISC_FEATURE
<222> LOCATION: (554)..(554)
<223> OTHER INFORMATION: Xaa = Ser or Lys
<220> FEATURE:
<221> NAME/KEY: MISC_FEATURE
<222> LOCATION: (557)..(557)
<223> OTHER INFORMATION: Xaa = Thr or Asp
<220> FEATURE:
<221> NAME/KEY: MISC_FEATURE
<222> LOCATION: (559)..(559)
<223> OTHER INFORMATION: Xaa = Ser or Asn
<220> FEATURE:
<221> NAME/KEY: MISC_FEATURE
<222> LOCATION: (564)..(564)
<223> OTHER INFORMATION: Xaa = Val or Leu
<220> FEATURE:
<221> NAME/KEY: MISC_FEATURE
<222> LOCATION: (568)..(568)
<223> OTHER INFORMATION: Xaa = Glu or Asp
<220> FEATURE:
<221> NAME/KEY: MISC_FEATURE
<222> LOCATION: (570)..(570)
<223> OTHER INFORMATION: Xaa = Gln or Glu
<220> FEATURE:
<221> NAME/KEY: MISC_FEATURE
<222> LOCATION: (573)..(573)
<223> OTHER INFORMATION: Xaa = Val or Ile
<220> FEATURE:
<221> NAME/KEY: MISC_FEATURE
<222> LOCATION: (576)..(576)
<223> OTHER INFORMATION: Xaa = Val or Ala
<220> FEATURE:
<221> NAME/KEY: MISC_FEATURE
<222> LOCATION: (577)..(577)
<223> OTHER INFORMATION: Xaa = Leu or Gln
<220> FEATURE:
<221> NAME/KEY: MISC_FEATURE
<222> LOCATION: (580)..(580)
<223> OTHER INFORMATION: Xaa = Asp or Glu
<220> FEATURE:
<221> NAME/KEY: MISC_FEATURE
```

```
<222> LOCATION: (583)..(583)
<223> OTHER INFORMATION: Xaa = Ile or Leu
<220> FEATURE:
<221> NAME/KEY: MISC_FEATURE
<222> LOCATION: (584)..(584)
<223> OTHER INFORMATION: Xaa = Ser or Ala
<220> FEATURE:
<221> NAME/KEY: MISC_FEATURE
<222> LOCATION: (586)..(586)
<223> OTHER INFORMATION: Xaa = Glu or Lys
<220> FEATURE:
<221> NAME/KEY: MISC_FEATURE
<222> LOCATION: (590)..(590)
<223> OTHER INFORMATION: Xaa = Lys or Gln
<220> FEATURE:
<221> NAME/KEY: MISC_FEATURE
<222> LOCATION: (591)..(591)
<223> OTHER INFORMATION: Xaa = Lys or Arg
<220> FEATURE:
<221> NAME/KEY: MISC_FEATURE
<222> LOCATION: (593)..(593)
<223> OTHER INFORMATION: Xaa = Asp or Glu
<220> FEATURE:
<221> NAME/KEY: MISC_FEATURE
<222> LOCATION: (595)..(595)
<223> OTHER INFORMATION: Xaa = Val or Ile
<220> FEATURE:
<221> NAME/KEY: MISC_FEATURE
<222> LOCATION: (598)..(598)
<223> OTHER INFORMATION: Xaa = Thr or Asn
<220> FEATURE:
<221> NAME/KEY: MISC_FEATURE
<222> LOCATION: (601)..(601)
<223> OTHER INFORMATION: Xaa = Ile or Met
<220> FEATURE:
<221> NAME/KEY: MISC_FEATURE
<222> LOCATION: (606)..(606)
<223> OTHER INFORMATION: Xaa = His or Glu
<220> FEATURE:
<221> NAME/KEY: MISC_FEATURE
<222> LOCATION: (607)..(607)
<223> OTHER INFORMATION: Xaa = Ser or Pro
<220> FEATURE:
<221> NAME/KEY: MISC_FEATURE
<222> LOCATION: (609)..(609)
<223> OTHER INFORMATION: Xaa = Pro or Glu
<220> FEATURE:
<221> NAME/KEY: MISC_FEATURE
<222> LOCATION: (612)..(612)
<223> OTHER INFORMATION: Xaa = Pro or Ala
<220> FEATURE:
<221> NAME/KEY: MISC_FEATURE
<222> LOCATION: (613)..(613)
<223> OTHER INFORMATION: Xaa = Tyr or Asn
<220> FEATURE:
<221> NAME/KEY: MISC_FEATURE
<222> LOCATION: (614)..(614)
<223> OTHER INFORMATION: Xaa = Thr or Ser
<220> FEATURE:
<221> NAME/KEY: MISC_FEATURE
<222> LOCATION: (616)..(616)
<223> OTHER INFORMATION: Xaa = Pro or His
<220> FEATURE:
<221> NAME/KEY: MISC_FEATURE
<222> LOCATION: (617)..(617)
<223> OTHER INFORMATION: Xaa = Thr or Pro
<220> FEATURE:
<221> NAME/KEY: MISC_FEATURE
<222> LOCATION: (622)..(622)
<223> OTHER INFORMATION: Xaa = Asn or Arg
<220> FEATURE:
<221> NAME/KEY: MISC_FEATURE
<222> LOCATION: (625)..(625)
<223> OTHER INFORMATION: Xaa = Asp or Asn
<220> FEATURE:
<221> NAME/KEY: MISC_FEATURE
<222> LOCATION: (634)..(634)
<223> OTHER INFORMATION: Xaa = Leu or His
<220> FEATURE:
```

<221> NAME/KEY: MISC_FEATURE
<222> LOCATION: (639)..(639)
<223> OTHER INFORMATION: Xaa = Ile or Thr
<220> FEATURE:
<221> NAME/KEY: MISC_FEATURE
<222> LOCATION: (656)..(656)
<223> OTHER INFORMATION: Xaa = His or Arg
<220> FEATURE:
<221> NAME/KEY: MISC_FEATURE
<222> LOCATION: (657)..(675)
<223> OTHER INFORMATION: Xaa = Asn or Ser
<220> FEATURE:
<221> NAME/KEY: MISC_FEATURE
<222> LOCATION: (671)..(671)
<223> OTHER INFORMATION: Xaa = Lys or Arg
<220> FEATURE:
<221> NAME/KEY: MISC_FEATURE
<222> LOCATION: (673)..(673)
<223> OTHER INFORMATION: Xaa = Ile or Met
<220> FEATURE:
<221> NAME/KEY: MISC_FEATURE
<222> LOCATION: (682)..(682)
<223> OTHER INFORMATION: Xaa = Asp or Glu
<220> FEATURE:
<221> NAME/KEY: MISC_FEATURE
<222> LOCATION: (685)..(685)
<223> OTHER INFORMATION: Xaa = Leu or Met

<400> SEQUENCE: 63

```
Met Leu Leu Ile Gly Leu Leu Xaa Gly Xaa Leu Ala Gly Xaa Ile Asp
  1               5                  10                  15

Xaa Xaa Xaa Xaa Trp Met Thr Asp Leu Lys Glu Gly Xaa Cys Xaa Xaa
             20                  25                  30

Xaa Phe Trp Xaa Xaa His Glu Xaa Cys Cys Trp Xaa Ser Xaa Xaa Xaa
         35                  40                  45

Thr Phe Glu Xaa Arg Asp Lys Cys Pro Xaa Trp Xaa Xaa Trp Ser Xaa
     50                  55                  60

Leu Xaa Xaa Ser Xaa Xaa Glu Gly Ala Xaa Ala Tyr Ile Xaa Asn Tyr
 65                  70                  75                  80

Xaa Met Tyr Xaa Leu Trp Ala Leu Leu Phe Ala Phe Leu Ala Val Ser
                 85                  90                  95

Leu Val Xaa Val Phe Ala Pro Tyr Ala

-continued

```
                260                 265                 270
Gly Xaa Leu Phe Xaa Arg Xaa Asn Ile Ala Trp Cys Arg Xaa Arg Lys
            275                 280                 285
Thr Thr Xaa Leu Gly Xaa Tyr Pro Val Xaa Glu Val Xaa Xaa Val Thr
290                 295                 300
Ala Ile Xaa Xaa Xaa Xaa Ala Xaa Pro Asn Xaa Tyr Thr Arg Xaa Ser
305                 310                 315                 320
Thr Ser Glu Leu Ile Ser Glu Leu Phe Asn Asp Cys Gly Xaa Leu Xaa
                325                 330                 335
Ser Ser Xaa Leu Cys Asp Tyr Xaa Asn Xaa Xaa Asn Xaa Thr Xaa Xaa
            340                 345                 350
Xaa Xaa Xaa Xaa Pro Asp Arg Pro Ala Gly Val Gly Val Tyr Xaa Ala
            355                 360                 365
Met Trp Gln Leu Ala Leu Xaa Leu Ile Xaa Lys Ile Val Ile Thr Ile
370                 375                 380
Phe Thr Phe Gly Met Lys Ile Pro Ser Gly Leu Phe Ile Pro Ser Met
385                 390                 395                 400
Ala Val Gly Ala Xaa Ala Gly Arg Xaa Xaa Gly Xaa Gly Xaa Glu Gln
                405                 410                 415
Leu Ala Tyr Xaa His Xaa Xaa Trp Xaa Xaa Phe Xaa Xaa Trp Cys Xaa
            420                 425                 430
Xaa Gly Ala Asp Cys Xaa Thr Pro Gly Leu Tyr Ala Met Val Gly Ala
            435                 440                 445
Ala Ala Cys Leu Gly Gly Val Thr Arg Met Thr Val Ser Leu Val Val
450                 455                 460
Ile Met Phe Glu Leu Thr Gly Gly Leu Glu Tyr Ile Val Pro Leu Met
465                 470                 475                 480
Ala Ala Ala Xaa Thr Ser Lys Trp Val Ala Asp Ala Xaa Gly Xaa Glu
                485                 490                 495
Gly Ile Tyr Xaa Ala His Ile Xaa Leu Asn Gly Tyr Pro Phe Leu Xaa
                500                 505                 510
Xaa Lys Xaa Glu Phe Xaa His Xaa Thr Leu Ala Xaa Asp Val Met Xaa
            515                 520                 525
Pro Arg Arg Xaa Xaa Pro Xaa Leu Xaa Val Leu Thr Gln Asp Ser Met
530                 535                 540
Thr Val Glu Asp Val Glu Thr Xaa Ile Xaa Glu Thr Xaa Tyr Xaa Gly
545                 550                 555                 560
Phe Pro Val Xaa Val Ser Arg Xaa Ser Xaa Arg Leu Xaa Gly Phe Xaa
                565                 570                 575
Xaa Arg Arg Xaa Leu Ile Xaa Xaa Ile Xaa Asn Ala Arg Xaa Xaa Gln
            580                 585                 590
Xaa Gly Xaa Val Ser Xaa Ser Ile Xaa Tyr Phe Thr Glu Xaa Xaa Pro
            595                 600                 605
Xaa Leu Pro Xaa Xaa Pro Xaa Xaa Leu Lys Leu Arg Xaa Ile Leu
            610                 615                 620
Xaa Leu Ser Pro Phe Thr Val Thr Asp Xaa Thr Pro Met Glu Xaa Val
625                 630                 635                 640
Val Asp Ile Phe Arg Lys Leu Gly Leu Arg Gln Cys Leu Val Thr Xaa
                645                 650                 655
Xaa Gly Arg Leu Leu Gly Ile Ile Thr Lys Lys Asp Val Leu Xaa His
            660                 665                 670
Xaa Ala Gln Met Ala Asn Gln Asp Pro Xaa Ser Ile Xaa Phe Asn
            675                 680                 685
```

<210> SEQ ID NO 64
<211> LENGTH: 687
<212> TYPE: PRT
<213> ORGANISM: Mus musculus

<400> SEQUENCE: 64

```
Met Leu Leu Ile Gly Leu Leu Ala Gly Thr Leu Ala Gly Val Ile Asp
1               5                   10                  15

Leu Ala Val Asp Trp Met Thr Asp Leu Lys Glu Gly Val Cys Leu Ser
            20                  25                  30

Ala Phe Trp Tyr Ser His Glu Gln Cys Cys Trp Thr Ser Asn Glu Thr
        35                  40                  45

Thr Phe Glu Asp Arg Asp Lys Cys Pro Leu Trp Gln Lys Trp Ser Glu
    50                  55                  60

Leu Leu Leu Ser Gln Ser Glu Gly Ala Ser Ala Tyr Ile Leu Asn Tyr
65                  70                  75                  80

Leu Met Tyr Ile Leu Trp Ala Leu Leu Phe Ala Phe Leu Ala Val Ser
                85                  90                  95

Leu Val Arg Val Phe Ala Pro Tyr Ala Cys Gly Ser Gly Ile Pro Glu
            100                 105                 110

Ile Lys Thr Ile Leu Ser Gly Phe Ile Ile Arg Gly Tyr Leu Gly Lys
        115                 120                 125

Trp Thr Leu Leu Ile Lys Thr Val Thr Leu Val Leu Val Val Ser Ser
    130                 135                 140

Gly Leu Ser Leu Gly Lys Glu Gly Pro Leu Val His Val Ala Cys Cys
145                 150                 155                 160

Cys Gly Asn Phe Phe Ser Ser Leu Phe Ser Lys Tyr Ser Lys Asn Glu
                165                 170                 175

Gly Lys Arg Arg Glu Val Leu Ser Ala Ala Ala Ala Gly Val Ser
            180                 185                 190

Val Ala Phe Gly Ala Pro Ile Gly Gly Val Leu Phe Ser Leu Glu Glu
        195                 200                 205

Val Ser Tyr Tyr Phe Pro Leu Lys Thr Leu Trp Arg Ser Phe Phe Ala
    210                 215                 220

Ala Leu Val Ala Ala Phe Thr Leu Arg Ser Ile Asn Pro Phe Gly Asn
225                 230                 235                 240

Ser Arg Leu Val Leu Phe Tyr Val Glu Tyr His Thr Pro Trp Tyr Met
                245                 250                 255

Ala Glu Leu Phe Pro Phe Ile Leu Leu Gly Val Phe Gly Gly Leu Trp
            260                 265                 270

Gly Thr Leu Phe Thr Arg Cys Asn Ile Ala Trp Cys Arg Arg Arg Lys
        275                 280                 285

Thr Thr Arg Leu Gly Arg Tyr Pro Val Leu Glu Val Ile Ala Val Thr
    290                 295                 300

Ala Ile Val Thr Ala Val Ala Tyr Pro Asn Pro Tyr Thr Arg Gln Ser
305                 310                 315                 320

Thr Ser Glu Leu Ile Ser Glu Leu Phe Asn Asp Cys Gly Ala Leu Glu
                325                 330                 335

Ser Ser Gln Leu Cys Asp Tyr Ile Asn Asp Pro Asn Met Thr Arg Pro
            340                 345                 350

Val Asp Asp Ile Pro Asp Arg Pro Ala Gly Val Gly Val Tyr Thr Ala
        355                 360                 365

Met Trp Gln Leu Ala Leu Ala Leu Ile Phe Lys Ile Val Ile Thr Ile
```

-continued

```
              370                 375                 380
Phe Thr Phe Gly Met Lys Ile Pro Ser Gly Leu Phe Ile Pro Ser Met
385                 390                 395                 400

Ala Val Gly Ala Met Ala Gly Arg Met Val Gly Ile Gly Val Glu Gln
                405                 410                 415

Leu Ala Tyr His His His Asp Trp Ile Ile Phe Arg Asn Trp Cys Arg
                420                 425                 430

Pro Gly Ala Asp Cys Val Thr Pro Gly Leu Tyr Ala Met Val Gly Ala
                435                 440                 445

Ala Ala Cys Leu Gly Gly Val Thr Arg Met Thr Val Ser Leu Val Val
                450                 455                 460

Ile Met Phe Glu Leu Thr Gly Gly Leu Glu Tyr Ile Val Pro Leu Met
465                 470                 475                 480

Ala Ala Ala Val Thr Ser Lys Trp Val Ala Asp Ala Phe Gly Lys Glu
                485                 490                 495

Gly Ile Tyr Glu Ala His Ile His Leu Asn Gly Tyr Pro Phe Leu Asp
                500                 505                 510

Val Lys Asp Glu Phe Thr His Arg Thr Leu Ala Thr Asp Val Met Arg
                515                 520                 525

Pro Arg Arg Gly Glu Pro Pro Leu Ser Val Leu Thr Gln Asp Ser Met
                530                 535                 540

Thr Val Glu Asp Val Glu Thr Leu Ile Lys Glu Thr Asp Tyr Asn Gly
545                 550                 555                 560

Phe Pro Val Leu Val Ser Arg Asp Ser Glu Arg Leu Ile Gly Phe Ala
                565                 570                 575

Gln Arg Arg Glu Leu Ile Leu Ala Ile Lys Asn Ala Arg Gln Arg Gln
                580                 585                 590

Glu Gly Ile Val Ser Asn Ser Ile Met Tyr Phe Thr Glu Glu Pro Pro
                595                 600                 605

Glu Leu Pro Ala Asn Ser Pro His Pro Leu Lys Leu Arg Arg Ile Leu
                610                 615                 620

Asn Leu Ser Pro Phe Thr Val Thr Asp His Thr Pro Met Glu Thr Val
625                 630                 635                 640

Val Asp Ile Phe Arg Lys Leu Gly Leu Arg Gln Cys Leu Val Thr Arg
                645                 650                 655

Ser Gly Arg Leu Leu Gly Ile Ile Thr Lys Lys Asp Val Leu Arg His
                660                 665                 670

Met Ala Gln Met Ala Asn Gln Asp Pro Glu Ser Ile Met Phe Asn
                675                 680                 685
```